(12) United States Patent
Garnett

(10) Patent No.: US 10,472,379 B2
(45) Date of Patent: Nov. 12, 2019

(54) RUTHENIUM-SPHINGOMYELIN COMPLEXES AND METHODS FOR THEIR USE IN THE TREATMENT OF TUMORS

(71) Applicant: Garnett McKeen Lab, Inc., Bohemia, NY (US)

(72) Inventor: Merrill Garnett, East Islip, NY (US)

( * ) Notice: Subject to any disclaimer, the term of this patent is extended or adjusted under 35 U.S.C. 154(b) by 0 days.

(21) Appl. No.: 15/589,828

(22) Filed: May 8, 2017

(65) Prior Publication Data
US 2018/0051045 A1     Feb. 22, 2018

Related U.S. Application Data

(60) Provisional application No. 62/339,699, filed on May 20, 2016.

(51) Int. Cl.
| | |
|---|---|
| *C07F 15/00* | (2006.01) |
| *A61K 33/24* | (2019.01) |
| *C07K 14/47* | (2006.01) |
| *A61K 47/54* | (2017.01) |
| *A61K 47/68* | (2017.01) |
| *C07K 5/062* | (2006.01) |

(52) U.S. Cl.
CPC .......... *C07F 15/0046* (2013.01); *A61K 33/24* (2013.01); *A61K 47/547* (2017.08); *A61K 47/548* (2017.08); *A61K 47/6803* (2017.08); *C07K 5/0606* (2013.01); *C07K 14/4717* (2013.01)

(58) Field of Classification Search
None
See application file for complete search history.

(56) References Cited

U.S. PATENT DOCUMENTS

| 5,686,113 A * | 11/1997 | Speaker ............... A61K 9/1652 424/490 |
| 2006/0128912 A1 | 6/2006 | Piers et al. |
| 2013/0116458 A1 | 5/2013 | Couturier et al. |
| 2014/0199407 A1* | 7/2014 | Garnett ............... C07F 15/0066 424/502 |

OTHER PUBLICATIONS

"The structure of a typical antibody molecule" from Immunobiology: The Immune System in Health and Disease. 5th edition., Janeway CA Jr, Travers P, Walport M, et al. New York: Garland Science; 2001. (Year: 2001).*

(Continued)

*Primary Examiner* — Nissa M Westerberg
(74) *Attorney, Agent, or Firm* — McCarter & English, LLP; Beverly W. Lubit

(57) ABSTRACT

The described invention provides a compound comprising an organometallic complex comprising a core of ruthenium and sphingomyelin, with the option of added zinc, that, in a therapeutic amount, through further connections with contributing organic ligands, are effective as chemotherapeutic agents that have an anti-tumor or anti-cancer effect on a tumor comprising tumor cells including a cytotoxic effect on of the tumor cells, inhibition of the growth of the tumor comprising the tumor cells, inhibition of migration of the tumor cells, or any combination of these effects.

40 Claims, 20 Drawing Sheets

(56) References Cited

OTHER PUBLICATIONS

Saraf, Swarnlata, et al. "Sphingosomes a novel approach to vesicular drug delivery." Int J Cur Sci Res. 1.2 (2011): 63-68. (Year: 2011).*

Murphy Sp, et al., MS-275, a class I histone deacetylase inhibitor, protects the p53-deficient mouse against ischemic injury. J Neurochem 2014;129:509-15.

Narlikar Gj et al., Cooperation between complexes that regulate chromatin structure and transcription. Cell. 2002 108(4):475-87.

Nazarov, A.A., et al., Organometallic anticancer agents that interfere with cellular energy processes: A subtle approach to inducing cancer cell death. Dalton Trans. 2013, 42, 2347-2350.

Nazarov, A.A., et al., Protein ruthenation and DNA alkylation: Chlorambucil-functionalized RAPTA complexes and their anticancer activity. Dalton Trans. 2015 44, 3614-3623.

Paul, L.E.H., et al., Reactions of a cytotoxic hexanuclear arene ruthenium assembly with biological ligands. J. Organomet. Chem. 2013, 734, 45-52.

Rathgeb, A., et al., Ruthenium-nitrosyl complexes with glycine, I-alanine, I-valine, I-proline, d-proline, I-serine, I-threonine, and I-tyrosine: Synthesis, X-ray diffraction structures, spectroscopic and electrochemical properties, and antiproliferative activity. Inorg. Chem. 2014, 53, 2718-2729.

Sharma, A.R., et al., Ruthenium complexes: Potential candidate for anti-tumour activity. Int. J. Chem. Tech. Res. 2014, 6, 828-837.

Shi, Yj et al, "Regulation of LSD1 Histone demethylase activity by its associated factors," Molec. Cell. 19:857-64 (2005).

Spreckelmeyer, S., et al., Cellular transport mechanisms of cytotoxic metallodrugs: An overview beyond cisplatin. Molecules 2014, 19, 15584-15610.

Tse, C., et al, Disruption of higher order folding by core histone acetylation dramatically enhances transcription of nucleosomal arrays by RNA polymerase III, Molec. Cell Biol. 18:4629-38 (1998).

Valente, A., et al., Syntheses of macromolecular ruthenium compounds: A new approach for the search of anticancer drugs. Inorganics 2014, 2, 96-114.

Verdin, E et al, "Class II histone deacetylases: versatile regulators," Trends Genet. 19:286-93 (2003).

Vignali M et al. ATP-dependent chromatin-remodeling complexes. Mol Cell Biol. 2000 (6):1899-910.

Wanczyk, et al, "HDACi: going through the mechanisms," Front. Biosci. 16:340-59 (2011).

Wang, X, et al, Effects of histone acetylation on the solubility and folding of the chromatin fiber, J. Biol. Chem. 276:12764-68 (2001).

Wang, Y. et al, "LSD1 is a subunit of the NuRD complex and targets the metastasis program in breast cancer," Cell 138:660-672 (2009).

Witt, O et al, "HDAC family: what are the cancer relevant targets?", Cancer Lett 277:8-21 (2009).

Yang, Xj, et al., "The Rpd3/Had 1 family of lysine deacetylases from bacteria and yeast to mice and men," Nat. Rev. Molec. Cell Biol. 9:206-218 (2008).

Yang, Xj, et al., Lysine Acetylation codified cross talk with other posttranslational modifications, Molec. Cell 31:449-61 (2008).

Yeh, E.T.H., et al., Cardiovascular complications of cancer therapy: Diagnosis, pathogenesis, and management. Circulation 2004;109:3122-31.

Zhang, G, et al., Mammalian Epigenetic Mechanisms, IUBMB Life 66(4): 240-256 (2014).

Adhireksan, Z., et al., Ligand substitutions between ruthenium-cymene compounds can control protein versus DNA targeting and anticancer activity. Nat. Commun. 2014, 5, 3462.

Albi, E.. et al., Chromatin-associated sphingomyelin: metabolism in relation to cell function, Cell Biochem. Funct., Sep.; 21(3):211-5, 2003.

Albini, et al., J. Natl Cancer Instit. 102(1):14-25 (2010).

Aman, F., et al., Anticancer ruthenium(?6-p-cymene) complexes of nonsteroidal anti-inflammatory drug derivatives. Organometallics 2014, 33, 5546-5553.

Bachmann Im, et al., EZH2 expression is associated with high proliferation rate and aggressive tumor subgroups in cutaneous melanoma and cancers of the endometrium, prostate, and breast, J Clin Oncol. Jan. 10, 2006; 24(2):268-73.

Baillif, R., The solid phase of the Ehrlich Ascites tumor in mice, Cancer Research, 1954; 14:554-558.

Battaglia, S. et al, "Transcription factor co-repressors in cancer biology: roles and targeting," Intl J. Cancer 126:2511-19 (2010).

Berdasco, M., Aberrant Epigenetic Landscape in Cancer: How Cellular Identity Goes Awry, Developmental Cell, vol. 19, Issue 5, Nov. 16, 2010, pp. 698-711.

Biffis, A., et al., Poly-NHC Complexes of transition metals: Recent applications and new trends. Adv. Organomet. Chem. 2015, 63, 203-288.

Bradner, Je et al, "Chemical Phylogenetics of histone deacetylases," Nat. Chem. Biol. 6:238-43 (2010).

Chao, H., DNA Interactions with Ruthenium(II) Polypyridine Complexes Containing Asymmetric Ligands, Bioinorg Chem Appl. 2005; 3(1-2): 15-28.

Chi P, et al., Covalent histone modifications—miswritten, misinterpreted and mis-erased in human cancers, Nat Rev Cancer. Jul. 2010; 10(7):457-69.

Collins, I., et al., Diversity-oriented synthetic strategies applied to cancer chemical biology and drug discovery. Molecules 2014, 19, 17221-17255.

Cortez Cc, et al., Chromatin, cancer and drug therapies. Mutat Res 2008;647:44-51.

Cunliffe, Vt, "Eloquent silence: developmental functions of class I histone deacetylases," Curr. Op. Genetic Dev. 18:404-410 (2008).

Dalgliesh Gl, et al., Systematic sequencing of renal carcinoma reveals inactivation of histone modifying genes, Nature. Jan. 21, 2010; 463(7279):360-3.

De Ruijter, Aj et al, Histone deacetylases (HDACs): characterization of the classical HDAC family, Biochem. J. 370:737-49 (2003).

Delcluve, Gp, et al, Role of histone deacetylases in epigenetic regulation: emerging paradigms from studies with Inhibitors, Clinical Epigenetics 4:5 (2012).

Denslow, Sa, et al., " the human Mi-2/NuRD complex and gene regulation," Oncogene 26:5433-5438 (2007).

Dornajafi, M, Characterization and Fabrication of Novel Ruthenium Oxide-Zinc Batteries, Electrical & Computer Engineering Theses and Dissertations, University of Maryland, 2010.

Dragutan, I., et al., Editorial of Special Issue Ruthenium Complex: The Expanding Chemistry of the Ruthenium Complexes, Molecules 2015, 20(9), 17244-17274.

Embon, L. et al,. Probing dynamics and pinning of single vortices in superconductors at nanometer scales, Nature.com, Scientific Reports 5, Article No. 7598 (2015) doi:10.1038/srep07598, Jan. 2015.

Fischle, W. et al, "Enzymatic activity associated with class II HDACs is dependent on a multiprotein complex containing HDAC3 and SMRT/N-CoR," Molec. Cell 9:45-57 (2002).

Fraga, M.F., et al., Loss of acetylation at Lys16 and trimethylation at Lys20 of histone H4 is a common hallmark of human cancer, Nat. Genet., 37 (2005), pp. 391-400.

Girard N, et al., 3-Deazaneplanocin A (DZNep), an inhibitor of the histone methyltransferase EZH2, induces apoptosis and reduces cell migration in chondrosarcoma cells. PLoS One 2014;9:e98176.

Graf, N., Lippard, S. Redox activation of metal-based prodrugs as a strategy for drug delivery. Adv. Drug Deliv. Rev. 2012, 64, 993-1004.

Gregoretti, IV et al, Molecular evolution of the histone deacetylase family: functional implications of phylogenetic analysis, J. Mol. Biol. 338:17-31 (2004).

Grieshaber, D. et al., "Electrochemical biosensors," Sensors, 8: 1400-1458 (2008).

Groth, A., et al., "Chromatin Challenges during DNA replication and repair," Cell 128: 721-33 (2007).

Haberland, M. et al, "The many roles of histone deacetylases in development and physiology: implications for disease and therapy," Nat. Rev. Genet. 10:32-42 (2009).

Haltiwanger, S., "The Electrical Properties of Cancer Cells," Jul. 2010, accessed from royalrife.com/haltiwanger1.

(56) References Cited

OTHER PUBLICATIONS

Hartveit, F., The Survival Time of Mice with Ehrlich's Ascites Carcinoma related to the Sex and Weight of the Mouse, and the Blood Content of the Tumour, Br. J. Cancer. Jun. 1961; 15(2)336-341.

Hayakawa, T, et al., "Physiological roles of class I HDAC complex and histone demethylase," J. Biomed. Biotechnol. 2011:129383 (2011).

Islam, K., et al., In vivo Anticancer Activities of Benzophenone Semicarbazone against Ehrlich Ascites Carcinoma Cells in Swiss Albino Mice, Cancer Biol Med. Dec. 2012; 9(4): 242-247.

Ivry, E. et al., Amino acids as chiral anionic ligands for ruthenium based asymmetric olefin metathesis. Chem. aommun. 2015, 51, 3870-3873.

James, P.F., et al., Electron capture dissociation of diacylglycerophosphocholine and divalent metal ions : competition between charge reduction and radical induced phospholipid fragmentation, 2008 Amer. Soc. Mass Spect., Elsevier, 1044-0305,doi:10.1016/j.jasms, 2008.03.006.

Jenuwein, T, et al., Translating the histone code, Sci. 293:1074-80 (2001).

Jiao, W., et al., E2F-Dependent Repression of Topoisomerase II Regulates Heterochromatin Formation and Apoptosis in Cells with Melanoma-Prone Mutation, Cancer Res., 65:(10):4067-4077, May 2005.

Jones, P.A., et al., The epigenomics of cancer, Cell, 128 (2007), pp. 683-692).

Kandioller, W., et al., Organometallic anticancer complexes of lapachol: Metal centre-dependent formation of reactive oxygen species and correlation with cytotoxicity. Chem. Commun. 2013, 49, 3348-3350.

Kanwal, R., et al., Epigenetic modifications in cancer, Clin Genet. Apr. 2012; 81(4): 303-311.

Kimchi,I., et al., Unified theory of spiral magnetism in the harmonic-honeycomb iridates, alpha, beta, gamma, Li2IrO3, ,arXiv: 1408.3640v3 (cond-matter.str-el) Jun. 15, 2015.

Lee, Kk, et al., Histone acetyltransferase complexes: one size doesn't fit all, Nat. Rev. Molec. Cell Biol. 8:284-95 :2007).

Liang, J. et al, "Nang and Oct4 associate with unique transcriptional repression complexes in embryonic stem cells," Nature Cell Biol. 10:731-39 (2008).

Lindblad, T, et al., Amorphous AlPO4 as Catalyst Support. 5. FTIR Study of CO Absorbed on Transition Metal Ions Supported on Amorphous AlPO4 and SiO2, Acta Chemica Scandinavia,v.45, p. 342-348, 1991.

Luo, Y et al, "Transregulation of histone deacetylase activities through acetylation," J. Biol. Chem. 284:34901-34910 (2009).

Marks, Pa, "Histone deacetylase inhibitors: a chemical genetics approach to understanding cellular functions" Biochim. Biophys. Acta 1799:717-25 (2010).

Martin M et al, "Class IIa histone deacetylases: regulating the regulators," Oncogene 26:5450-67 (2007).

Martin M. et al," Class IIa histone deacetylases: conducting development and differentiation," Int. J. Dev. Biol. 53:291-301 (2009).

Mukherjee, T., et al., Syntheses of enantiopure bifunctional 2-guanidinobenzimidazole cyclopentadienyl ruthenium .aomplexes: Highly enantioselective organometallic hydrogen bond donor catalysts for carbon-carbon bond forming eactions. Organometallics 2014, 33, 6723-6737.

Ablialimov, O., et al., Synthesis, structure, and catalytic activity of new ruthenium(II) indenylidene complexes bearing unsymmetrical N-heterocyclic carbenes. Organometallics 2014, 33, 2160-2171.

Abrikosov, A.A. On the magnetic properties of superconductors of the second group.Soviet Phys. JETP 5, 1174-1182 (1957).

Abrikosov, A.A., The magnetic properties of superconducting alloys, Journal of Physics and Chemistry of Solids, 2 (3), 199-208, 1957.

Adams, R.D., et al., Lewis Acid-Base Interactions Between Metal Atoms and their Applications for the Synthesis of Bimetallic Cluster Complexes, J.Am.Chem.Soc., V.124, No. 20, 5628-9, May 2002.

Boone C et al., Characterization of an in vitro strain of Ehrlich-Lettre ascites carcinoma subjected to many periodic mouse passages, J. Natl. Cancer Inst. 34:725, 1965.

Brabec, V., et al., DNA Binding Mode of Ruthenium Complexes and Relationship to Tumor Cell Toxicity. Drug Resistance Updates 9 (2006) 111-122.

Buzdar, A.U., et al_ Adriamycin and mitomycin C: possible synergistic cardiotoxicity, Cancer Treat. Rep. 62:1005-1008 (1978).

Casimiro, D.R., et al., Electron transfer in ruthenium/zinc porphyrin derivatives of recombinant human myoglobins. Analysis of tunneling pathways in myoglobin and cytochrome c, J. Am. Chem. Soc., 115 (4), pp. 1485-1489,1993.

Choudhary, C. et al, Lysine acetylation targets protein complexes and co-regulates major cellular functions, Science 325:834-40 (2009).

Cole, K.S., et al., "Dispersion and Absorption in Dielectrics. I. Alternating Current Characteristics," J. Chem. Phys. 9: 341-351 (1941).

Crescentini, M. et al., "Recent trends for (bio)chemical impedance sensor electronic interfaces," Electroanalysis, 24(3): 563-572 (2012).

Davidson, G.,Spectroscopic Properties of Inorganic and Organometallic Compounds, Royal Soc. Chem., V.24, P.342, Billing & Sons Ltd. Worcester, Copyright 1991.

Davie, Jr, et al, Nuclear Organization and chromatin dynamics: Sp1, Sp3, and histone deacetylases, Adv. Enzyme Regul. 48:189-208 (2008).

Dragutan, I., et al., Carbenoid transfer in competing reactions catalyzed by ruthenium complexes. Appl. Organomet. Chem. 2014, 28, 211-215.

Garnett, M, et al., "DNA Reductase: A Synthetic Enzyme with Opportunistic Clinical Activity Against Radiation Sickness," International Symposium on Applications of Enzymes in Chemical and Biological Defense, Orlando, Florida, May, 2001, p. 41.

Glozak, Ma, et al, "Acetylation and deacetylation of non-histone proteins," Gene 363:15-23 (2005).

Guidi, F., et al., The molecular mechanisms of antimetastatic ruthenium compounds explored through DIGE proteomics. J. lnorg. Biochem. 2013, 118, 94-99.

Gunanathan, C., et al., Bond activation and catalysis by ruthenium pincer complexes. Chem. Rev. 2014, 114, 12024-12087.

Holder, D. S., "Appendix A: A brief introduction to bioimpedance," in "Electrical Impedance Tomography", Institute of Physics Publishing, Bristol and Philadelphia (2005), pp. 411-422.

Karlic R, et al., Histone modification levels are predictive for gene expression, Proc Natl Acad Sci U S A. Feb. 16, 2010; 107(7):2926-31.

Kolesnick, R.N., Sphingomyelin and derivatives as cellular signals, Prog. Lipid Res. 30 (1), 1-38, 1991.

Komendova, L., et al., Soft vortex matter in a type-I I type-II superconducting bilayer, Phys.Rev. B 88, 094515 (2013).

Latham, Ja, et al., Cross-regulation of histone modifications, Nat. Stud. Molec. Biol. 14:1017-24 (2007).

Lee, Mg et al, "An essential role for CoREST in nucleosomal histone 3 lysine 4 demethylation," Nature 437:432-35 (2005).

Lopez-Serra P, et al., DNA methylation-associated silencing of tumor-suppressor microRNAs in cancer. Oncogene. 2012;31:1609-1622.

Modic, K.A., et al., Realization of a three-dimensional spin-anisotropic harmonic honeycomb iridate, Nature Communications 5, Art. No. 4203, doi:10,1038/ncomms5203, Jun. 2014.

Ohashi, M., et al., Ruthenium polyhydrido clusters having a bridging alkylzinc group, Organometallics, 26 (9) 2230-2339, 2007.

Parra, M, et al., "Regulatory signal transduction pathways for class IIa histone deacetylases," Curr. Opin. Pharmacol. 10:454-60 (2010).

Pettinari, R., et al., Ruthenium(II)-arene RAPTA type complexes containing curcumin and bisdemethoxycurcumin display potent and selective anticancer activity. Organometallics 2014, 33, 3709-3715.

Popat, S., et al., Therapy Insight: anthracyclines and trastuzumab-the optimal management of cardiotoxic side effects, natl Clin. Pract. Oncol. 5(6):324-35 (2008).

Reichart, L.F., "Extracellular matrix molecules," In "Guidebook to the Extracellular Matrix, Anchor, and Adhesion Proteins," (ed. T. Kreis and R. Vale). Oxford, England: Oxford University Press, pp. 335-344, 1999.

(56) References Cited

OTHER PUBLICATIONS

Savickiene J, et al., Euchromatic histone methyltransferase 2 inhibitor, BIX-01294, sensitizes human promyelocytic leukemia HL-60 and NB4 cells to growth inhibition and differentiation. Leuk Res 2014;38:822-9.
Shahbazian, Md et al., "Functions of site-specific histone acetylation and deacetylation," Ann. Rev. Biochem. 76:75-100 (2007).
Shogren-Knaak, et al., Histone H4-K16 acetylation controls chromatin structure and protein interactions, Science 311:844-847 (2006).
Silverstein, Ra and Ekwall, K, "Sin3: a flexible regulator of global gene expression and genome stability," Curr. Genet. 47:1-17 (2005).
Smith, Kt, et al., "Histone deacetylase inhibitors: anticancer compounds," Intl J. Biochem. Cell Biol. 41:21-25 (2009).
Strasser, S., et al., On the chloride lability in electron-rich second-generation ruthenium benzylidene complexes. Monatsh. Chem. 2015, 146, 1143-1151.
Sun, J., et al. Ruthenium (II) Complexes Interact with Human Serum Albumin and Induce Apoptosis of Tumor Cells, Biological Trace Element Research, V.163, Issue 1-2, pp. 266-274, Feb. 2015.
Taniguchi, M. et al., The role of sphingomyelin and sphingomyelin synthases in cell death, proliferation and migration—from animal models to human disorders, Biochem. Biophys. Acta, 1841 (5): 692-703, May 2014.
Taplick, J et al, "Homo-oligomerisation and nuclear localization of mouse histone deacetylase 1," J Molec. Biol. 308:27-38 (2001).
Tosi, G. et al. Geometrically locked vortex lattices in semiconductor quantum fluids. Nat. Commun. 3:1243 doi:10,1038/ncomms2255 (2012).
Tripathi, S.N., et al., The Pd-Ru System (Palladium-Ruthenium), J. of Phase Equilibria, V.14, No. 5, 638-642, 1993.
Tönnemann, J., et al., (Arene)ruthenium complexes with imidazolin-2-imine and imidazolidin-2-imine ligands. Eur. J. Inorg. Chem. 2014, 4287-4293.
Wan, B.S., et al., Synergic Effect of Palladium-Based Bimetallic Catalysts for the Hydrogenation of Nitroaromatics, Reaction Kinetics and Catalysis Letters, V.63, No. 2, 397-401 (1998).
Wisnieski F, et al., Differential expression of histone deacetylase and acetyltransferase genes in gastric cancer and their modulation by trichostatin A. Tumour Biol 2014;35:6373-81.
Wu, K., et al., Mechanism of interstrand migration of organoruthenium anticancer complexes within a DNA duplex. Metallomics 2012, 4, 139-148.
Zhi, H., et al., Oxidative sequence of a ruthenocene-based anticancer drug candidate in a basic environment. Organometallics 2014, 33, 4940-4946.
PCT/US2017/31612. International Search Report and Written Opinion. dated Aug. 7, 2017 (7 pages).

\* cited by examiner

TOROGLOBULIN ELECTROPHORESIS

EFFECT OF INTRAPERITONEAL INJECTION OF TOROGLOBULIN ON PROGRESSION OF EHRLICH ASCITES CARCINOMA IN 24 FEMALE SWISS MICE - A REPRESENTATIVE STUDY

| SURVIVAL | SURVIVE | TOTAL STUDIED | |
|---|---|---|---|
| CONTROL | 0 | 12 → | 0% SURVIVAL |
| TOROGLOB | 7 | 12 → | 58.33% |

| DAYS | MEAN | SEM | |
|---|---|---|---|
| CONTROL | 22.5 | 1.05 | % INCREASED MEAN SURVIVAL |
| TOROGLOBULI | 45.67 | 5.13 | 102.96 |

RUTHENIUM-SPHINGOMYELIN COMPLEXES AND METHODS FOR THEIR USE IN THE TREATMENT OF TUMORS

CROSS-REFERENCE TO RELATED APPLICATIONS

This application claims the benefit of priority to U.S. Provisional Application No. 62/339,699 filed on May 20, 2016, the entire contents of which are incorporated by reference herein.

FIELD OF THE INVENTION

The described invention relates to organometallic complexes capable of charge and/or spin transfer and the use of pharmaceutical compositions comprising such complexes for the treatment of tumors.

BACKGROUND OF THE INVENTION

Histone Modification Mechanisms for Control of Gene Expression

Histones are proteins found in the nuclei of eukaryotic cells that are used by cells to package genomic DNA into higher ordered structures called nucleosomes. The nucleosome comprises approximately 146-147 base pairs of DNA wrapped around the cylindrical core of an eight histone protein complex. The nucleosome forms the fundamental repeating unit of eukaryotic chromatin, and is organized via folding patterns of chains of nucleosomes to form higher ordered structures, and ultimately to form a chromosome.

Several families of histone proteins exist, including H1/H5, H2A, H2B, H3 and H4. Histones H2A, H2B, H3 and H4 are core histones. H1 and H5 are linker histones. Histones and DNA interact with each other in various ways, including hydrogen bonds, nonpolar interactions, salt bridges, and non-specific minor groove insertion. Many of these interactions are between the histone and the backbone repeating unit of DNA. For example, the core histone proteins, H2A, H2B, H3 and H4 are rich in lysine and arginine, which are amino acids with basic side chains. The positive charges of those basic side chains can effectively neutralize the negatively charged DNA backbone. The numerous interactions of histone proteins with the DNA backbone partially explain why almost all sequences of DNA can be bound to a histone octamer to form a nucleosome.

In addition to the core and linker histones, several histone variants are also known to exist, such as H2AZ, H2AX, and H3.3. The variant histones differ slightly in amino acid sequence from the core and linker histones. The nucleosomes that incorporate histone variants may differ in stability from those that only contain the core histones, and may be expressed at different times of organism development or cell cycle to accommodate different rates of DNA transcription or DNA replication. Incorporation of many histone variants has been associated with an altered chromatin structure.

Each of the core histone proteins also has a "tail" region which extends out from the histone-DNA core complex. The histone tails may be post-translationally modified. For example, the tails may be modified by lysine and arginine methylation, lysine acetylation, serine, threonine and tyrosine phosphorylation, and lysine ubiquitination and sumoylation. [Jenuwein, T. and Allis, C D, Translating the histone code, Sci. 293: 1074-80 (2001).] Such modifications can change the local charge of chromatin causing a more "closed" or more "open" state. Modification of the histone tails contributes to the epigenetic regulation of various nuclear processes.

Post-translational modifications to histones may be made that directly or indirectly alter the DNA-histone interaction. Common modifications to histones include acetylation, methylation, ubiquitination, and phosphorylation. Some modifications, such as acetylation or phosphorylation, can directly affect the charge of the histone and dramatically affect nucleosome dynamics. Various patterns of post-translational modifications can modulate the DNA-histone structure either by changing the affinity of the DNA for the histone complex, or by recruiting other proteins that alter the affinity of DNA for the histone complex.

Post-translational modification of histones provides a mechanism whereby a eukaryotic cell can modulate nucleosome and higher order chromatin structure to spatially and temporally control gene expression. A high level of control over gene expression is required for a cell to coordinate complex nuclear processes such as DNA replication, DNA repair, and transcription. The local and specific modulation of chromatin via histone modification is a fundamental mechanism that eukaryotic cells have evolved to achieve the requisite level of control over DNA processes.

The assembly of DNA into nucleosomes and further packing into higher-ordered chromatin forms a restrictive environment for various nuclear processes such as DNA replication, DNA repair, and transcription. This is so because such packing prevents various transcription, replication, and recombination factors from having access to the DNA.

A variety of chromatin remodeling factors modulate nucleosome and chromatic structure using the energy stored in molecules of ATP. For example, remodeling factors comprise SNF2 (Sucrose Non-Fermentable)-like family of the DEAD/Helicase Superfamily2 (HSF2) DNA-stimulated ATP-ases. The hSWI/SNF (SWItch/Sucrose Non-Fermentable) multisubunit complex, which is highly conserved, contains hBrahma (hBRM) or Brahma-related gene 1 (BRG1) ATPases that alter histone-DNA interactions. This in turn allows general transcription factor access to promoter regions of DNA. Thus, certain remodeling complexes may be targeted to promoters by way of interaction with sequence specific transcription factors. [See http://www.biocarta.com/pathfiles/h_hSWI-SNFpathway.asp citing Narlikar G J et al., Cooperation between complexes that regulate chromatin structure and transcription. Cell. 2002 108(4):475-87; Vignali M et al. ATP-dependent chromatin-remodeling complexes. Mol Cell Biol. 2000 (6):1899-910]

Some of the enzymes responsible for modification of histones can also modify proteins involved in other cellular processes. For example, the histone H3K4 methyltransferase SETT/9 catalyzes the methylation of various non-histone proteins, including DNMT1, p53, yes-associated protein (Yap), SUV39H1, and nuclear hormone estrogen receptor alpha (ERα), Zhang, G. and Pradhan, S., Mammalian Epigenetic Mechanisms, IUBMB Life 66(4): 240-256 (2014).

Histone Acetylation

One dynamic post translational modification to histones is the acetylation of the ε-amino group of lysine, which is regulated by opposed activities of lysine acetyltransferases (KATs) and histone deacetylases (HDACs). [Delcluve, G P, et al, Role of histone deacetylases in epigenetic regulation: emerging paradigms from studies with inhibitors, Clinical Epigenetics 4: 5 (2012).]

Acetylation of histone proteins modulates chromatin structure involved in the replication, repair, silencing and transcription of DNA. [Id; citing Groth, A., et al., "Chromatin Challenges during DNA replication and repair," Cell 128: 721-33 (2007); Shahbazian, M D et al., "Functions of site-specific histone acetylation and deacetylation," Ann. Rev. Biochem. 76: 75-100 (2007)]. Hyper acetylation is associated with a decondensed chromatin structure. [Id; citing Shahbazian, M D et al., Functions of site-specific histone acetylation and deacetylation, Ann. Rev. Biochem. 76: 75-100 (2007); Tse, C., et al, Disruption of higher order folding by core histone acetylation dramatically enhances transcription of nucleosomal arrays by RNA polymerase III, Molec. Cell Biol. 18: 4629-38 (1998); Wang, X, et al, Effects of histone acetylation on the solubility and folding of the chromatin fiber, J. Biol. Chem. 276: 12764-68 (2001); Shogren, K M, et al, Histone H4-K16 acetylation controls chromatin structure and protein interactions, Science 311: 844-847 (2006); Davie, J R, et al, Nuclear Organization and chromatin dynamics: Sp1, Sp3, and histone deacetylases, Adv. Enzyme Regul. 48: 189-238 (2008)]. Bromodomain modules of certain proteins, and sometimes lysine (K)—acetyl transferases (KATs), recognize acetylated sites on core histone proteins as part of the chromatin-remodeling mechanism involved in the activation of transcription. [Id; citing Lee, K K, Workman, J L, Histone acetyltransferase complexes: one size doesn't fit all, Nat. Rev. Molec. Cell Biol. 8: 284-95 (2007)].

Lysine acetylation is both regulated by, and regulates other, post-translational modifications, and is involved in the regulation of many cytoplasmic processes and nearly all nuclear functions. [Id; citing Choudhary, C. et al, Lysine acetylation targets protein complexes and co-regulates major cellular functions, Science 325: 834-40 (2009).] Post translational modifications may prevent or lead to a subsequent modification on histone and non-histone proteins by either recruitment or obstruction of binding proteins. [Id, citing Latham, J A, and Dent, S Y, Cross-regulation of histone modifications, Nat. Struct. Molec. Biol. 14: 1017-24 (2007); Yang, X J and Seto E, Lysine Acetylation codified cross talk with other posttranslational modifications, Molec. Cell 31: 449-61 (2008).]

HDACs

Four classes of mammalian histone deacetylases (HDACs) have been identified based on sequence similarity to yeast counterparts. [Id., citing de Ruijter, A J et al, Histone deacetylases (HDACs): characterization of the classical HDAC family, Biochem. J. 370: 737-49 (2003); Gregoretti, I V et al, Molecular evolution of the histone deacetylase family: functional implications of phylogenetic analysis, J. Mol. Biol. 338: 17-31 (2004)]. HDACs from classes I, II, and IV are dependent on Zn2+ for deacetylase activity. Class I HDACs include HDAC1, HDAC2, HDAC3 and HDAC8, and are ubiquitously expressed nuclear enzymes. [Id., citing de Ruijter, A J et al, Histone deacetylases (HDACs): characterization of the classical HDAC family, Biochem. J. 370: 737-49 (2003)]. Class I HDACs, with the exception of HDAC8, are components of a multiprotein complex.

Class I HDACs have been shown, via knock out studies, to be involved in cell proliferation and survival. [Id., citing Marks, P A, "Histone deacetylase inhibitors: a chemical genetics approach to understanding cellular functions<" Biochim. Biophys. Acta 1799: 717-25 (2010); Haberland, M. et al, "The many roles of histone deacetylases in development and physiology: implications for disease and therapy," Nat. Rev. Genet. 10: 32-42 (2009)] HDAC1 and 2 are capable of forming homo- and hetero-dimers with each other, which is required for HDAC activity and which allows the HDACs to act together or separately from one another.

[Id citing Taplick, J et al, "Homo-oligomerisation and nuclear localization of mouse histone deacetylase 1," J Molec. Biol. 308: 27-38 (2001); Luo, Y et al, "Transregulation of histone deacetylase activities through acetylation," J. Biol. Chem. 284: 34901-34910 (2009)] HDAC1 and 2 are each found in multiprotein corepressor complexes, including Sin3, nucleosome-remodeling HDAC (NuRD) and CoREST. Such complexes are recruited to regulatory regions of chromatin by various transcription factors, such as Sp1, Sp3, p53, NF-B and YY1, and have diverse and specific roles. [de Ruijter, A J et al, "Histone deacetylases (HDACs): characterization of the classical HDAC family," Biochem. J. 370: 737-49 (2003); Yang, X J and Seto, E, "The Rpd3/Had 1 family of lysine deacetylases from bacteria and yeast to mice and men," Nat. Rev. Molec. Cell Biol. 9: 206-218 (2008)] The Sin3 core complex comprises many proteins, including HDAC 1 and 2, and serves as a scaffold for the addition of other functional protein modules involved in nucleosome remodeling, DNA methylation, histone methylation and N-acetylglucosamine transferase activity. [Id citing Silverstein, R A and Ekwall, K, "Sin3: a flexible regulator of global gene expression and genome stability," Curr. Genet. 47: 1-17 (2005); Hayakawa, T and Nakayama, J, "Physiological roles of class I HDAC complex and histone demethylase," J. Biomed. Biotechnol. 2011: 129383 (2011)].

The NuRD complex comprises HDAC1 and HDAC2, which act as HDACs, and Mi-2a and/or Mi-2b, which provide(s) an ATP-dependent chromatin-remodeling function. Various other components of the NuRD complex include RbAp46/RbAp48, p66a or p66b, and methyl-CpG-binding domain-containing proteins (MBD2 or MBD3). Only MBD2 is able to recognize methylated DNA. [Id., citing Hayakawa, T and Nakayama, J, "Physiological roles of class I HDAC complex and histone demethylase," J. Biomed. Biotechnol. 2011: 129383 (2011); Denslow, S A and Wade P A, "The human Mi-2/NuRD complex and gene regulation," Oncogene 26: 5433-5438 (2007)] Also, identified as a component of NuRD is the lysine-specific demethylase 1, KDM1/LSD1. [Id., citing Wang, Y. et al, "LSD1 is a subunit of the NuRD complex and targets the metastasis program in breast cancer," Cell 138: 660-672 (2009)].

HDAC1 and HDAC2 have also been identified as components of Nanog- and Oct4-associated deacetylase (NODE) complex. This complex also includes MTA1 or MTA2, p66a or p66b, but not the histone-binding proteins RbAp46/RbAp48 and the helicase-like ATPase Mi-2. The NODE complex has been identified as being a repressor of Nanog and Oct4 genes, thereby controlling embryonic stem cell differentiation. [Id citing Liang, J. et al, "Nanog and Oct4 associate with unique transcriptional repression complexes in embryonic stem cells," Nature Cell Biol. 10: 731-39 (2008)].

The CoREST complex also includes HDAC1 and HDAC2, but comprises proteins different from those of Sin3 and NuRD. KDM1/LSD1, as a component of the CoREST complex, promotes demethylation of H3 dimethylated on lysine 4 (H3K4me2). This, in turn, results in formation of a repressive chromatin structure. [Lee, M G et al, "An essential role for CoREST in nucleosomal histone 3 lysine 4 demethylation," Nature 437: 432-35 (2005); Shi, Y J et al, "Regulation of LSD1 Histone demethylase activity by its associated factors," Molec. Cell. 19: 857-64 (2005)]. CoREST acts as a coactivator of transcription in embryonic and neural stem cells by recruiting H3K4 methyltransferase to the RE1 sites of target genes, but acts as corepressor in terminally differentiating nonneuronal cells by recruiting KDM1/LSD1 to demethylate H3K4me2 and the methyltransferase G9a to methylate H3K9 at the RE1 sites of target genes. [Id citing Cunliffe, V T, "Eloquent silence: developmental functions of class I histone deacetylases," Curr. Op. Genetic Dev. 18: 404-410 (2008)]. CoREST can also associate with other proteins to form larger complexes, such as ZNF217 (a Krüppel-like zinc finger protein that is a proposed oncogene product in breast cancer) or with other complexes, such as C-terminal binding protein (CtBP) complex and chromatin-remodeling complex, SWI/SNF. [Id citing Hayakawa, T and Nakayama, J, "Physiological roles of class I HDAC complex and histone demethylase," J. Biomed. Biotechnol. 2011: 129383 (2011); Battaglia, S. et al, "Transcription factor co-repressors in cancer biology: roles and targeting," Intl J. Cancer 126: 2511-19 (2010)].

Class II HDACs are further grouped into subclass IIa (HDAC4, HDAC5, HDAC7 and HDAC9) and subclass IIb (HDAC6 and HDAC10). Class II HDACs are expressed in a tissue specific manner, and are shuttled between the cytoplasm and nucleus. [Id citing Marks, P. A., Histone deacetylase inhibitors: a chemical genetics approach to understanding cellular functions," Biochim. Biophys. Acta 1799: 717-25 (2010); Haberland, M. et al, "The many roles of histone deacetylases in development and physiology: implications for disease and therapy," Nat. Rev. Genet. 10: 32-42 (2009); Yang, X J and Seto E., "The Rpd3/Hda1 family of lysine deacetylases: from bacteria and yeast to mice and men," Nat. Rev. Molec. Cell Biol. 9: 206-18 (2008); Verdin, E et al, "Class II histone deacetylases: versatile regulators," Trends Genet. 19: 286-93 (2003)].

Subclass IIa HDACs acts as signal transducers characterized by conserved serine residues in the N-terminal regulatory domain that is reversibly phosphorylated. Phosphorylation of those residues results in an interaction with the 14-3-3 proteins, and results in the export of HDACs and the expression of target genes. Several different kinases and phosphatases have been shown to regulate the trafficking of class IIa HDACs from the cytoplasm to the nucleus. [Id citing Parra, M and Verdin E, "Regulatory signal transduction pathways for class IIa histone deacetylases," Curr. Opin. Pharmacol. 10: 454-60 (2010)]. Some investigators have proposed that class IIa HDACs may act as bromodomains under some circumstances, and thereby recognize lysine in a sequence dependent manner and regulate transcription by recruiting chromatin modifying enzymes. [Id, citing Bradner, J E et al, "Chemical Phylogenetics of histone deacetylases," Nat. Chem. Biol. 6: 238-43 (2010)]. Class IIa HDAC may interact with MEF2 to provide additional targeting for the SMRT-NCoR complex, and may interact with numerous other transcription factors. [Id citing Fischle, W. et al, "Enzymatic activity associated with class II HDACs is dependent on a multiprotein complex containing HDAC3 and SMRT/N-CoR," Molec. Cell 9: 45-57 (2002); Martin M et al, "Class IIa histone deacetylases: regulating the regulators," Oncogene 26: 5450-67 (2007); Martin M. et al, "Class IIa histone deacetylases: conducting development and differentiation," Int. J. Dev. Biol. 53: 291-301 (2009)].

Class IIb HDACs (HDAC6 and HDAC10) have fully or partially duplicated catalytic domains. Class IIb HDACs are primarily localized to the cytoplasm, but may shuttle to the nucleus as well. HDAC6 has been identified as involved in microtubule and actin-dependent cell motility via a tubulin deacetylase and a cortactin deacetylase function. HDAC6 also functions to clear misfolded protein through formation of aggresomes or autophagy [Id citing Yang, X J and Seto E, "Lysine Acetylation codified cross talk with other posttranslational modifications," Molec. Cell 31: 449-61 (2008)].

HDACs are found to be upregulated or inappropriately recruited to DNA in several types of cancer. [Id, citing Witt, O et al, "HDAC family: what are the cancer relevant targets?", Cancer Lett 277: 8-21 (2009); Marks, P. A., Histone deacetylase inhibitors: a chemical genetics approach to understanding cellular functions," Biochim. Biophys. Acta 1799: 717-25 (2010)].

Transcriptional Reprogramming by Histone Deacetylase Inhibitors

Several HDAC inhibitors exist for treatment of cancers, cardiovascular diseases, neurodegenerative disorders and pulmonary diseases, and it is believed that the therapeutic benefit is derived from transcription reprogramming. [Haberland, M. et al, "The many roles of histone deacetylases in development and physiology: implications for disease and therapy," Nat. Rev. Genet. 10: 32-42 (2009)]. Approximately 5% to 20% of genes are affected by the inhibition of HDAC activity, with equal numbers being up- and down-regulated. [Id citing Smith, K T and Workman, J L; "Histone deacetylase inhibitors: anticancer compounds," Intl J. Biochem. Cell Biol. 41: 21-25 (2009)]. Most of those effects are the result of downstream consequences of direct transcriptional regulation, such as inhibition of transcription factor deacetylation causing changes to transcription factor-DNA binding. [Id citing Glozak, M A, et al, "Acetylation and deacetylation of non-histone proteins," Gene 363: 15-23 (2005)]. Recent reviews have addressed biological function and gene expression changes as a result of HDAC inhibition. [Marks, P. A., Histone deacetylase inhibitors: a chemical genetics approach to understanding cellular functions," Biochim. Biophys. Acta 1799: 717-25 (2010), Waanczyk, et al, "HDACi: going through the mechanisms," Front. Biosci. 16: 340-59 (2011)].

Cancer

Cancer is a disease in which cells multiply without control and can invade nearby tissue. There are several main types of cancer categorized by the originating tissue of the invasive cells. For example, cancers arising from epithelial cells are termed "carcinomas"; cancers arising from connective tissue or muscle are termed "sarcomas"; and cancers arising from hemopoetic cells are termed "leukemias". Each broad category of cancer comprises many different subtypes according to specific cell type, location in the body, and structural morphology. [Alberts et al., Molecular Biology of the Cell, 4$^{th}$ Ed. 2002]

A neoplasm is an abnormal mass of tissue that is caused by cells dividing more often than they should or that do not die as often as they should. These masses of cells may be benign (not cancer) if they reproduce without normal restraints on cell division, but do not invade surrounding tissue. The neoplasm may be malignant (cancer) if the cells can invade and colonize tissues normally reserved for other cell types. The invasiveness of malignant cells often involves individual cells migrating away from the tumor mass, entering the blood stream or lymph vessels, and migrating to another location to form secondary, metastatic tumor masses. [Alberts et al., Molecular Biology of the Cell, 4$^{th}$ Ed. 2002]

A growing body of scientific literature shows that epigenetic mechanisms such as DNA methylation, histone modification, nucleosome positioning, and micro-RNA expression are involved in the mechanism(s) underlying some types of cancer. Studies have shown that hypermethylation of tumor suppressor genes is associated with deacetylation of histones H3 and H4, loss of H3K4 trimethylation, and an increase in H3K9 methylation and H3K27 trimethylation. [Maria Berdasco, Aberrant Epigenetic Landscape in Cancer:

How Cellular Identity Goes Awry, Developmental Cell, Volume 19, Issue 5, 16 Nov. 2010, Pages 698-711 (citing P. A. Jones, S. B. Baylin, The epigenomics of cancer, Cell, 128 (2007), pp. 683-692)] Other studies have shown that a loss of histone H4 mono- and tri-methylation lysine is associated with human and mouse tumors. [Id. citing M. F. Fraga, et al., Loss of acetylation at Lys16 and trimethylation at Lys20 of histone H4 is a common hallmark of human cancer, Nat. Genet., 37 (2005), pp. 391-400.] Yet further studies have shown that two disease subtypes of prostate cancer, each with distinct risk of tumor recurrence, is associated with the acetylation and demethylation of five different residues of histones H3 and H4. [Id. citing M. F. Fraga, et al., Loss of acetylation at Lys16 and trimethylation at Lys20 of histone H4 is a common hallmark of human cancer, Nat. Genet., 37 (2005), pp. 391-400.]

Several aberrant histone modifier genes that are tissue specific and which have been associated with cancer have been reported. For example, aberrant genes have been found in the classes of histone acetyl transferases (HATs), histone methyltransferases (HMTs), histone deacetylases (HDACs), and histone demethylases (HDMTs). The aberrations of those histone modifier genes include amplifications, mutations, translocations, hypermethylations, over-expressions, and deletions. [Id. citing M. F. Fraga, et al., Loss of acetylation at Lys16 and trimethylation at Lys20 of histone H4 is a common hallmark of human cancer, Nat. Genet., 37 (2005), pp. 391-400.]

The link between cancer and DNA methylation has been known since at least 1983, when it was discovered that the genomes of cancer cells are hypomethylated relative to their normal counterpart tissue. In addition to genome wide hypomethylation, cancer cells may display site-specific CpG island promoter hypermethylation, thereby inactivating transcription. Many of the main biochemical pathways are disrupted by hypermethylation, such as "DNA repair [hMLH1 (mismatch repair gene 1), MGMT (O6-methylguanine-DNA methyltransferase), WRN (Werner syndrome, RecQ helikase like), BRCA1 (breast cancer 1)], cell cycle control (p16 INK4a, p15 I NK4b, RB), Ras signaling [RASSF1A [Ras association (RalGDS/AF-6) domain family member 1], NOREIA], apoptosis [TMS1 (target of methylation-induced silencing 1), DAPK1 (death-associated protein kinase), WIF-1, SFRP1], metastasis [cadherin 1 (CDH1), CDH13, PCDH10], detoxification [GSTP1 (glutathione S-transferase pi 1)], hormone response (ESR1, ESR2), vitamin response [RARB2 (retinoic acid receptor b2), CRBP1] and p53 network [p14 ARF, p73 (also known as TP73), HIC-1] among others." [R Kanwala and S Gupta, Epigenetic modifications in cancer, Clin Genet. 2012 April; 81(4): 303-311.] Hypomethylation of tumor cells results in genome instability and disruption of imprinting patterns. Hypomethylation of cancer cells is commonly associated with oncogenes, such as c-Myc, and can potentially result in oncogene activation. A common loss of imprinting, which results from hypomethylation, is to insulin-like growth factor 2 (IGF2), which has been found in breast, liver, lung, and colon cancer. [Id.]

It has also been reported that human tumors have altered patterns of histone modification, and that such modifications are predictive of gene expression patterns. For example, the local gene expression of human tumors with increased levels of promoter region H3K4me3, H3K27ac, H2BK5ac and H4K20me1 and increased gene body region H3K79me1 and H4K20me1 is associated with high rates of transcription. [Id. citing Karlić R, Chung H R, Lasserre J, Vlahovicek K, Vingron M, Histone modification levels are predictive for gene expression, Proc Natl Acad Sci USA. 2010 Feb. 16; 107(7):2926-31.] Furthermore, HDAC mutation and over expression has been found to be associated with loss of acetylation on tumors. The inappropriate expression of histone methyl transferases and histone demethylases has been found associated with various types of cancer. [Id. citing Chi P, Allis C D, Wang G G, Covalent histone modifications—miswritten, misinterpreted and mis-erased in human cancers, Nat Rev Cancer. 2010 July; 10(7):457-69.] One study showed that mutations that inactivate the histone methyltransferase SETD2, the histone demethylase UTX, and JARID1C are found in renal carcinoma. [Id. citing Dalgliesh G L, et al., Systematic sequencing of renal carcinoma reveals inactivation of histone modifying genes, Nature. 2010 Jan. 21; 463(7279):360-3.] The trimethylation of H3K4 is predictive of prostate-specific antigen serum level elevation after prostatectomy for cancer, and H3 acetylation and H3K9 dimethylation is indicative of cancerous and nonmalignant prostate tissue. [Id. citing Lopez-Serra P, Esteller M. DNA methylation-associated silencing of tumor-suppressor microRNAs in cancer. Oncogene. 2011; 16:1-14.] The expression of EZH2 (enhancer of zeste homolog 2) has been found to be a prognostic indicator of aggressiveness of prostate, breast, and endometrial cancers. [Id. citing Bachmann I M, et al., EZH2 expression is associated with high proliferation rate and aggressive tumor subgroups in cutaneous melanoma and cancers of the endometrium, prostate, and breast, J Clin Oncol. 2006 Jan. 10; 24(2):268-73.]

Several studies have noted an effect of histone deacetylation and methylation inhibitors, such as trichostatin A (TSA), SAHA, DZNep, and BIX-01294, on tumors. [Wisnieski F, Calcagno D Q, Leal M F, Chen E S, Gigek C O, Santos L C, et al. Differential expression of histone deacetylase and acetyltransferase genes in gastric cancer and their modulation by trichostatin A. Tumour Biol 2014; 35:6373-81; Murphy S P, Lee R J, McClean M E, Pemberton H E, Uo T, Morrison R S, et al. MS-275, a class I histone deacetylase inhibitor, protects the p53-deficient mouse against ischemic injury. J Neurochem 2014; 129:509-15; Girard N, Bazille C, Lhuissier E, Benateau H, Llombart-Bosch A, Boumediene K, et al. 3-Deazaneplanocin A (DZNep), an inhibitor of the histone methyltransferase EZH2, induces apoptosis and reduces cell migration in chondrosarcoma cells. PLoS One 2014; 9:e98176; Savickiene J, Treigyte G, Stirblyte I, Valiuliene G, Navakauskiene R. Euchromatic histone methyltransferase 2 inhibitor, BIX-01294, sensitizes human promyelocytic leukemia HL-60 and NB4 cells to growth inhibition and differentiation. Leuk Res 2014; 38:822-9; Cortez C C, Jones P A. Chromatin, cancer and drug therapies. Mutat Res 2008; 647:44-51.

Electrochemical Properties of Living Tissue

A living tissue functions as an electrical machine, and the structure of cells comprising the tissue exhibit electrical properties including, but not limited to, the ability to conduct electricity, create electric fields, and function as electrical generators. The primary charge carriers in living organisms are negatively charged electrons, positively charged hydrogen protons, positively charged sodium, potassium, calcium and magnesium ions and negatively charged anions, particularly phosphate ions. (Reviewed in Haltiwanger, S., "The Electrical Properties of Cancer Cells," July 2010, accessed from royalrife.com/haltiwanger1).

The body uses the exterior cell membrane, and positively charged mineral ions that are maintained in different concentrations on each side of the cell membrane, to create a cell membrane potential (a voltage difference across the membrane) and a strong electrical field around the cell membrane. (As used herein the term "electrical field" refers to the effect which a charged particle or body exerts on charged particles or bodies situated in the medium surrounding it; i.e., if a negatively charged particle is placed within the electric field of a positively charged particle, there will be an attractive force, while there will be a repulsive force if the charges are alike. The electric field is perpendicular to the magnetic field). This electrical field is a readily available source of energy for cellular activities, such as membrane transport, and the generation of electrical impulses in the brain, nerves, heart and muscles. The storage of electrical charge in the membrane and the generation of an electrical field create a battery function so that the liquid crystal (meaning symmetrically packed) electroactive intermediates and catalysts can transfer membrane charge to DNA. The body also uses the mitochondrial membrane and positively charged hydrogen ions to create a strong membrane potential across the mitochondrial membrane. Hydrogen ions are maintained in a high concentration on the outside of the mitochondrial membrane by the action of the electron transport chain (Haltiwanger, S., "The Electrical Properties of Cancer Cells," July 2010, accessed from royalrife.com/haltiwanger1).

Animal cells are organized structures with an internal architecture of cytoskeletal proteins that connects all components of the cell. Cellular components do not randomly float around in the cell but are attached to the cytoskeletal framework and the membranes. Cytoskeletal filaments and tubules form a continuous system that links the cell surface to all organelle structures including passage through the nuclear membrane to the chromosomes. The liquid crystal proteins that compose the cytoskeleton support, stabilize and connect the liquid crystal components of the cell membrane with other cell organelles. The cytoskeletal proteins have multiple roles. They serve as mechanical scaffolds that organize enzymes and water and anchor the cell to structures in the extracellular matrix (ECM) via linkages through the cell membrane, and are dynamic network structures that create a fully integrated electronic that structurally and electronically links and integrates the proteins of the extracellular matrix with the cell organelles. (Haltiwanger, S., "The Electrical Properties of Cancer Cells," July 2010, accessed from the royalrife.com/haltiwanger1).

The cytoskeleton is also attached through cell membrane connectors to liquid crystal protein polymers located in the external extracellular matrix (ECM) and to other cells. The liquid crystal protein polymers of the ECM are mostly composed of collagen, elastin, hylauronic acid, and interweaving glycoproteins such as fibronectin. The ECM is a transit area for the passage of nutrients from the bloodstream into the cells, for toxins released by the cells that pass through to the bloodstream, and for migrating immune cells involved in inflammatory reactions that secrete cytokines and other inflammatory mediators. (Haltiwanger, S., "The Electrical Properties of Cancer Cells," July 2010, accessed from the royalrife.com/haltiwanger1).

Biochemically, the ECM is a metabolically and electrically active space that is involved in regulating cell growth control. Cellular components of the ECM are involved in the local production of growth factors, growth inhibitors and cytokines that affect the growth and metabolic activity of tissue/organ cells. (Reichart, L. F., "Extracellular matrix molecules," In "Guidebook to the Extracellular Matrix, Anchor, and Adhesion Proteins," (ed. T. Kreis and R. Vale). Oxford, England: Oxford University Press, pgs. 335-344, 1999).

Cells are electromagnetic in nature, and are capable of generating their own electromagnetic fields and of harnessing external electromagnetic energy of the right wavelength to communicate, control and drive metabolic reactions. Communications in living organisms are accomplished by chemical communication through the circulatory system and energetic communication through the nervous system. A solid state electronic communication system has also been hypothesized to operate in series and in parallel with the nervous system through the liquid crystal protein polymer connective system continuum of the cytoskeleton and extracellular matrix. It has been hypothesized that this continuum of liquid crystal connections function as electronic semiconductors and fiberoptic cables allowing the shunting of charge and associated electronic energy in and out of the cell. (Haltiwanger, S., "The Electrical Properties of Cancer Cells," July 2010, accessed from the royalrife.com/haltiwanger1).

Most molecules in the body are electrical dipoles capable of oscillations and resonance. Electric fields induce or cause alignment of dipole moments. A dipole moment is a function of polarization processes and the strength of the electric field. When biological tissue is exposed to an electric field in the right frequency and amplitude windows, a preferential alignment of dipoles becomes established. Since the cell membrane contains many dipole molecules, an applied electric field causes a preferential alignment of the dipoles. Both internally generated and externally applied electromagnetic fields can affect cell functions. (Haltiwanger, S., "The Electrical Properties of Cancer Cells," July 2010, accessed from the royalrife.com/haltiwanger1).

Electrical Properties of the Cell in Disease Repair and Healing

The body uses electricity (biocurrents) as part of its mechanism for controlling growth and repair. Some of these biocurrents travel through hydrated liquid crystal semiconducting (the term "semiconductor" refers a material whose conductivity lies between that of an electrical conductor, such as a metal, and an insulator) protein-proteoglycan (collagen-hyaluronic acid) complexes of the ECM. It has been hypothesized that biocurrents in the ECM pass through the cell membrane into the cell and electrons produced in the cell also pass out through the cell membrane. The biological liquid crystal molecules and structures such as hyaluronic acid, prothrombin, DNA, cytoskeletal proteins and cell membranes maintain both an inward and outward current. The inward current flows from the cell membrane to cell structures like mitochondria and DNA, and the outward current flows back along liquid crystal semiconducting cytoskeletal proteins through the cell membrane to the ECM. Electrical charges stored in the cell membrane (capacitance) and electrical charges of oxygen free radicals are normally transferred to DNA and are involved in DNA activation and the creation of an electrical field around DNA. DNA is very effective in transferring large amounts of electrical charge along its long axis. (Haltiwanger (2010) citing Garnett M., "First Pulse: A Personal Journey in Cancer Research," New York, N.Y.: First Pulse Projects, 1998). An alternating current oscillating circuit between the cell membrane and DNA conducted over the electronic liquid crystal network of the cell is thought to be involved in cellular processes such as gene expression. (Garnett, M. and Remo, J. L., "DNA Reductase: A Synthetic Enzyme with Opportunistic Clinical Activity Against Radiation Sickness," International Symposium on Applications of Enzymes in Chemical and Biological Defense, Orlando, Fla., May, 2001, p. 41.)

It has also been hypothesized that electrical pathways between the cell membrane and DNA are related to cell development, and use anaerobic mechanisms of ATP production. This natural electrical pathway is thought to be transiently disrupted in healthy cells that are involved in wound healing and inflammation, and permanently disrupted in cancer cells that rely on anerobic glycolysis for energy production. (Haltiwanger (2010) citing Garnett M., "First Pulse: A Personal Journey in Cancer Research," New York, N.Y.: First Pulse Projects, 1998).

One feature that is characteristic of cancer cells is that they have a lower membrane potential than those of healthy adult cells. In addition to cancerous cells having a lower electrical potential, the electrical connections of cancer cells are disrupted. (Haltiwanger (2010) citing Cone, 1975) This may result in several phenotypic traits of cancer cells; i.e. cancer cells are more easily detached, do not exhibit contact inhibition growth patterns, and have signaling and growth mechanisms independent of normal tissue.

Glycoproteins secreted from the cell interior and cellular components of the ECM produce a glycocalyx that covers the cells. These glycoproteins characteristically have a negative charge. The negative charges of the ECM-glycocalyx interface help determine water balance, ion balance and osmotic balance both in the ground substance of the ECM and inside the cells. ECM proteoglycans exist in fern shapes that allow electric charges to flow, and in disorganized shapes that impair transit through the ECM of electrical currents and nutrients. These disorganized shapes occur in the presence of tissue inflammation and toxins, such as free radicals, reactive oxygen species (e.g. superoxide, peroxide, or hydroxyl ions) in the ECM. Such structures produce pockets of high electrical resistance. (Haltiwanger (2010)).

Some researchers have proposed that the electrical charges stored across the cell lipid bilayer and oxygen free radicals are potentially transferred to molecules of DNA. The transfer of charge along DNA, which is very capable of transferring charge along its axis, may result in activation of DNA. It is possible that the electrical pathway from the cell's lipid bilayer to DNA is related to normal cell functions, such as development and aerobic ATP production. Thus, when the natural electrical pathway of charge is permanently disrupted, it disrupts those normal cell functions.

Measuring Electrical Properties of Biological Tissue

The electrical properties of biological tissue can be measured when current flows through the tissue by a phenomenon termed "impedance" or alternatively "bioimpedance", which refers to an opposition to the flow of alternating current through a conductor, and is described by a relation between voltage and current in a system. (Holder, D. S., "Appendix A: A brief introduction to bioimpedance," in "Electrical Impedance Tomography", Institute of Physics Publishing, Bristol and Philadelphia (2005), pp. 411-422). Impedance is defined as the ratio of incremental change in voltage to the resulting current (or vice versa) across an electrochemical cell or an electrical circuit. (Crescentini, M. et al., "Recent trends for (bio)chemical impedance sensor electronic interfaces," Electroanalysis, 24(3): 563-572 (2012)).

Impedance can be measured in tissues and cells using electrochemical impedance spectroscopy (EIS). Through the application of a small sinusoidally varying potential U, one measures the resulting current response I. By repeating the process at varying excitation frequencies f, impedance can be calculated as a function of the angular frequency $\omega$, given by the relationship:

$$Z(j\omega) = \frac{U(j\omega)}{I(j\omega)} = Z_r(\omega) + jZ_i(\omega),$$

where $\omega=2\Pi f$. (Grieshaber, D. et al., "Electrochemical biosensors," Sensors, 8: 1400-1458 (2008)).

More specifically, when applying a sinusoidal voltage reference $V_{ref}(t)=|V_{ref}|\sin(\omega_0 t)$ across the cell and assuming linear behavior, the corresponding current flowing through the cell is $I(t)=|I|\sin(\omega_0 t+\theta)$, wherein $\theta$ is the phase shift of the signal with respect to the excitation. Thus, the relationship between excitation and readout signals depends only on phases and amplitude ratios. (Crescentini, M. et al., "Recent trends for (bio)chemical impedance sensor electronic interfaces," Electroanalysis, 24(3): 563-572 (2012)). Therefore, impedance is made of two components: resistance or the real part of the data, and reactance, the out-of-phase data. (Crescentini, M. et al., "Recent trends for (bio)chemical impedance sensor electronic interfaces," Electroanalysis, 24(3): 563-572 (2012)).

Resistance (R) is a measure of the extent to which a substance opposes the flow of electrons or, in aqueous solution as in living tissue, the flow of ions among its cells. The three fundamental properties governing the flow of electricity are "voltage", "current" and "resistance". Voltage is the pressure exerted on a stream of charged particles moving down a wire or through an ionized salt solution. Current is the amount of charge flowing per unit time. Resistance is the ease or difficulty with which the charged particles can flow. Voltage, current and resistance are related by Ohm's law: V (voltage, Volts)=I (current, Amps)×R (resistance, Ohms ($\Omega$)). Ohm's law applies to both direct current (d.c. or steadily flowing) or alternating current (a.c. or current that flows backwards and forwards).

Capacitance (C) refers to the extent to which an electronic component, circuit, or system stores and releases energy as the current and voltage fluctuate with each AC cycle. The capacitance physically corresponds to the ability of plates in a capacitor to store charge. With each cycle, charges accumulate and then discharge. Direct current cannot pass through a capacitor. Alternating current can pass because of the rapidly reversing flux of charge. The capacitance is an unvarying property of a capacitive or more complex circuit. However, the effect in terms of the ease of current passage depends on the frequency of the applied current; charges pass backwards and forwards more rapidly if the applied frequency is higher.

Reactance (X), analogous to resistance, refers to the current travelling through a capacitor or a coil. A higher reactance has a higher effective resistance to alternating current. Like resistance, its value is in Ohms, but it depends on the applied frequency, and is described by the relation: Reactance (Ohms)=1/(2×r×Frequency (Hz)×Capacitance (Farads)). When a current is passing through a purely resistive circuit, the voltage recorded across the resistor will coincide exactly with the timing, or phase, of the applied alternating current. However, when current flows across a capacitor, the voltage recorded across it lags behind the applied current because of back and forth flow of current requiring alternating charging and discharging of the plates of the capacitor. In terms of a sine wave which has 360° in a full cycle, the lag is one quarter of a cycle, i.e., 90°.

Impedance is the frequency dependent resistance derived from the following three components of an AC circuit: direct current (DC) resistance; capacitive resistance; and inductive reactance. Capacitance is produced by storing charge on a surface at an energy expense producing a retardation of voltage flow. Inductance is produced by storing energy in a magnetic field in bulk space at an energy expense producing a retardation of current flow. Capacitance is counted in Farad units and inductance in Henry units. These two retardation effects are combined in a process and representation called the phase angle, which is the angular summation of the two waves or pulses of voltage and current. In the Mott-Schottky form of impedance measurement, only a single frequency influence is used. This is a departure from Nyquist or Cole (Cole, K. S. and Cole, R. H, "Dispersion and Absorption in Dielectrics. I. Alternating Current Characteristics," J. Chem. Phys. 9: 341-351 (1941)) plots, which utilize a descending frequency series. The Mott-Schottky method is useful for analysis of the underlying impedance vectors within devices and within molecules.

Vortex Theory

Vortex theory is widely used in physics (Ginzburg-Landau theory, superconductivity, spiral galaxies, black holes, aerodynamics, hydrodynamics), but appears to be rarely used in molecular biology. The superconducting vortex lattice was first predicted by the Nobel laureate Alexei Abrikosov, who predicted that a vortex supercurrent circulates around the core of a magnetic vortex due to the circulating supercurrent's production of magnetic fields. [Abrikosov, A. A. On the magnetic properties of superconductors of the second group. Soviet Phys. JETP 5, 1174-1182 (1957); Abrikosov, A. A., The magnetic properties of superconducting alloys, Journal of Physics and Chemistry of Solids, 2(3), 199-208, 1957]. Typically, the arrangement of the small spiraling magnetic vortices is an orderly honeycomb lattice array.

Vortex theory facilitates understanding the equilibrium geometry between magnetic spirals and their unexpected precursors, hexagonal lattices. These forms may be produced in various mediums such as Aluminum-Gallium-Arsenic (Al—Ga—As) layers by underlying vector forces as described in descriptions of vortex production in phase-dependent circle forms and hexagonal honeycomb lattice forms. [Tosi, G. et al. Geometrically locked vortex lattices in semiconductor quantum fluids. Nat. Commun. 3:1243 doi: 10,1038/ncomms2255 (2012).] In such a medium, pulsed laser mirror array excitations of highly defined layers of Al—Ga—As in semiconductor microcavities produces excited state photons called polaritons. These quasi-particle pump fields sculpture the resulting condensates. The condensate forms, the selection of which was controlled by blue-shifting the excitations, are those of both hexagonal honeycomb lattices and vortex and anti-vortex circles. These optical systems are equivalent to one and two dimensional spin systems. [Id.]

Physical-chemistry studies in iridium complexes showed the association between the hexagonal honeycomb lattice and the spiral magnetic field [Kimchi, I., Coldea, R., Vishwanath, A., Unified theory of spiral magnetism in the harmonic-honeycomb iridates, alpha, beta, gamma, Li2IrO3, arXiv: 1408.3640v3 (cond-matter.str-el) 15 Jun. 2015; K. A. Modic et al., Realization of a three-dimensional spin-anisotropic harmonic honeycomb iridate, Nature Communications 5, Art. no. 4203, doi:10,1038/ncomms5203, June 2014.]

Other studies investigating the organization transitions of vortices under the influence of magnetic field, current, and temperature, have shown that many interactive vortex structures may be produced, including clusters, chains, and mazes. Tunable effects produce transitions from short-range clustering to long range order such as parallel chains, gels, glasses, and crystalline lattices. [L. Komendova, M. V. Milosevic, and F. M. Peeters, Soft vortex matter In a type-I/type-II superconducting bilayer, Phys. Rev. B 88, 094515 (2013)].

Ruthenium Compounds and Complexes

Ruthenium is a transition metal of group 8 of the periodic table. Its electronic configuration is 1s2 2s2p6 3s2p6d10 4s2p6d7 5s1. Ruthenium complexes have been described as having the capability to interact with DNA. [Hui Chao, DNA Interactions with Ruthenium(II) Polypyridine Complexes Containing Asymmetric Ligands, Bioinorg Chem Appl. 2005; 3(1-2): 15-28.] Certain ruthenium compounds have been described as having wide ranging biological effects on cells, and have been investigated for the development of disease therapies.

Ruthenium is capable of the widest range of oxidation states of any element, and Ru(II) and Ru(III) oxidation states are capable of six-coordinated octahedral configurations. Additional ligands are able to fine tune the steric and electronic properties of ruthenium complexes. [Ileana Dragutan, et al., Editorial of Special Issue Ruthenium Complex: The Expanding Chemistry of the Ruthenium Complexes, Molecules 2015, 20(9), 17244-17274.] The weak strength of particular metal-ligand bonds and the thermodynamic stability of Ru(III) complexes vs. Ru(II) complexes are also important and can effect ligand exchange kinetics. [Id. citing Strasser, S.; Pump, E.; Fischer, R. C.; Slugovc, C. On the chloride lability in electron-rich second-generation ruthenium benzylidene complexes. Monatsh. Chem. 2015, 146, 1143-1151.] By varying ligands ancillary to ruthenium complexes, it is possible to modulate their reduction/oxidation properties, which allows a large platform of ruthenium complexes having either achiral or chiral configurations. [Id. citing Gunanathan, C.; Milstein, D. Bond activation and catalysis by ruthenium pincer complexes. Chem. Rev. 2014, 114, 12024-12087; Tonnemann, J.; Scopelliti, R.; Severin, K. (Arene)ruthenium complexes with imidazolin-2-imine and imidazolidin-2-imine ligands. Eur. J. Inorg. Chem. 2014, 2014, 4287-4293; Ablialimov, O.; Kedziorek, M.; Maliñska, M.; Woźniak, K.; Grela, K. Synthesis, structure, and catalytic activity of new ruthenium(II) indenylidene complexes bearing unsymmetrical N-heterocyclic carbenes. Organometallics 2014, 33, 2160-2171; Mukherjee, T.; Ganzmann, C.; Bhuvanesh, N.; Gladysz, J. A. Syntheses of enantiopure bifunctional 2-guanidinobenzimidazole cyclopentadienyl ruthenium complexes: Highly enantioselective organometallic hydrogen bond donor catalysts for carbon-carbon bond forming reactions. Organometallics 2014, 33, 6723-6737; Dragutan, I.; Dragutan, V.; Verpoort, F. Carbenoid transfer in competing reactions catalyzed by ruthenium complexes. Appl. Organomet. Chem. 2014, 28, 211-215; Biffis, A.; Baron, M.; Tubaro, C. Poly-NHC Complexes of transition metals: Recent applications and new trends. Adv. Organomet. Chem. 2015, 63, 203-288; Ivry, E.; Ben-Asuly, A.; Goldberg, I.; Lemcoff, N. G. Amino acids as chiral anionic ligands for ruthenium based asymmetric olefin metathesis. Chem. Commun. 2015, 51, 3870-3873; Carreira, E. M.; Yamamoto, H. Synthetic Methods III—Catalytic Methods: C—C Bond Formation. In Comprehensive Chirality; Elsevier: Amsterdam, The Netherlands, 2012; Volume 4.]

Several ruthenium based metallodrugs, which rely on ruthenium chemistry, are able to differentially target tumor cells among healthy cells. Such compounds comprise dendrimers, dendronized polymers, protein conjugates, intelligent nanoparticles, and polymer Ru-complex conjugates. [Id. citing Valente, A.; Garcia, M. H. Syntheses of macromolecular ruthenium compounds: A new approach for the search of anticancer drugs. Inorganics 2014, 2, 96-114.] These ruthenium complexes are believed to function through mechanisms different from platinum drugs that are active through interaction with DNA. [Id. citing Spreckelmeyer, S.; Orvig, C.; Casini, A. Cellular transport mechanisms of cytotoxic metallodrugs: An overview beyond cisplatin. Molecules 2014, 19, 15584-15610; Adhireksan, Z.; Davey, G. E.; Campomanes, P.; Groessl, M.; Clavel, C. M.; Yu, H.; Nazarov, A. A.; Yeo, C. H. F.; Ang, W. H.; Droge, P.; et al. Ligand substitutions between ruthenium-cymene compounds can control protein versus DNA targeting and anticancer activity. Nat. Commun. 2014, 5, 3462; Nazarov, A. A.; Gardini, D.; Baqué, M.; Juillerat-Jeanneret, L.; Serkova, T. P.; Shevtsova, E. P.; Scopelliti, R.; Dyson, P. J. Organometallic anticancer agents that interfere with cellular energy processes: A subtle approach to inducing cancer cell death. Dalton Trans. 2013, 42, 2347-2350; Nazarov, A. A.; Meier, S. M.; Zava, O.; Nosova, Y. N.; Milaeva, E. R.; Hartinger, C. G.; Dyson, P. J. Protein ruthenation and DNA alkylation: Chlorambucil-functionalized RAPTA complexes and their anticancer activity. Dalton Trans. 2015, 44, 3614-3623; Sharma, A. R.; Gangrade, D. M.; Bakshi, S. D.; John, J. S. Ruthenium complexes: Potential candidate for anti-tumour activity. Int. J. Chem. Tech. Res. 2014, 6, 828-837; Guidi, F.; Modesti, A.; Landini, I.; Nobili, S.; Mini, E.; Bini, L.; Puglia, M.; Casini, A.; Dyson, P. J.; Gabbiani, C.; et al. The molecular mechanisms of antimetastatic ruthenium compounds explored through DIGE proteomics. J. Inorg. Biochem. 2013, 118, 94-99; Wu, K.; Luo, Q.; Hu, W.; Li, X.; Wang, F.; Xiong, S.; Sadler, P. J. Mechanism of interstrand migration of organoruthenium anticancer complexes within a DNA duplex. Metallomics 2012, 4, 139-148.] Other antitumor complexes of ruthenium are known. [Viktor Brabec, Olga Novakova, DNA Binding Mode of Ruthenium Complexes and Relationship to Tumor Cytotoxicity, ZP.tech online, www.mitochondrial.net/showabstract.php?p-mid=16790363, June 2006; Jing Sun, Yongchao Huang, Chuping Zheng, Yanhui Zhou, Ying Liu, Jie Liu, Ruthenium (II) Complexes Interact with Human Serum Albumin and Induce Apoptosis of Tumor Cells, Biological Trace Element Research, V. 163, Issue 1-2, pp 266-274, February 2015; Jiao, W., et al., E2F-Dependent Repression of Topoisomerase II Regulates Heterochromatin Formation and Apoptosis in Cells with Melanoma-Prone Mutation, Cancer Res., 65(10):4067-4077, May 2005.]

Ruthenium complexes are believed to act as redox-activatable prodrugs. [Id. citing Lippard, S. J.; Graf, N. Redox activation of metal-based prodrugs as a strategy for drug delivery. Adv. Drug Deliv. Rev. 2012, 64, 993-1004; Lee, H. Z. S.; Buriez, O.; Labbé, E.; Top, S.; Pigeon, P.; Jaouen, G.; Amatore, C.; Leong, W. K. Oxidative sequence of a ruthenocene-based anticancer drug candidate in a basic environment. Organometallics 2014, 33, 4940-4946.]

Ligands of biological origin are capable of minimizing toxicity of ruthenium compounds, enhancing their compatibility with a biological environment, and modulating coordination modes. Such biologically derived ligands include amino acids, peptides, proteins, carbohydrates, purine bases, oligonucleotides, and steroids, among others. [Id. citing Paul, L. E. H.; Furrer, J.; Therrien, B. Reactions of a cytotoxic hexanuclear arene ruthenium assembly with biological ligands. J. Organomet. Chem. 2013, 734, 45-52; Rathgeb, A.; Bohm, A.; Novak, M. S.; Gavriluta, A.; Domotor, O.; Tommasino, J. B.; Enyedy, E. A.; Shova, S.; Meier, S.; Jakupec, M. A.; et al. Ruthenium-nitrosyl complexes with glycine, 1-alanine, 1-valine, 1-proline, d-proline, 1-serine, 1-threonine, and 1-tyrosine: Synthesis, X-ray diffraction structures, spectroscopic and electrochemical properties, and antiproliferative activity. Inorg. Chem. 2014, 53, 2718-2729; Aman, F.; Hanif, M.; Siddiqui, W. A.; Ashraf, A.; Filak, L. K.; Reynisson, J.; Sohnel, T.; Jamieson, S. M. F.; Hartinger, C. G. Anticancer ruthenium(η6-p-cymene) complexes of nonsteroidal anti-inflammatory drug derivatives. Organometallics 2014, 33, 5546-5553; Kandioller, W.; Balsano, E.; Meier, S. M.; Jungwirth, U.; Goschl, S.; Roller, A.; Jakupec, A.; Berger, W.; Keppler, B. K.; Hartinger, C. G. Organometallic anticancer complexes of lapachol: Metal centre-dependent formation of reactive oxygen species and correlation with cytotoxicity. Chem. Commun. 2013, 49, 3348-3350; Pettinari, R.; Marchetti, F.; Condello, F.; Pettinari, C.; Lupidi, G.; Scopelliti, R.; Mukhopadhyay, S.; Riedel, T.; Dyson, P. J. Ruthenium(II)-arene RAPTA type complexes containing curcumin and bisdemethoxycurcumin display potent and selective anticancer activity. Organometallics 2014, 33, 3709-3715; Collins, I., Jones, A. M., Diversity-oriented synthetic strategies applied to cancer chemical biology and drug discovery. Molecules 2014, 19, 17221-17255.]

Complexes containing ruthenium and zinc have been reported, but none of these have been of pharmaceutical use. [Dornajafi, M, Characterization and Fabrication of Novel Ruthenium Oxide-Zinc Batteries, Electrical & Computer Engineering Theses and Dissertations, University of Maryland, 2010; Casimiro, D. R., Wong, L. L., Colon, J. L., Zewert, T. E., Richards, J. H., Chang, I. J., Winkler, J. R., Gray, H. B., Electron transfer in ruthenium/zinc porphyrin derivatives of recombinant human myoglobins. Analysis of tunneling pathways in myoglobin and cytochrome c, J. Am. Chem. Soc., 115 (4), pp 1485-1489, 1993.]

Electron Spin

According to quantum theory, each electron has a spin that is associated with an angular momentum leading to a magnetic moment. Consequently, the negative charge carried by the electron is also associated with a spin resulting in a circulating electric current. The circulating current induces a magnetic moment $\mu_S$ which, if the electron is subjected to a steady magnetic field $H_0$, causes the electron to experience a torque that tends to align the magnetic moment with the field. The energy of the system depends upon the projection of the spin vector along $H_0$. Quantum theory stipulates that only two values are permitted for an electron, which means that the electron magnetic moment can only assume two projections or spin states onto the applied field: the "+½ spin state", when the electron's magnetic moment $\mu_S$ is aligned with the direction of the applied magnetic field $H_0$; and the "+½ spin state", when the electron's magnetic moment $\mu_S$ is aligned opposed to the direction of $H_0$. Consequently, the ensemble of energy levels also reduces to two values, designated as $E_+$, a lower energy level corresponding to the +½ spin state (aligned with the direction of the applied magnetic field) and $E_-$, a higher energy level corresponding to the -½ spin state (opposed to the direction of the applied magnetic field). Because the +½ spin state is of slightly lower energy, in a large population of electrons, slightly more than half of the electrons will occupy this state, while slightly less than half will occupy the -½ spin state. The slight excess of the electron spin in the direction of the magnetic field constitutes a slight net magnetization of the material, a phenomenon known as spin polarization. The difference in energy between the two spin states increases with increasing strength of the magnetic field $H_0$. The higher the strength of $H_0$, the more the net magnetization or the spin polarization, i.e. the higher the number of electrons that will occupy the +½ state as compared to the −½ state.

In addition to the spinning motion, the angular momentum vector of a spinning electron as a result of the torque exhibits a precession around the external field axis with an angular frequency $\omega_L$. The precessional motion, known as Larmour precession, is similar to a spinning top whose spin axis rotates slowly around the vertical. The frequency of precession, $\omega_L$ termed the Larmour frequency, is the number of times per second the electron precesses in a complete circle. The precessional frequency increases the strength of the magnetic field $H_0$.

If an electron that is precessing in an applied magnetic field is exposed to electromagnetic radiation of a frequency $\omega_A$ that matches with the precessional frequency $\omega_L$, the resulting condition is known as resonance. In the resonance condition, an electron of a lower energy +½ spin state (aligned with the applied magnetic field) will transition or flip to the higher energy −½ spin state (opposed to the applied magnetic field). In doing so, the electron absorbs radiation at this resonance frequency, $\omega_A = \omega_L$. This frequency corresponds to the separation between the energy levels of the two spin states, equal to $\Delta E = E_+ - E_-$. This phenomenon is called electron spin resonance (ESR). ESR measures a molecular splitting constant, which is the Gaussian distance or hyperfine shift between the repetitive peaks.

When stimulated by a reaction, the rate of precession can increase, and the dynamic effect is described as Rabi frequency. According to Maxwell-Faraday-Heaviside laws, a moving charge produces a magnetic field in its path, given by: Curl B=4 pi C, where Curl is the net circulating magnetic energy, and C is the charge density or rate of charge moving through a cross section of space or material.

When an atom or molecule has an even number of electrons, electron spins pair off in atomic or molecular orbitals so that virtually no net spin magnetism is exhibited; such material is said to be "diamagnetic". However, when an atom or molecule has an odd number of electrons, complete pairing is not possible and the material is said to be "paramagnetic". The phenomena of spin magnetism (spin polarization) and ESR are observed in paramagnetic materials. The minimally attracted spinning d-orbital electrons in ruthenium render paramagnetic properties in ruthenium complexes.

The motion of the rutheneum d-orbital electrons produces an intermittent or pulsed magnetic field. In suitable ruthenium complexes, the d-orbital electrons are capable of introducing long range molecular magnetic signals into chemical systems. Thus, ruthenium can form coordination complexes with suitable solubility, voltametric behavior, and oxidation state. The inorganic catalyst literature identifies the palladium-ruthenium system (Pd—Ru) (Tripathi, S. N., Bharadwaj, S. R., Dharwadkar, S. R., The Pd—Ru System (Palladium-Ruthenium), J. of Phase Equilibria, V. 14, No. 5, 638-642, 1993; Adams, R. D., Captain, B. F. W., Smith, M. D. Lewis Acid-Base Interactions Between Metal Atoms and their Applications for the Synthesis of Bimetallic Cluster Complexes, J. Am. Chem. Soc., V. 124, No. 20, 5628-9, May 2002) as having a singular peritectic phase with synergic effect on the catalytic hydrogenation of nitroaromatics (Wan, B. S., Liao, S. J., XU, Y., Yu, D. R., Synergic Effect of Palladium-Based Bimetallic Catalysts for the Hydrogenation of Nitroaromatics, Reaction Kinetics and Catalysis Letters, V. 63, No. 2, 397-401). In peritectic transformations, a liquid and solid of fixed proportions react to form a new microcrystal phase capable of nucleation and growth. Pd—Ru also has Lewis acid-base interactions between the metal atoms (Tripathi, S. N., Bharadwaj, S. R., Dharwadkar, S. R., The Pd—Ru System (Palladium-Ruthenium), J. of Phase Equilibria, V. 14, No. 5, 638-642, 1993; Adams, R. D., Captain, B. F. W., Smith, M. D. Lewis Acid-Base Interactions Between Metal Atoms and their Applications for the Synthesis of Bimetallic Cluster Complexes, J. Am. Chem. Soc., V. 124, No. 20, 5628-9, May 2002).

There is a great need to develop novel molecules to which cancer cells are sensitive. Towards that end, the present invention describes organo-metallic complexes comprising ruthenium, and their charge transfer properties.

The formation of nucleosomes in which DNA is wound around a histone spool is believed to be a natural form for condensed DNA and gene suppression. For example, in a prior invention, we introduced a palladium-lipoic acid complex (PLA) which produces heterochromatin in tumor cells. PLA is in Phase II clinical trials.

What was demonstrated through PLA studies was that tumor DNA could be condensed by electron reduction. The PLA studies also showed that an electron redox pathway could be catalyzed by the spin properties of a D-orbital metal bonded to a ligand involved in energy metabolism (lipoic acid). After the example of PLA, other molecular systems were sought which were spin active and strategically located in the cell.

It was believed there were other reservoirs of cell charge besides the mitochondrial site I of lipoic acid. For example, membrane charge might conceivably be mobilized. Membrane charge could theoretically become spin activated, and made resonant with DNA or histone. Therefore we sought a structural site capable of electron transfer from the cell membrane. For this reason, membrane sphingomyelin, which contains the phosphocholine dipole along with fatty acid chains, was of interest.

BRIEF SUMMARY OF THE INVENTION

According to one aspect, the described invention provide an organometallic complex comprising a first lipid component comprising a carbonyl functional group, an alcohol functional group, or a combination thereof; a ruthenium component; a first amino acid component comprising a carbonyl functional group, a methyl functional group, or combination thereof; wherein the ruthenium component is associated with the first lipid component via carbonyl functional group, alcohol functional group, or combination thereof, of the first lipid component; wherein the ruthenium component is associated with the first amino acid component via carbonyl functional group, methyl functional group, or combination thereof, of the first amino acid; wherein the first lipid component, the ruthenium component and first amino acid component are in association to form a first sub complex; the organometallic complex further comprising a macromolecule component; the organometallic complex optionally further comprising a second lipid component comprising a methyl functional group, an alkene functional group, a carboxylic acid functional group, or a combination thereof; a metal component; a second amino acid component comprising a carboxylic acid functional group, an amine functional group, or a combination thereof; and a third amino acid component comprising an amine functional group; wherein the metal component is associated with the second lipid component via the methyl functional group of the second lipid component; wherein the metal component is associated with the second amino acid component via the amine functional group, carbonyl functional group, or combination thereof, of the second amino acid; wherein the third amino acid component is associated with the second lipid component via an association of the alkene functional group of the second lipid with the amine functional group of the third amino acid; wherein, when present, the second lipid component, second metal component, second amino acid component, and third amino acid component are in association to form a second sub complex; wherein, if the second sub complex is present, the first sub complex associates with the second sub complex via the metal component and the carbonyl functional group of the first amino acid to form a single larger complex; wherein the macromolecule component associates at least with the first sub complex.

According to one embodiment, the ruthenium component comprises elemental ruthenium, a ruthenium salt, or a combination thereof.

According to another embodiment, the first lipid component is a fatty acid component or a derivative thereof, a membrane lipid component or a derivative thereof, or a combination thereof.

According to another embodiment, the first lipid component is an amphipathic molecule having a hydrophilic region and a hydrophobic region, the hydrophobic region comprising one or more hydrocarbon tails between 2 and 24 carbons long and the hydrophilic region comprising a net charge of between 0 and −4 at a pH of 7.

According to another embodiment, the first lipid component is a sphingolipid.

According to another embodiment, the sphingolipid is a sphingomyelin.

According to another embodiment, the amino acid component comprises and amino acid or a derivative thereof.

According to another embodiment, the amino acid component comprises an N-formyl amino acid.

According to another embodiment, the amino acid component comprises N-formyl methionine.

According to another embodiment, the macromolecule component comprises a polypeptide chain having a molecular weight of at least 20 kilodaltons (kDa).

According to another embodiment, the polypeptide comprises an immunoglobulin or derivative thereof.

According to another embodiment, the second lipid component comprises a fatty acid component or a derivative thereof.

According to another embodiment, the fatty acid component comprises a hydrocarbon tail of between 2 and 24 carbons.

According to another embodiment, the fatty acid component comprises between 0 and 3 double bonds.

According to another embodiment, the fatty acid component comprises linoleic acid.

According to another embodiment, the metal component comprises a non-transition metal component.

According to another embodiment, the non-transition metal component comprises an elemental non-transition metal, a salt of a non-transition metal, or a combination thereof.

According to another embodiment, the non-transition metal comprises a zinc component.

According to another embodiment, the second amino acid component and third amino acid component comprise an amino acid or a derivative thereof.

According to another embodiment, the second amino acid comprises a polar non-charged amino acid.

According to another embodiment, the second amino acid component comprises threonine.

According to another embodiment, the third amino acid component comprises a positively charged amino acid.

According to another embodiment, the third amino acid component comprises arginine.

According to one aspect, the described invention provides a pharmaceutical composition comprising a therapeutic amount of the organometallic complex as described above, wherein the therapeutic amount is effective to have anti-tumor or anti-cancer effect, the anti-tumor or anti-cancer effect comprising cytotoxicity of tumor cells or cancer cells, inhibited growth of tumor cells or cancer cells, inhibited migration of tumor cells or cancer cells, or any combination of these effects.

According to one aspect, the described invention provides a method of treating a tumor comprising tumor cells characterized by uncontrolled growth, proliferation, or a combination thereof, in a mammal comprising the steps of (a) providing a therapeutic amount of the pharmaceutical composition according to claim 24; and (b) administering the therapeutic amount of the pharmaceutical composition to the mammal, wherein the therapeutic amount is effective: to reduce the number of tumor cells; to inhibit growth of the tumor cells, to inhibit migration of tumor cells, or any combination thereof.

According to one embodiment, the tumor cells comprise a population of stem cells characterized by the ability to self-renew the cells of the tumor.

According to one embodiment, the tumor cells comprise a population of cells comprising mutations in chromatin-regulating genes.

According to another embodiment, the tumor cells comprise a population of cells comprising a mutation in a histone deacetylase gene, a methyltransferase gene, or any combination thereof.

According to another embodiment, the tumor cells comprise a population of cells of epithelial origin.

According to another embodiment, the tumor cells comprise a population of breast tumor cells.

According to another embodiment, the tumor cells comprise a population of pancreatic tumor cells.

According to another embodiment, the administering is parentally, enterally, topically, or transdermally.

According to one aspect, the described invention provides n organometallic complex of Formula I:

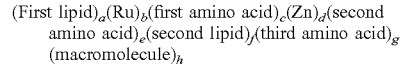

(First lipid)$_a$(Ru)$_b$(first amino acid)$_c$(Zn)$_d$(second amino acid)$_e$(second lipid)$_f$(third amino acid)$_g$(macromolecule)$_h$ wherein the first lipid component comprises a membrane lipid or a derivative thereof; the Ru signifies a ruthenium component; the first, second, and third amino acid components comprise an amino acid or a derivative thereof; the Zn signifies a zinc component; the second lipid component comprises a hydrocarbon chain of from 2 to twenty carbon atoms wherein at one end of the hydrocarbon chain (ω carbon) is a methyl group and at the other end (α carbon) is a carboxyl group; the macromolecule component comprises a polypeptide chain; wherein a, b, c, and h are at least 1; and d, e, f, and g are 0 or 1; wherein e, f, and g are 0 when d is 0, and g is 0 when f is 0; wherein the Ru component structurally associates the sphingomyelin component with the first amino acid component; the Zn component structurally associates the first amino acid component with one or more of the second amino acid component or fatty acid component; the third amino acid component is associated with the fatty acid component; the macromolecule component associates with one or more of the first lipid component, the Ru component, the first amino acid component, the Zn component, the second amino acid component, the third amino acid component, or the second lipid component.

According to one embodiment the ruthenium component is elemental ruthenium, or a ruthenium salt, selected from the group consisting of ruthenium chloride, ruthenium bromide, ruthenium iodide, ruthenium nitrate, ruthenium oxide, ruthenium sulfide, or a combination thereof.

According to another embodiment, the first lipid component comprises a membrane lipid or a derivative thereof.

According to another embodiment, the first lipid component comprises a sphingomyelin or a derivative thereof.

According to another embodiment, the first amino acid component comprises an N-formyl methionine or a derivative thereof.

According to another embodiment, the second lipid component comprises a fatty acid component comprising a hydrocarbon chain of from between 2 to 25 carbon atoms, wherein at one end of the hydrocarbon chain is a methyl group and at the other end is a carboxyl group, or a derivative thereof.

According to another embodiment, the fatty acid component is linoleic acid or a derivative thereof.

According to another embodiment, the macromolecule component is a polypeptide.

According to another embodiment, the macromolecule component comprises IgG or a derivative thereof.

DETAILED DESCRIPTION OF THE INVENTION

Glossary

Figure 1:
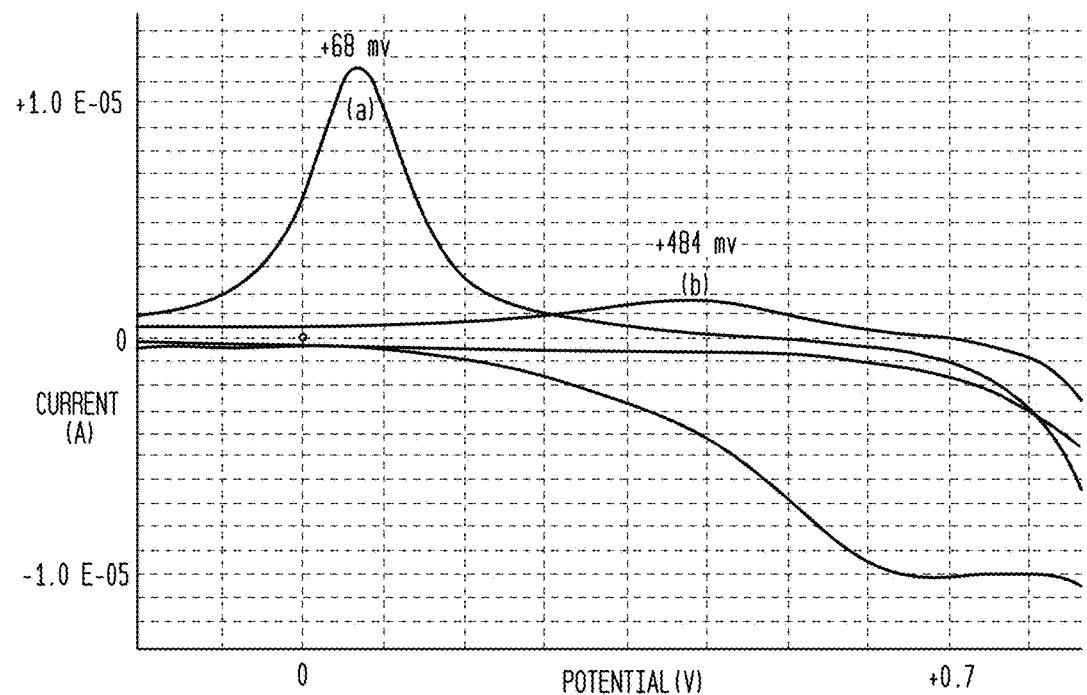
FIG. 1 shows voltammetry data for a sample of GML0001 ("Toroglobulin™") alone (a) and Toroglobulin™ with Histone IIS (b) (Calf Thymus-Histone IIS Sigma, Cat. No. H-6005) performed with an EG&G Parstat potentiostat using a gold working electrode, a Pt counter electrode, and a Ag/KCl reference electrode. The samples were purged with nitrogen for ten minutes prior to measurement. The vertical axis of the graph depicted in FIG. 1 represents current (A), and the horizontal axis of the graph in FIG. 1 represents voltage potential (V). The voltammetry measurement revealed a 416 mv electropositive peak shift of Toroglobulin™ in the presence of Histone IIS. The voltammetry peaks of Toroglobulin™ alone and Toroglobulin™ with Histone IIS are marked as (a) and (b), respectively, along the horizontal axis of the graph depicted in FIG. 1. The Toroglobulin™ current density (A), represented by the values on the vertical axis, is also notably diminished. This data shows that Histone IIS can as an electron acceptor, and that Toroglobulin™ can act as a histone reductase.

The term "3-d tunnel vortex configuration" as used herein refers to the cylindrical hollow shape assumed when the precursor hexagonal lattice is pinned with glycine solution.

The term "Abrikosov lattice" as used herein refers to the state of the vortices appearing in aligned patterns or arrays, manifesting the supercurrent (here 416 mv electron transfer) characteristic of superconductors.

The term "alloy" as used herein refers to a mixture of two or more elements, one of which must be a metal, to form a macroscopically homogeneous metallic product.

The terms "amino acid component", "amino acid residue", "amino acid" or "residue" are used interchangeably to refer to an amino acid (meaning an organic acid in which one of the hydrogen atoms on a carbon atom has been replaced by $NH_2$) that is incorporated into the complex of the described invention, including, but not limited to, a naturally occurring amino acid and known analogs of natural amino acids that can function in a similar manner as naturally occurring amino acids. When utilized to denote an amino acid, the abbreviations for amino acids are those abbreviations which are conventionally used: A=Ala=Alanine; R=Arg=Arginine; N=Asn=Asparagine; D=Asp=Aspartic acid; C=Cys=Cysteine; Q=Gln=Glutamine; E=Glu=Glutamic acid; G=Gly=Glycine; H=His=Histidine; I=Ile=Isoleucine; L=Leu=Leucine; K=Lys=Lysine; M=Met=Methionine; F=Phe=Phenylalanine; P=Pro=Proline; S=Ser=Serine; T=Thr=Threonine; W=Trp=Tryptophan; Y=Tyr=Tyrosine; V=Val=Valine. The amino acid may be an L- or D-amino acid. An amino acid may be replaced by a synthetic amino acid. When the complex comprises two amino acid residues, the two amino acids are the same amino acid or two different amino acids.

The term "anionic ligand" as used herein refers to a monoatomic or polyatomic species capable of bonding having one or more elementary charges of an electron and is therefore negatively charged.

The term "antioxidant" as used herein refers to an agent that inhibits oxidation that can neutralize the oxidant effect of free radicals and other substances. An oxidant is the substance that is reduced (i.e., gains electrons) and therefore oxidizes the other component of an oxidation-reduction system (which therefore loses electrons).

The term "associate" and its various grammatical forms as used herein refers to joining, connecting, or combining to, either directly, indirectly, actively, inactively, inertly, non-inertly, completely or incompletely. Associated includes "connected."

The terms "bond" or "chemical bonds" or "bonded" are used interchangeably and refer to an attraction between atoms, alone or part of a larger molecule, that enables the formation of larger compounds. The term bond is inclusive of all different strengths and types, including covalent bonds, ionic bonds, halogen bonding, hydrogen bonds, van der waals forces, and hydrophobic effects.

The term "capacitor" as used herein refers to a component, which has capacitance, meaning the ability to store electronic charge between conductors which are separated by a dielectric material when a potential difference exists between the conductors.

The term "cationic ligand" as used herein refers to a monoatomic or polyatomic species capable of bonding having one or more elementary charges of a proton, and is therefore positively charged.

The term "charge transfer" as used herein refers to the transfer of electric charge, for example transfer of electrons or protons, from one entity to another, or from one location to another, within the same entity.

The term "cis-" as used herein refers to a molecular structure in which two particular atoms or groups of atoms lie on the same side of a given plane in the molecule. In particular, the term "cis-" with reference to a carbon-carbon double bond refers to an isomer in which substituents at opposite ends of the carbon-carbon double bond are on the same side of the carbon-carbon double bond.

The term "condition," as used herein, refers to a variety of health states and is meant to include disorders or diseases caused by any underlying mechanism or disorder.

The term "connected" as used herein refers to is being joined, linked, or fastened together in close association. For example, in the context of a chemical compound the term "connected to" refers to the attraction or connection between two atoms or molecules via direct or indirect chemical bonds.

The term "coordinate bond" or "coordinate covalent bond" as used herein refers to a covalent bond consisting of a pair of electrons donated by only one of the two atoms it joins. Coordinate bonds are weaker than covalent bonds. A covalent bond is formed by the sharing of pairs of electrons between atoms.

The term "coordination alloy" as used herein refers to an alloy containing one or more coordinate bonds joining one or more of its constituent chemical entities.

The term "coordination entity", "coordination complex", "complex" or "complex entity" as used herein refers to a molecular entity formed in a crystal and ligand field produced by a metal and a second molecule. The strength of the complex is derived from the stability of the crystal symmetry and the delocalization and sharing of charges. A coordination complex may or may not be covalent. There are many covalent coordination complexes in nature, including, without limitation, vitamin B12, hemoglobin, chlorophyll, the nitrogenase enzyme, and the cytochromes.

The term "derivative" as used herein means a compound that may be produced from another compound of similar structure in one or more steps. A "derivative" or "derivatives" of a component or a compound retains at least a degree of the desired function of the component or compound. Accordingly, an alternate term for "derivative" may be "functional derivative." Derivatives can include chemical modifications, such as akylation, acylation, carbamylation, iodination or any modification that derivatizes the component or compound. Examples of such derivatized molecules include, for example, those molecules in which free amino groups have been derivatized to form amine hydrochlorides, p-toluene sulfonyl groups, carbobenzoxy groups, t-butyloxycarbonyl groups, chloroacetyl groups or formal groups. Free carboxyl groups can be derivatized to form salts, esters, amides, or hydrazides. Free hydroxyl groups can be derivatized to form O-acyl or O-alkyl derivatives.

The term "depolarization" as used herein refers to the removal, decrease or prevention of polarization, meaning the separation of electric charges into a positive and negative pole. Depolarization includes a removal or decrease in charge separation of an electric dipole, or separation of $+\frac{1}{2}$ and $-\frac{1}{2}$ spin states of a magnetic dipole.

The term "detoxification" as used herein refers to a lowering of a level of free radicals such that their toxic effects are reduced. Detoxification includes, but is not limited to, depolarization of free radicals.

The terms "dipole" as used herein refers to a state of separation of two opposite or opposing attributes, magnitudes or the like. A dipole can be an electric dipole or a magnetic dipole. The term "electric dipole" used herein refers to a state of separation of two opposite charges of equal magnitude separated by a very small distance. A dipole is characterized by a vector quantity, known as the dipole moment, that points from the negative charge towards the positive charge. The dipole moment is the product of the magnitude of one of the charges and the distance between the centers of the charges. The term "magnetic dipole" as used herein refers to the state of separation of two equal magnetic poles with opposite polarity separated by a distance. The term "magnetic spin dipole" as used herein refers to the state of separation of $+\frac{1}{2}$ and $-\frac{1}{2}$ spin states along an applied magnetic field.

The term "discharge" as used herein refers to the depletion or removal of stored electric charge.

The terms "disease" or "disorder" as used herein refer to an impairment of health or a condition of abnormal functioning.

The term "electronegative" as used herein refers to the ability of a chemical entity to attract electrons or electron density toward itself.

The term "electropositive" as used herein refers to the ability of a chemical entity to donate electrons or electron density away from itself.

The term "extracellular matrix" refers to the complex network of polysaccharides (such as glycosaminoglycans) and proteins (such as collagen) secreted by cells that serves as a structural element in tissues and influences development and physiology.

The term "free radical" as used herein refers to a highly reactive and usually short-lived molecular fragment with one or more unpaired electrons. Free radicals are highly chemically reactive molecules. Because a free radical needs to extract a second electron from a neighboring molecule to pair its single electron, it often reacts with other molecules, which initiates the formation of many more free radical species in a self-propagating chain reaction. This ability to be self-propagating makes free radicals highly toxic to living organisms. Oxidative injury may lead to widespread biochemical damage within the cell. The molecular mechanisms responsible for this damage are complex. For example, free radicals may damage intracellular macromolecules, such as nucleic acids (e.g., DNA and RNA), proteins, and lipids. Free radical damage to cellular proteins may lead to loss of enzymatic function and cell death. Free radical damage to DNA may cause problems in replication or transcription, leading to cell death or uncontrolled cell growth. Free radical damage to cell membrane lipids may cause the damaged membranes to lose their ability to transport oxygen, nutrients or water to cells.

There are many types of free radicals but most common radicals in biological systems are derived from oxygen, collectively known as reactive oxygen species (ROS). ROS comprise oxygen derived small molecules such as oxygen radicals: superoxide, hydroxyl, peroxyl, and alkoxyl; or the nonradicals: hypochlorous acid, ozone, singlet oxygen, and hydrogen peroxide. Oxygen ($O_2$) has two unpaired electrons in separate orbitals in its outer shell. Sequential reduction of molecular oxygen (equivalent to sequential addition of electrons) leads to the formation of a group of reactive oxygen species: superoxide anion ($O_2.^-$), peroxide ($O_2.^{-2}$) and hydroxyl radical (.OH). Another radical derived from oxygen is singlet oxygen ($^1O_2$), an excited form of oxygen in which one of the electrons is present in a higher energy level upon absorption of energy.

The terms "hyperfine splitting" and "superhyperfine splitting" as used herein refer to the splitting of spectrographic peaks resulting from spin-spin coupling between nuclei of atoms in the region. These interactions are evidence of covalency. The multiplicity of six interactions constitutes a super-hyperfine interaction.

The term "immunoglobulin" (Ig) as used herein refers to a class of structurally related proteins, each consisting of two pairs of polypeptide chains, one pair of light (L) (low molecular weight) chains (κ or λ), and one pair of heavy (H) chains (γ, α, μ, δ, and ε), usually all four linked together by disulfide bonds. On the basis of the structural and antigenic properties of the H chains, Ig's are classified (in order of relative amounts present in normal human serum) as IgG, IgA, IgM, IgD, and IgE. Each class of H chain can associate with either κ or λ L chains. Subclasses of Ig's are based on differences in the H chains, and are referred to as $IgG_1$, etc.

When split by papain, IgG yields three pieces: the Fc piece, consisting of the C-terminal portion of the H chains, with no antibody activity but capable of fixing complement, and crystallizable; and two identical Fab pieces, each carrying an antigen-binding site and each consisting of an L chain bound to the remainder of an H chain.

All L chains are divided into a region of variable sequence ($V_L$) and one of constant sequence ($C_L$), each comprising about half the length of the L chain. The constant regions of all human L chains of the same type (κ or λ) are identical except for a single amino acid substitution, under genetic controls. H chains are similarly divided, although the $V_H$ region, while similar in length to the $V_L$ region, is only one-third or one-fourth the length of the $C_H$ region. Binding sites are a combination of $V_L$ and $V_H$ protein regions. The large number of possible combinations of L and H chains make up the "libraries" of antibodies of each individual.

The term Ig includes, without limitation, naturally occurring and non-naturally occurring IgGs, polyclonal IgGs, monoclonal IgGs, chimeric IgGs, wholly synthetic IgGs, and fragments thereof.

The term "impedance", "bioimpedance", "electrical impedance" or "electrochemical impedance" as used herein refers to frequency dependent resistance derived from three components of an AC circuit: direct current (DC) resistance; capacitive reactance (or capacitance); and inductive reactance (or inductance). Impedance is the opposition to the flow of alternating current through a conductor, and is described by a relation between voltage and current in a system. Impedance is defined as the ratio of incremental change in voltage to the resulting current (or vice versa) across an electrochemical cell or an electrical circuit. Impedance has two components: resistance, which is a real number, and reactance, an imaginary number. It is usually measured by applying a sinusoidally varying AC potential to an electrochemical cell and then measuring the current through the cell as a function of frequency. The terms "capacitance" and "capacitive resistance" are used interchangeably to mean resistance that is produced by storing charge on a surface at an energy expense producing a retardation of voltage flow. The terms "inductance" and "inductive resistance" are used interchangeably to mean resistance that is produced by storing energy in a magnetic field in bulk space at an energy expense producing a retardation of current flow. These two retardation effects are combined in a process and representation called the "phase angle" which is the angular summation of the two waves or pulses of voltage and current.

The term "insulator" as used herein refers to a material that prevents the conduction of energy, or a material that has a sufficiently high resistance to the passage of electric current, so that current flow through it is minimal or negligible.

The term "isolated" is used herein to refer to material, such as, but not limited to, a nucleic acid, peptide, polypeptide, or protein, which is: (1) substantially or essentially free from components that normally accompany or interact with it as found in its naturally occurring environment. The terms "substantially free" or "essentially free" are used herein to refer to considerably or significantly free of, or more than about 75%, 80%, 85%, 90%, 95%, 96%, 97%, 98%, 99%, or more than about 99% free of. The isolated material optionally comprises material not found with the material in its natural environment; or (2) if the material is in its natural environment, the material has been synthetically (non-naturally) altered by deliberate human intervention to a composition and/or placed at a location in the cell (e.g., genome or subcellular organelle) not native to a material found in that environment. The alteration to yield the synthetic material may be performed on the material within, or removed, from its natural state.

The term "Lewis acid" as used herein refers to any molecule (called an electrophile) that can combine with another molecule or ion by forming a covalent bond with two electrons from the second molecule or ion. A Lewis acid is thus an electron acceptor.

The term "Lewis base" as used herein refers to a substance (also called a nucleophile) that forms a covalent bond by donating a pair of electrons, with neutralization resulting from reaction between the base and the acid with formation of a coordinate covalent bond. A Lewis base is therefore an electron donor.

The term "ligand" as used herein refers to a chemical entity or species, an atom, a molecule, or an ion, that is bonded to the central metal atom of a coordinate complex via coordinate covalent bonds.

The term "lipid" as used herein refers to a class of organic compounds that are relatively insoluble in water, but tend to dissolve in non-polar organic solvents, related to fatty acids, esters, fatty alcohols, sterols, waxes, etc., and utilizable by an animal organism.

The term "liquid crystal" as used herein refers to matter that has properties between those of a conventional liquid and those of a solid crystal.

The term "lone pair" as used herein refers to two paired electrons localized in the valence shell, the highest molecular orbitals, on a single atom.

The term "matrix" as used herein refers to a medium or structure in which or on which something is embedded.

The term "mixture" refers to the result of combining multiple entities into one or more products, or the result of such a combination.

The term "non-transition metals" refers to metals that are not transition metals. Non-transition metals include the alkali metals found in group 1 of the periodic table (e.g., lithium, sodium, potassium, rubidium, cesium, francium); alkaline earth metals found the second group of the periodic table (beryllium, magnesium, calcium, strontium, barium, radium); and other metals located in groups 13, 14 and 15 of the periodic table (e.g., aluminum, gallium, indium, tin, thallium, lead and bismuth).

The term "organified" as used herein refers to a state of being bonded to an organyl group by a covalent or coordination covalent bond.

The term "organometallic complex" as used herein refers to a coordination entity having one or more coordination covalent bonds between one or more metal atoms and one or more carbon atoms of an organyl group.

The term "organometallic compound" as used herein refers to a compound having one or more bonds between one or more metal atoms and one or more carbon atoms of an organyl group.

The term "organyl" as used herein refers to containing any organic substituent group, regardless of functional type.

The term "oscillation" as used herein refers to a periodic variation around a set point.

The term "oxidation" as used herein refers to the loss of one or more electrons or a concomitant increase in the oxidation state. The term "oxidized form" as used herein refers to a form of a chemical entity which has undergone oxidation, i.e. lost one or more electrons.

The term "oxidation state" as used herein refers to the degree of oxidation in a chemical entity.

The term "oxidative stress" as used herein refers to a redox imbalance within the cell usually due to increased reactive oxygen species (ROS) and decreased antioxidants.

The term "peroxide depolarization" and "denaturation" as used herein refer to a phase angle reversal of the polarity of the inductance spike, which represents a plot of the inductance field discharge and the denaturation of the peroxide in the electric double layer.

The term "peritectic point" as used herein refers to a point on a phase diagram where a reaction takes place between a previously precipitated phase and the liquid to produce a new solid phase.

The term "pharmaceutically acceptable carrier" as used herein refers to a compatible solid or liquid filler, diluent or encapsulating substance which is/are suitable for administration to a human or other vertebrate animal. The components of the pharmaceutical compositions also are capable of being commingled in a manner such that there is no interaction which would substantially impair the desired pharmaceutical efficiency. As used herein the phrase "pharmaceutically acceptable carrier" refers to any substantially non-toxic carrier useable for formulation and administration of the composition of the described invention in which the organometallic complex of the described invention will remain stable and bioavailable.

The term "pharmaceutical composition" is used herein to refer to a composition that is employed to prevent, reduce in intensity, cure or otherwise treat a target condition or disease.

The term "pinning" refers to local coupling, with energy interaction and steric ordering.

The term "polarity" as used herein refers to possession or manifestation of two opposite or opposite attributes, magnitudes, or the like, for example, electrical or magnetic polarity. The term "electrical polarity" as used herein refers to the property of having an excess or a deficiency of electrons. An excess of electrons produces a negative polarity and a deficiency of electrons produces a positive polarity. This determines the flow of electric current as electrons move from a point with an excess of electrons towards a point deficient in electrons. The term "magnetic spin polarity" as used herein refers to the presence of two regions representing opposite spin states.

The term "potential" or "standard potential" as used herein refers to work required to bring a unit charge from a reference point to a specific point within an electric field. The term "electropositive potential" or "electropositive standard potential" or "oxidation potential" as used herein refers to a measure of the tendency to donate electrons, and thereby be oxidized. The term "electronegative potential" or "electronegative standard potential" or "reduction potential" as used herein refers to a measure of the tendency to attract electrons, and thereby be reduced.

The term "potential difference" as used herein refers to a difference between the potentials of two points in an electric field.

The term "potential gradient" as used herein refers to a rate of change of potential with respect to distance in the direction of the greatest charge.

The term "precession" as used herein refers to a change in orientation of the rotational axis of a rotating body, analogous to the wobble of a spinning top. The term "Larmour precession" refers to the precession of an electron subjected to a torque induced by an applied magnetic field around the axis of the applied magnetic field. The terms "Larmour frequency $\omega L$" or "precessional frequency" are used interchangeably herein to refer to the angular frequency or the number of times per second an electron precesses in a complete circle around the field axis.

The term "Reactance (X)" as used herein refers to a current travelling through a capacitor. A higher reactance has a higher effective resistance to alternating current. Like resistance, its value is in Ohms, but it depends on the applied frequency, and is described by the relation: Reactance (Ohms)=$1/(2 \times r \times$Frequency (Hz)$\times$Capacitance (Farads)). When a current is passing through a purely resistive circuit, the voltage recorded across the resistor will coincide exactly with the timing, or phase, of the applied alternating current. However, when current flows across a capacitor, the voltage recorded across it lags behind the applied current, because of back and forth flow of current requiring alternating charging and discharging of the plates of the capacitor. In terms of a sine wave which has 360° in a full cycle, the lag is one quarter of a cycle, i.e., 90°.

The term "reduction" as used herein refers to a gain of electrons or a concomitant decrease in the oxidation state. The term "reduced form" as used herein refers to a form of a chemical entity which has undergone reduction, i.e. gained one or more electrons.

The term "resistance (R)" as used herein refers to a measure of the extent to which an element opposes the flow of electrons or, in aqueous solution as in living tissue, the flow of ions among its cells. The three fundamental properties governing the flow of electricity are "voltage", "current" and "resistance". Voltage is the pressure exerted on a stream of charged particles moving down a wire or through an ionized salt solution. Current is the amount of charge flowing per unit time. Resistance is the ease or difficulty with which the charged particles can flow. Voltage, current and resistance are related by Ohm's law: V (voltage, Volts)=I (current, Amps)$\times$R (resistance, Ohms ($\Omega$)).

The term "semiconductor" as used herein refers to a material whose conductivity lies between that of an electrical conductor, such as a metal, and an insulator.

The term "solid state" as used herein refers to consisting of, pertaining to, characterized of, or arising from, matter whose state of matter is solid. The function usually depends on electrical, magnetic and/or optical phenomena occurring within the solid.

The term "spin" as used herein refers to a rotation of a subatomic charged particle, such as electron or nucleus around its axis. Spins result in generation of a magnetic field that is associated with a small quantity of angular momentum leading to a magnetic moment intrinsic to a charge carrier (such as an electron).

The terms "spin coupling" or "spin-spin interaction" as used herein refer to an interaction between the magnetic moment of a spinning charged particle (such as an electron or atomic nucleus) with the magnetic moment of another in its vicinity. In case of electron systems, spin-spin coupling results in the splitting of electron spin resonance lines, a phenomenon known as hyperfine splitting or hyperfine interaction.

The terms "spin moment" or "spin vector" are used interchangeably to refer to the magnetic moment, a vector quantity, induced by the circulating electric current resulting from the negative charge carried by a spinning electron.

The term "spin polarization" or "spin magnetism" as used herein refers to the degree to which the intrinsic spin moment is aligned with a given direction. When an atom or molecule has an even number of electrons, electron spins pair off in atomic or molecular orbitals so that virtually no net spin magnetism is exhibited; such material is said to be "diamagnetic". However, when an atom or molecule has an odd number of electrons, complete pairing is not possible and the material is said to be "paramagnetic".

The term "spin state" as used herein refers to the projection of the spin moment (spin vector) μS along an applied magnetic field $H_0$. When subjected to a magnetic field, an electron with magnetic moment $\mu_S$ experiences a torque that tends to align the magnetic moment with the magnetic field. The energy of the system depends upon the projection of the spin vector along $H_0$. Quantum theory stipulates that only two values are permitted for an electron, which means that the electron magnetic moment can only assume two projections or spin states onto the applied field: the "+½ spin state", when the electron's magnetic moment $\mu_S$ is aligned with the direction of the applied magnetic field $H_0$; and the "−½ spin state", when the electron's magnetic moment $\mu_S$ is aligned opposed to the direction of $H_0$. Consequently, the ensemble of energy levels also reduce to two values, designated as $E_+$, a lower energy level corresponding to the +½ spin state (aligned with the direction of the applied magnetic field) and $E_-$, a higher energy level corresponding to the −½ spin state (opposed to the direction of the applied magnetic field). Because the +½ spin state is of slightly lower energy, in a large population of electrons, slightly more than half of the electrons will occupy this state, while slightly less than half will occupy the −½ spin state. The slight excess of the electron spin in the direction of the magnetic field constitutes a slight net magnetization of the material, a phenomenon known as spin polarization or spin magnetism. The difference in energy between the two spin states increases with increasing strength of the magnetic field $H_0$. Higher the strength of $H_0$, more is the net magnetization or the spin polarization, i.e. more number of electrons will occupy the +½ state as compared to the −½ state.

The terms "spin resonance" or "electron spin resonance (ESR)" are used interchangeably to refer to a condition in which an electron absorbs energy in flipping from a lower energy level to a higher energy level when exposed to an electromagnetic radiation of a frequency that matches the precessional frequency (Larmour frequency) of the electron. In this resonance condition, an electron of a lower energy +½ spin state (aligned with the applied magnetic field) will transition or flip to the higher energy −½ spin state (opposed to the applied magnetic field). In doing so, the electron absorbs radiation at this resonance frequency, $\omega_A = \omega_L$.

The term "spin polarized current" as used herein refers to a current with more electrons of either spin.

The term "spin transfer" as used herein refers to the following. By passing a current through a thick magnetic layer, one can produce a spin-polarized current. If a spin-polarized current is directed into a magnetic layer, angular momentum can be transferred to the layer changing its orientation. This can be used to excite oscillations or to flip the orientation of the magnet.

The term "superconductor" as used herein refers to an element, alloy, compound or other material which exhibits superconductivity, meaning the flow of current with a complete, or nearly complete, disappearance of all electrical resistance.

The terms "therapeutic amount", "therapeutic effective amount" or an "amount effective" of one or more therapeutic agents is an amount that is sufficient to provide the intended beneficial effect. Combined with the teachings provided herein, by choosing among the various active compounds and weighing factors such as potency, relative bioavailability, patient body weight, severity of adverse side-effects and preferred mode of administration, an effective prophylactic or therapeutic treatment regimen may be planned which does not cause substantial toxicity and yet is effective to treat the particular subject. A therapeutic effective amount for any particular application may vary depending on such factors as the disease or condition being treated, the particular therapeutic agent being administered, the size of the subject, or the severity of the disease or condition. One of ordinary skill in the art may determine empirically the effective amount of a particular therapeutic agent without necessitating undue experimentation. It is preferred generally that a maximum tolerated dose (MTD) be used, that is, the highest dose that will produce the desired effect without unacceptable toxicity according to some medical judgment. However, dosage levels are based on a variety of factors, including the type of injury, the age, weight, sex, medical condition of the patient, the severity of the condition, the route of administration, and the particular therapeutic agent employed. Thus the dosage regimen may vary widely, but can be determined routinely by a surgeon using standard methods. "Dose" and "dosage" are used interchangeably herein.

The term "therapeutic effect" as used herein refers to a consequence of treatment, the results of which are judged to be desirable and beneficial. A therapeutic effect may include, directly or indirectly, the arrest, reduction, or elimination of a disease manifestation. A therapeutic effect may also include, directly or indirectly, the arrest reduction or elimination of the progression of a disease manifestation.

The term "trans-" as used herein refers to a molecular structure in which two particular atoms or groups of atoms lie on the opposite side of a given plane in the molecule. In particular, the term "trans-" with reference to a carbon-carbon double bond refers to an isomer in which substituents at opposite ends of the carbon-carbon double bond are on the opposite side of the carbon-carbon double bond.

The term "transition metal" or "transition element" as used herein refers to an element whose atom has an incomplete d sub-shell, or which can give rise to cations with an incomplete d sub-shell generally in groups 3 through 12 of the periodic table. Scandium and zinc, while located in this part of the periodic table are not transition metals; i.e. they do not meet the requirements of the definition. For example, scandium has the electronic structure [Ar] $3d^1$ $4s^2$. When it forms ions, it always loses the 3 outer electrons and ends up with an argon structure. The $Sc^{3+}$ ion has no d electrons and so doesn't meet the definition of a transition metal. Zinc has the electronic structure [Ar] $3d^{10} 4s^2$. When it forms ions, it always loses the two 4s electrons to give a 2+ ion with the electronic structure [Ar] $3d^{10}$. The zinc ion has full d levels and doesn't meet the definition of a transition metal.

The term "valence" as used herein refers to the quality that determines the number of chemical bonds an atom can form. Electrons in an atom's outermost shell are the valence electrons.

The term "vortex" as used herein refers to a specific phase state that can have diverse morphologies, such as hurricane, whirlpool, or black hole, but has a unique funnel geometry designed for energy focus.

The term "vortex pinning" as used herein refers to a dynamic phase change involving the localization and maturation of a vortex with a surface or a matrix. Pinning involves an exchange of vortex energy with the matrix or the surface. Glycine is one example of a chemical matrix suitable for pinning certain vortices.

Organo Metallic Complexes

The described invention provides a complex comprising ruthenium and sphingomyelin, with the option of added zinc. The core of ruthenium and sphingomyelin, with additional zinc, allows the synthesis of numerous other compounds through an alkylzinc bridge. [Ohashi, M, Matsubara, K, Suzuki, H, Ruthenium polyhydrido clusters having a bridging alkylzinc group, Organometallics, 26 (9) 2230-2339, 2007.] These compounds can convert to chemotherapy agents through further connections with contributing organic ligands.

According to one aspect, the described invention comprises an organometallic complex comprising one or more transition metal components and lipid components.

Transition Metal Component

According to some embodiments, the described invention comprises a transition metal component comprising an element whose atom has an incomplete d sub-shell, or which can give rise to cations with an incomplete d sub-shell. According to some embodiments, the transition metal component comprises the elemental form or salt form of one or more of Titanium, Vanadium, Chromium, Manganese, Iron, Cobalt, Nickel, Copper, Yttrium, Zirconium, Niobium, Molybdenum, Technetium, Ruthenium, Rhodium, Hafnium, Tantalum, Tungsten, Rhenium, Osmium, Iridium, Platinum, Rutherfordium, Dubnium, Seaborgium, Bohrium, Hassium, Meitnerium, Darmstadtium, Roentgenium, or Copernicium. According to some embodiments, the transition metal component comprises the element ruthenium.

Ruthenium Component

According to some embodiments, the transition metal component comprises a ruthenium component. Ruthenium is a transition metal of group 8 of the periodic table having an electronic configuration of 1s2 2s2p6 3s2p6d10 4s2p6d7 5s1. According to some embodiments, the ruthenium component is selected from elemental ruthenium or a ruthenium salt. According to some embodiments, the ruthenium component is in the form of elemental ruthenium. According some embodiments, the ruthenium component is in the form of a ruthenium salt. According to some embodiments, the ruthenium component in the form of a salt comprises one or more of ruthenium acetate, ruthenium acetylacetonate, ruthenium ammonium chloride, ruthenium ammonium nitrate, ruthenium bromide, ruthenium chloride, ruthenium diamine nitrite, ruthenium diamylamine nitrite, ruthenium dibromide, ruthenium difluoride, ruthenium dioxide, ruthenium dipyridine nitrite, ruthenium ethylenediamine nitrite, ruthenium iodide, ruthenium monoxide, ruthenium nitrate, ruthenium oxalate, ruthenium oxide, ruthenium sulfate, ruthenium sulfide, ruthenium tetramine dichloride, ruthenium potassium bromide, ruthenium potassium chloride, ruthenium sodium bromide, and ruthenium sodium chloride. According to some embodiments, the ruthenium salt is ruthenium chloride, ruthenium bromide, ruthenium iodide, ruthenium nitrate, ruthenium oxide or ruthenium sulfide. According to some embodiments, the ruthenium salt is ruthenium chloride.

Lipid Component

According to some embodiments, the described invention comprises a lipid component.

Fatty Acid Component

According to some embodiments of the described invention, the lipid component comprises a fatty acid. Fatty acids are categorized and named based, in part, on the number of carbon atoms present. Those carbon atoms are numbered starting at the carboxy terminal end:

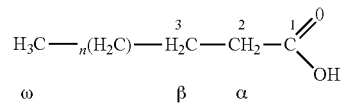

Carbon atoms $C_2$ and $C_3$ often are referred to as $\alpha$ and $\beta$, respectively. The methyl carbon at the distal end of the chain is called the w carbon.

According to some embodiments, the fatty acid component comprises a $C_2$ to $C_{24}$ hydrocarbon chain. According to some embodiments, the fatty acid component comprises a $C_2$ hydrocarbon chain, a $C_3$ hydrocarbon chain, a $C_4$ hydrocarbon chain, a $C_5$ hydrocarbon chain, a $C_6$ hydrocarbon chain, a $C_7$ hydrocarbon chain, a $C_8$ hydrocarbon chain, a $C_9$ hydrocarbon chain, a $C_{10}$ hydrocarbon chain, a $C_{11}$ hydrocarbon chain, a $C_{12}$ hydrocarbon chain, a $C_{13}$ hydrocarbon chain, a $C_{14}$ hydrocarbon chain, a $C_{15}$ hydrocarbon chain, a $C_{16}$ hydrocarbon chain, a $C_{17}$ hydrocarbon chain, a $C_{18}$ hydrocarbon chain, a $C_{19}$ hydrocarbon chain, a $C_{20}$ hydrocarbon chain, a $C_{21}$ hydrocarbon chain, a $C_{22}$ hydrocarbon chain, a $C_{23}$ hydrocarbon chain, a $C_{24}$ hydrocarbon chain.

According to some embodiments, the fatty acid component is saturated, meaning it contains no double bonds in the hydrocarbon chain. According to some embodiments, the fatty acid component is unsaturated, meaning it contains at least one double bond in the hydrocarbon chain. The position of a double bond may be represented by the symbol A followed by a superscript number. According to some embodiments, the fatty acid component comprises one or more double bonds. According to some embodiments, the fatty acids component comprises two or more double bonds. According to some embodiments, the fatty acids component comprises three or more double bonds. According to some embodiments, the fatty acids component comprises four or more double bonds. According to some embodiments, the fatty acids component comprises five or more double bonds. According to some embodiments, the fatty acids component comprises six or more double bonds. According to some embodiments, the fatty acids component comprises seven or more double bonds. According to some embodiments, the fatty acids component comprises eight or more double bonds. According to some embodiments, the fatty acids component comprises nine or more double bonds. According to some embodiments, the fatty acids component comprises ten or more double bonds.

According to some embodiments, the fatty acid component comprises a hydrocarbon tail with one or more cis-double bonds. According to some embodiments, the fatty acid component comprises a hydrocarbon tail with one or more trans-double bonds. According to some embodiments, the fatty acid component comprises hydrocarbons having two or more double bonds being separated by one or more single bonds.

According to some embodiments the fatty acid component comprises two cis-double bonds, two trans-double bonds, or one cis- and one trans-double bond. According to some embodiments the fatty acid component comprises double bonds trans-10, cis-12 (i.e. a trans-double bond between carbons 10 and 11, and a cis-double bond between carbons 12 and 13 from the carboxylic acid), cis-10 trans-12, cis-10 trans-12, or trans-10 trans-12. According to some embodiments the fatty acid component comprises double bonds cis-9 trans-11, trans-9 cis-11, cis-9 cis-11, or trans-9 trans-11. According to some embodiments the fatty acid component has double bonds cis-9 cis-12, cis-9 trans-12, trans-9 cis-12, or trans-9 trans-12. According to some embodiments the fatty acid component comprises a single double bond that is either cis- or trans-, that is located at $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, or $C_{23}$. According to some embodiments the fatty acid component will have no double bond. According to some embodiments the fatty acid component has two or more double bonds with no single bond in between.

According to some embodiments, the fatty acid component comprises one or more of:

| Common name | Systematic name | Structural Formula |
| --- | --- | --- |
| Propionic acid | Propanoic acid | $CH_3CH_2COOH$ C3:0 |
| Butyric acid | Butanoic acid | $CH_3(CH_2)_2COOH$ C4:0 |
| Valeric acid | Pentanoic acid | $CH_3(CH_2)_3COOH$ C5:0 |
| Caproic acid | Hexanoic acid | $CH_3(CH_2)_4COOH$ C6:0 |
| Enanthic acid | Heptanoic acid | $CH_3(CH_2)_5COOH$ C7:0 |
| Caprylic acid | Octanoic acid | $CH_3(CH_2)_6COOH$ C8:0 |
| Pelargonic acid | Nonanoic acid | $CH_3(CH_2)_7COOH$ C9:0 |
| Capric acid | Decanoic acid | $CH_3(CH_2)_8COOH$ C10:0 |
| Undecylic acid | Undecanoic acid | $CH_3(CH_2)_9COOH$ C11:0 |
| Lauric acid | Dodecanoic acid | $CH_3(CH_2)_{10}COOH$ C12:0 |
| Tridecylic acid | Tridecanoic acid | $CH_3(CH_2)_{11}COOH$ C13:0 |
| Myristic acid | Tetradecanoic acid | $CH_3(CH_2)_{12}COOH$ C14:0 |
| Pentadecylic acid | Pentadecanoic acid | $CH_3(CH_2)_{13}COOH$ C15:0 |
| Palmitic acid | Hexadecanoic acid | $CH_3(CH_2)_{14}COOH$ C16:0 |
| Margaric acid | Heptadecanoic acid | $CH_3(CH_2)_{15}COOH$ C17:0 |
| Stearic acid | Octadecanoic acid | $CH_3(CH_2)_{16}COOH$ C18:0 |
| Nonadecylic acid | Nonadecanoic acid | $CH_3(CH_2)_{17}COOH$ C19:0 |
| Arachidic acid | Eicosanoic acid | $CH_3(CH_2)_{18}COOH$ C20:0 |
| Heneicosylic acid | Heneicosanoic acid | $CH_3(CH_2)_{19}COOH$ C21:0 |
| Behenic acid | Docosanoic acid | $CH_3(CH_2)_{20}COOH$ C22:0 |
| Tricosylic acid | Tricosanoic acid | $CH_3(CH_2)_{21}COOH$ C23:0 |
| Lignoceric acid | Tetracosanoic acid | $CH_3(CH_2)_{22}COOH$ C24:0 |
| Pentacosylic acid | Pentacosanoic acid | $CH_3(CH_2)_{23}COOH$ C25:0 |
| Cerotic acid | Hexacosanoic acid | $CH_3(CH_2)_{24}COOH$ C26:0 |
| Heptacosylic acid | Heptacosanoic acid | $CH_3(CH_2)_{25}COOH$ C27:0 |
| Montanic acid | Octacosanoic acid | $CH_3(CH_2)_{26}COOH$ C28:0 |
| Nonacosylic acid | Nonacosanoic acid | $CH_3(CH_2)_{27}COOH$ C29:0 |
| Melissic acid | Triacontanoic acid | $CH_3(CH_2)_{28}COOH$ C30:0 |
| Henatriacontylic acid | Henatriacontanoic acid | $CH_3(CH_2)_{29}COOH$ C31:0 |
| Lacceroic acid | Dotriacontanoic acid | $CH_3(CH_2)_{30}COOH$ C32:0 |
| Psyllic acid | Tritriacontanoic acid | $CH_3(CH_2)_{31}COOH$ C33:0 |
| Geddic acid | Tetratriacontanoic acid | $CH_3(CH_2)_{32}COOH$ C34:0 |
| Ceroplastic acid | Pentatriacontanoic acid | $CH_3(CH_2)_{33}COOH$ C35:0 |
| Hexatriacontylic acid | Hexatriacontanoic acid | $CH_3(CH_2)_{34}COOH$ C36:0 |
| Heptatriacontanoic acid | Heptatriacontanoic acid | $CH_3(CH_2)_{35}COOH$ C37:0 |
| Octatriacontanoic acid | Octatriacontanoic acid | $CH_3(CH_2)_{36}COOH$ C38:0 |

According to some embodiments, the fatty acid component comprises one or more of a mono-unsaturated fatty acid, a di-unsaturated fatty acid, a tri-unsaturated fatty acids, a tetra-unsaturated fatty acid, a pentaunsaturated fatty acid, or a hexa-unsaturated fatty acid. According to some embodiments, the fatty acid component comprises one or more of: crotonic acid; myristoleic; palmitoleic acid; sapienic acid; oleic acid; elaidic acid; vaccenic acid; gadoleic; eicosenoic acid; erucic acid; nervonic acid; linoleic acid; eicosadienoic acid; docosadienoic acid; linolenic acid; pinolenic acid; eleostearic acid; mead acid; dihomo-γ-linolenic acid; eicosatrienoic acid; stearidonic acid; arachidonic acid; eicosatetraenoic acid; adrenic acid; bosseopentaenoic acid; eicosapentaenoic acid; ozubondo; sardine acid; tetracosanolpentaenoic acid; docosahexaenoic acid; or herring acid.

Membrane Lipid Component

According to some embodiments of the described invention, the lipid component comprises a cell membrane lipid component.

According to some embodiments, the membrane lipid component is any amphipathic molecule having a hydrophilic end and hydrophobic end. According to some embodiments, the membrane lipid component has one or two hydrocarbon "tails". According to some embodiments, the membrane lipid component has one hydrocarbon tail comprising one or more double bonds and one hydrocarbon tail comprising no double bonds. According to some embodiments, the membrane lipid component has no double bonds in either hydrocarbon tail. According to some embodiments, the membrane lipid component has one or more double bonds in each hydrocarbon tail. According to some embodiments, the membrane lipid component has one or more cis-double bonds, one or more trans-double bonds, or no double bonds in the hydrocarbon tail. According to some embodiments, the membrane lipid component has a combination of two or more cis- and trans-double bonds.

Figure 23:
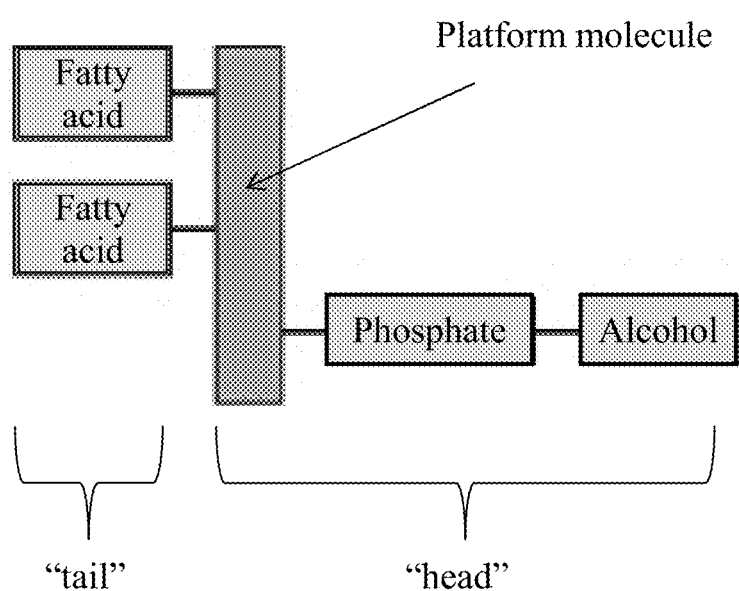
FIG. 23 depicts the general structure of the membrane lipid component. [Adapted from Biochemistry. 5th edition. Berg J M, Tymoczko J L, Stryer L. New York: W H Freeman; 2002.]

According to some embodiments, the membrane lipid component comprises the general structure of FIG. 23, wherein the platform molecule is any molecule capable of forming bonds with fatty acids and phosphate, including ethanolamine, choline, serine, glycerol, phosphatidylglycerol, and inositol.

According to some embodiments, the membrane lipid component comprises one or more $C_2$ to $C_{20}$ hydrocarbon tails. According to some embodiments, the membrane lipid component comprises a $C_2$ hydrocarbon tail, a $C_3$ hydrocarbon tail, a $C_4$ hydrocarbon tail, a $C_5$ hydrocarbon tail, a $C_6$ hydrocarbon tail, a $C_7$ hydrocarbon tail, a $C_8$ hydrocarbon tail, a $C_9$ hydrocarbon tail, a $C_{10}$ hydrocarbon tail, a $C_{ii}$ hydrocarbon tail, a $C_{12}$ hydrocarbon tail, a $C_{13}$ hydrocarbon tail, a $C_{14}$ hydrocarbon tail, a $C_{15}$ hydrocarbon tail, a $C_{16}$ hydrocarbon tail, a $C_{17}$ hydrocarbon tail, a $C_{18}$ hydrocarbon tail, a $C_{19}$ hydrocarbon tail, a $C_{20}$ hydrocarbon tail, a $C_{21}$ hydrocarbon tail, a $C_{22}$ hydrocarbon tail, a $C_{23}$ hydrocarbon tail, or a $C_{24}$ hydrocarbon tail.

According to some embodiments, the membrane lipid component has a hydrophilic "head" group. According to some embodiments, the membrane lipid component has a head group with an anionic or zwitterionic characteristic. According to some embodiments, the membrane lipid component has a head group comprising one or more of the following substituents: ethanolamine, choline, serine, glycerol, phosphatidylglycerol, or inositol. According to some embodiments, the membrane lipid component has a head group that has a net charge of 0, −1, −2, −3, or −4 at a pH of 7.

According to some embodiments, the membrane lipid component comprises one or more of a phospholipid, a glycolipid, a fatty acid, a phosphoglyceride, a sphingolipid, or a sterol.

According to some embodiments, the lipid membrane component is a sphingolipid found in the sphingolipid metabolic pathway of a cell. According to some embodiments, the membrane lipid component comprises one or more of ceramide, ceramide-1-phosphate, sphingomyelin, lactosylceramide, sphingosine, sphingosine-1-phosphate dihydroceramide, dihydrosphingosine, 3-ketodihydrosphingosine, or glucosylceramide. According to some embodiments, the membrane lipid component is a glycolipid containing one or more sugar residues. According to some embodiments, the membrane lipid component is a glycolipid containing one or more of glucose residues, galactose residues, or N-acetylneuraminic acid (NANA) residues. According to some embodiments, the membrane lipid component is a cerebroside or ganglioside. According to some embodiments, the membrane lipid component is one of phosphatidylcholine, phosphatidylethanolamine, or phosphatidylserine. According to some embodiments, the lipid membrane component is an inositol phospholipid.

Amino Acid Component

According to one aspect, the described invention comprises an organometallic complex comprising one or more amino acid components.

According to some embodiments, the amino acid component contains an amino acid or a derivative thereof.

Exemplary derivatives include, without limitation, a beta-amino acid, a homo-amino acid, proline and pyruvic acid derivatives, 3-substituted alanine derivatives, glycine derivatives, ring-substituted phenylalanine and tyrosine derivatives, linear core amino acids, N-formyl amino acids, and N-methyl amino acids. According to some embodiments, the amino acid derivative is Aceglutamide, N-Acetylaspartic acid, Acetylcarnitine, Acetylcysteine, N-Acetylglutamic acid, Acetylleucine, Acivicin, S-Adenosyl-L-homocysteine, Agaritine, Alanosine, Amino acid-based formula, Aminohippuric acid, L-Arginine ethyl ester, Arg-pyrimidine, Aspartame, Aspartylglucosamine, Benzylmercapturic acid, Biocytin, Brivanib alaninate, Carbocisteine, N(6)-Carboxymethyllysine, Carglumic acid, Cilastatin, Ciraparantag, Citiolone, Coprine, CPHPC, DCPG, DDAIP, Dibromotyrosine, Dihydroxyphenylglycine, Eflornithine, Fenclonine, 4-Fluoro-L-threonine, N-Formylmethionine, Fructose-asparagine, Gamma-L-Glutamyl-L-cysteine, 4-(γ-Glutamylamino)butanoic acid, Glutaurine, Glycocyamine, Hadacidin, Hepapressin, Lisinopril, Lymecycline, N-Methyl-D-aspartic acid, N-Methyl-L-glutamic acid, N-Methylornithine, Methylselenocysteine, Milacemide, Nitrosoproline, Nocardicin A, Nopaline, Octopine, Ombrabulin, Opine, Orthanilic acid, Oxaceprol, 2-Oxohistidine, L-Photo-Leucine, Polylysine, Remacemide, Salicyluric acid, Silk amino acid, Stampidine, Tabtoxin, Tetrazolylglycine, Thiorphan, Thymectacin, Tiopronin, Topaquinone, Tricine, Trimethylglycine, Tryptophan tryptophylquinone, Valaciclovir, Valganciclovir, or WAY-213,613.

Non-Transition Metal Component

According to one aspect, the described invention comprises an organometallic complex comprising one or more non-transition metal components.

According to some embodiments, the non-transition metal component comprises an elemental non-transition metal. According to some embodiments, the non-transition metal component comprises a salt of a non-transition metal. According to some embodiments, the non-transition metal component comprises zinc. According to some embodiments, the non-transition metal component comprises elemental zinc. According to some embodiments, the non-transition metal component comprises one or more of zinc carbonate, zinc gluconate, zinc chloride, zinc pyrithione, zinc sulfide, zinc methyl or zinc diethyl.

Macromolecule Component

According to one aspect, the described invention comprises an organometallic complex comprising one or more macromolecule components.

According to some embodiments the macromolecule component contains one or more polypeptide chains having a molecular weight of between 1 and 150 kilodaltons (kDa). According to some embodiments, the macromolecule component comprises a polypeptide chain having a molecular weight of at least 10 kDa. According to some embodiments, the macromolecule component comprises a polypeptide chain having a molecular weight of at least 20 kDa. According to some embodiments, the macromolecule component comprises a polypeptide chain having a molecular weight of at least 30 kDa. According to some embodiments, the macromolecule component comprises a polypeptide chain having a molecular weight of at least 40 kDa. According to some embodiments, the macromolecule component comprises a polypeptide chain having a molecular weight of at least 50 kDa. According to some embodiments, the macromolecule component comprises a polypeptide chain having a molecular weight of at least 60 kDa. According to some embodiments, the macromolecule component comprises a polypeptide chain having a molecular weight of at least 70 kDa. According to some embodiments, the macromolecule component comprises a polypeptide chain having a molecular weight of at least 80 kDa. According to some embodiments, the macromolecule component comprises a polypeptide chain having a molecular weight of at least 90 kDa. According to some embodiments, the macromolecule component comprises a polypeptide chain having a molecular weight of at least 100 kDa. According to some embodiments, the macromolecule component comprises a polypeptide chain having a molecular weight of at least 110 kDa. According to some embodiments, the macromolecule component comprises a polypeptide chain having a molecular weight of at least 120 kDa. According to some embodiments, the macromolecule component comprises a polypeptide chain having a molecular weight of at least 130 kDa. According to some embodiments, the macromolecule component comprises a polypeptide chain having a molecular weight of at least 140 kDa. According to some embodiments, the macromolecule component comprises a polypeptide chain having a molecular weight of at least 150 kDa.

According to some embodiments, the macromolecule component comprises one or more polypeptide chains having a molecular weight of between 26.6 and 48.5 kDa. According to some embodiments, the macromolecule component comprises one or more polypeptide chains having a molecular weight of about 43 kDa.

According to some embodiments, the macromolecule component comprises one or more polypeptides that have been modified by one or more of glycosylation, phosphorylation, ubiquitination, methylation, acetylation, alkylation, amide bond formation, carboxylation, hydroxylation, halogenation, nucleotide addition, sulfation, attachment of cofactors, or attachment of hydrophobic groups.

Immunoglobulins

Immunoglobulins (Ig) are glycoproteins produced by immune cells. Antibodies are serum proteins the molecules of which possess small areas of their surface that are complementary to small chemical groupings on their targets. These complementary regions (referred to as the antibody combining sites or antigen binding sites) of which there are at least two per antibody molecule, and in some types of antibody molecules ten, eight, or in some species as many as 12, may react with their corresponding complementary region on the antigen (the antigenic determinant or epitope) to link several molecules of multivalent antigen together to form a lattice. Immunoglobulins play a critical role in immune response by binding to particular antigens, such as those exhibited by bacteria or viruses. The binding of immunoglobulins to antigens targets them for destruction by the animal's immune cells.

The basic structural unit of a whole antibody molecule consists of four polypeptide chains, two identical light (L) chains (each containing about 220 amino acids) and two identical heavy (H) chains (each usually containing about 440 amino acids). The two heavy chains and two light chains are held together by a combination of noncovalent and covalent (disulfide) bonds. The molecule is composed of two identical halves, each with an identical antigen-binding site composed of the N-terminal region of a light chain and the N-terminal region of a heavy chain. Both light and heavy chains usually cooperate to form the antigen binding surface.

Human antibodies show two kinds of light chains, κ and λ; individual molecules of immunoglobulin generally are only one or the other. In normal serum, 60% of the molecules have been found to have κ determinants and 30 percent λ. Many other species have been found to show two kinds of light chains, but their proportions vary. For example, in the mouse and rat, λ chains comprise but a few percent of the total; in the dog and cat, κ chains are very low; the horse does not appear to have any κ chain; rabbits may have 5 to 40% λ, depending on strain and b-locus allotype; and chicken light chains are more homologous to λ than κ.

In mammals, there are five classes of antibodies, IgA, IgD, IgE, IgG, and IgM, each with its own class of heavy chain-α (for IgA), δ (for IgD), ε (for IgE), γ (for IgG) and μ (for IgM). In addition, there are four subclasses of IgG immunoglobulins (IgG1, IgG2, IgG3, IgG4) having γ1, γ2, γ3, and γ4 heavy chains respectively. In its secreted form, IgM is a pentamer composed of five four-chain units, giving it a total of 10 antigen binding sites. Each pentamer contains one copy of a J chain, which is covalently inserted between two adjacent tail regions.

All five immunoglobulin classes differ from other serum proteins in that they show a broad range of electrophoretic mobility and are not homogeneous. This heterogeneity—that individual IgG molecules, for example, differ from one another in net charge—is an intrinsic property of the immunoglobulins.

The principle of complementarity, which often is compared to the fitting of a key in a lock, involves relatively weak binding forces (hydrophobic and hydrogen bonds, van der Waals forces, and ionic interactions), which are able to act effectively only when the two reacting molecules can approach very closely to each other and indeed so closely that the projecting constituent atoms or groups of atoms of one molecule can fit into complementary depressions or recesses in the other. Antigen-antibody interactions show a high degree of specificity, which is manifest at many levels. Brought down to the molecular level, specificity means that the combining sites of antibodies to an antigen have a complementarity not at all similar to the antigenic determinants of an unrelated antigen. Whenever antigenic determinants of two different antigens have some structural similarity, some degree of fitting of one determinant into the combining site of some antibodies to the other may occur, and that this phenomenon gives rise to cross-reactions.

Monoclonal antibodies (mAbs) can be generated by fusing mouse spleen cells from an immunized donor with a mouse myeloma cell line to yield established mouse hybridoma clones that grow in selective media. A hybridoma cell is an immortalized hybrid cell resulting from the in vitro fusion of an antibody-secreting B cell with a myeloma cell. In vitro immunization, which refers to primary activation of antigen-specific B cells in culture, is another well-established means of producing mouse monoclonal antibodies.

Diverse libraries of immunoglobulin heavy (VH) and light (Vκ and Vλ) chain variable genes from peripheral blood lymphocytes also can be amplified by polymerase chain reaction (PCR) amplification. Genes encoding single polypeptide chains in which the heavy and light chain variable domains are linked by a polypeptide spacer (single chain Fv or scFv) can be made by randomly combining heavy and light chain V-genes using PCR. A combinatorial library then can be cloned for display on the surface of filamentous bacteriophage by fusion to a minor coat protein at the tip of the phage.

The technique of guided selection is based on human immunoglobulin V gene shuffling with rodent immunoglobulin V genes. The method entails (i) shuffling a repertoire of human λ light chains with the heavy chain variable region (VH) domain of a mouse monoclonal antibody reactive with an antigen of interest; (ii) selecting half-human Fabs on that antigen (iii) using the selected λ light chain genes as "docking domains" for a library of human heavy chains in a second shuffle to isolate clone Fab fragments having human light chain genes; (v) transfecting mouse myeloma cells by electroporation with mammalian cell expression vectors containing the genes; and (vi) expressing the V genes of the Fab reactive with the antigen as a complete IgG1, λ antibody molecule in the mouse myeloma.

According to some embodiments of the described invention, the macromolecule component comprises one or more immunoglobulins. According to some embodiments, the macromolecule component comprises an isolated heavy chain of the one or more immunoglobulins. According to some embodiments, the macromolecule component comprises an isolated light chain of an immunoglobulin.

According to some embodiments, the macromolecule component contains an isolated heavy chain of IgG. According to some embodiments, the macromolecule component contains an isolated a heavy chain of IgA. According to some embodiments, the macromolecule component contains an isolated δ heavy chain of IgD. According to some embodiments, the macromolecule component contains an isolated ε heavy chain of IgE. According to some embodiments, the macromolecule component contains an isolated μ heavy chain of IgM.

According to some embodiments, the macromolecule component contains an isolated κ light chain of Ig. According to some embodiments, the macromolecule component contains an isolated λ light chain of Ig.

Composition and Structure of the Organometallic Complex and Sub-Complexes Thereof 1. (Lipid)-(Transition Metal) Sub Complex According to some embodiments, the organometallic complex comprises a lipid component associated with a transition metal component. According to some embodiments, the lipid component is bonded to the transition metal component. According to some embodiments, the organometallic complex comprises a membrane lipid component associated with a transition metal component. According to some embodiments, the membrane lipid component is bonded to the transition metal component. According to some embodiments, the organometallic complex comprises a phospholipid associated with a transition metal component. According to some embodiments, the phospholipid is bonded to the transition metal component. According to some embodiments, the transition metal component bonded to the phospholipid component is a ruthenium component.

2. (Lipid)-(Transition Metal)-(Amino Acid) Sub Complex

According to some embodiments, the organometallic complex comprises a lipid component associated with a transition metal component and an amino acid component.

For example, according to some embodiments the lipid component comprises one or more of a membrane lipid, a fatty acid, or a phospholipid. According to some embodiments, the lipid component comprises a membrane lipid. According to some embodiments, the membrane lipid is a sphingomyelin membrane lipid.

Sphingomyelin, which is widely distributed in cell membranes, contains phosphocholine which is a strong dipole. Sphingomyelin also contains fatty acid chains, a considerable source of energy. Sphingomyelin is of interest for electro-active signaling, cell function, cell behavior, and bioregulation. [Kolesnick, R. N., Sphingomyelin and derivatives as cellular signals, Prog. Lipid Res. 30 (1), 1-38, 1991; Taniguchi, M., Okazaki, T., The role of sphingomyelin and sphingomyelin synthases in cell death, proliferation and migration—from animal models to human disorders, Biochem. Biophys. Acta, 1841 (5): 692-703, May 2014; Albi, E., Viola-Magni, M P, Chromatin-associated sphingomyelin: metabolism in relation to cell function, Cell Biochem. Funct., September; 21(3):211-5, 2003.] Complexes of the phosphocholine center of sphingomyelin with divalent metals have been reported, such as copper, cobalt, calcium, and magnesium. [James, P. F., Perugini, M. A., O'Hair, R. A., Electron capture dissociation of diacylglycerophosphocholine and divalent metal ions: competition between charge reduction and radical induced phospholipid fragmentation, 2008 Amer. Soc. Mass Spect., Elsevier, 1044-0305, doi: 10.1016/j.jasms, 2008.03.006].

According to some embodiments, the transition metal component comprises a ruthenium component. According to some embodiments, the ruthenium component comprises one or more of elemental ruthenium or a ruthenium salt. According to some embodiments, the transition metal component comprises elemental ruthenium.

According to some embodiments, the amino acid component comprises one or more naturally occurring or non-naturally occurring amino acids or amino acid derivatives. According to some embodiments, the amino acid component comprises a formyl functional group bonded to the amino group of an amino acid or amino acid derivative. According to some embodiments, the amino acid component comprises N-formyl methionine.

According to some embodiments the lipid component is associated with the ruthenium component, and the ruthenium component is associated with the amino acid component to form a lipid-ruthenium-amino acid sub-complex. For example, according to some embodiments, the lipid component is associated with the ruthenium component via a covalent, coordinate covalent, coordinate, hydrogen or other bond, or non-bond type association. According to some embodiments, the amino acid component is associated with the ruthenium component via a covalent, coordinate covalent, coordinate, hydrogen or other bond, or non-bond type association. According to some embodiments, the lipid component comprises sphingomyelin, the ruthenium component comprises elemental ruthenium, the amino acid component comprises N-formyl methionine, the lipid component is associated with the ruthenium via one or more of the oxygen atoms comprising the sphingomyelin, and the ruthenium is associated with the R group of N-formyl methionine, the oxygens comprising the N-formyl methionine or a combination thereof, via a covalent, coordinate covalent, coordinate, hydrogen or other bond, or non-bond type association.

3. (Lipid)-(Transition Metal)-(Amino Acid)-(Non Transition Metal) Sub Complex

According to some embodiments, the organometallic complex comprises a lipid component associated with a transition metal component, an amino acid component, and a non-transition metal component. According to some embodiments, the organometallic complex comprises a membrane lipid component associated with a transition metal component, an amino acid component, and a non-transition metal component. According to some embodiments, the organometallic complex comprises a membrane lipid component associated with a ruthenium component, an amino acid component, and a non-transition metal component. According to some embodiments, the organometallic complex comprises a phospholipid component associated with a ruthenium component, an amino acid component, and a non-transition metal component. According to some embodiments, the organometallic complex comprises a phospholipid component associated with a ruthenium component, an N-formyl methionine component, and a non-transition metal component. According to some embodiments, the organometallic complex comprises a sphingomyelin component associated with ruthenium component, an N-formyl methionine component, and a zinc component.

According to some embodiments, the organometallic complex comprises a sphingomyelin component associated with a ruthenium component, the ruthenium component associated with an N-formyl methionine component, and the N-Formyl methionine associated with the zinc component, wherein the components are associated via a covalent, coordinate covalent, non-covalent, hydrogen or other bond, or non-bond type association.

4. (Lipid)-(Transition Metal)-(Amino Acid)-(Macromolecule) Sub Complex

According to some embodiments, the organometallic complex comprises a lipid component associated with a transition metal component, an amino acid component, and a macromolecule.

For example, according to some embodiments the lipid component comprises one or more of a membrane lipid, a fatty acid, or a phospholipid. According to some embodiments, the lipid component comprises a membrane lipid. According to some embodiments, the membrane lipid is a sphingomyelin membrane lipid.

For example according to some embodiments the transition metal component comprises a ruthenium component. According to some embodiments, the ruthenium component comprises one or more of elemental ruthenium or a ruthenium salt. According to some embodiments, the transition metal component comprises elemental ruthenium.

For example, according to some embodiments the amino acid component comprises one or more naturally occurring or non-naturally occurring amino acids or amino acid derivatives. According to some embodiments, the amino acid component comprises a formyl functional group bonded to the amino group of an amino acid or amino acid derivative. According to some embodiments, the amino acid component comprises N-formyl methionine.

For example, according to some embodiments the macromolecule component comprises one or more polypeptides having a molecular weight of at least 40 kDa. According to some embodiments, the polypeptide is an immunoglobulin molecule. According to some embodiments, the immunoglobulin comprises an isolated immunoglobulin heavy chain, a light chain, or a combination thereof. According to some embodiments, the immunoglobulin comprises an isolated heavy chain of the immunoglobulin. According to some embodiments, the isolated heavy chain comprises an α, δ, ε, μ, or λ heavy chain.

According to some embodiments the lipid component is associated with the ruthenium component, the ruthenium component is associated with the amino acid component, and the macromolecule component is associated with one or more of the lipid component, ruthenium component, and amino acid component to form a lipid-ruthenium-amino acid-macromolecule sub-complex. For example, according to some embodiments, the lipid component is associated with the ruthenium component via a covalent, coordinate covalent, non-covalent, hydrogen or other bond, or non-bond type association. According to some embodiments, the amino acid component is associated with the ruthenium component via a covalent, coordinate covalent, coordinate, hydrogen or other bond, or non-bond type association. According to some embodiments, the macromolecule component is associated with one or more of the lipid component, ruthenium component, and amino acid component, via a covalent, coordinate covalent, non-covalent, hydrogen or other bond, or non-bond type association. According to some embodiments, the lipid component comprises sphingomyelin, the ruthenium component comprises elemental ruthenium, the amino acid component comprises N-formyl methionine, and the macromolecule component comprises an immunoglobulin. According to some embodiments, the lipid component is associated with the ruthenium via one or more of the oxygen atoms comprising the sphingomyelin, the ruthenium is associated with the R group of N-formyl methionine, the oxygens comprising the N-formyl methionine or a combination thereof, and the immunoglobulin is associated with one or more of the sphingomyelin, ruthenium, and N-formyl methionine, via a covalent, coordinate covalent, non-covalent, hydrogen or other bond, or non-bond type association.

5. (Lipid)-(Transition Metal)-(First Amino Acid)-(Non Transition Metal)-(Second Amino Acid) Sub Complex According to some embodiments, the organometallic complex comprises a lipid component associated with a transition metal component, an amino acid component, a non-transition metal component, and a second amino acid component. According to some embodiments, the organometallic complex comprises a membrane lipid component associated with a transition metal component, an amino acid component, a non-transition metal component, and a second amino acid component. According to some embodiments, the organometallic complex comprises a membrane lipid component associated with a ruthenium component, an amino acid component, a non-transition metal component, and a second amino acid component. According to some embodiments, the organometallic complex comprises a phospholipid component associated with a ruthenium component, an amino acid component, a non-transition metal component, and a second amino acid component. According to some embodiments, the organometallic complex comprises a phospholipid component associated with a ruthenium component, an N-formyl methionine component, a non-transition metal component, and a second amino acid component. According to some embodiments, the organometallic complex comprises a sphingomyelin component associated with ruthenium component, an N-formyl methionine component, a zinc component, and a threonine component.

According to some embodiments, the organometallic complex comprises a sphingomyelin component associated with a ruthenium component, the ruthenium component associated with a N-formyl methionine component, the N-Formyl methionine associated with a zinc component, and the zinc component associated with a threonine component, wherein the components are associated via one or more covalent, coordinate covalent, non-covalent, hydrogen or other bond, or non-bond type association.

6. (First Lipid)-(Transition Metal)-(First Amino Acid)-(Non Transition Metal)-(Second Amino Acid)-(Second Lipid) Sub Complex According to some embodiments, the organometallic complex comprises a lipid component associated with a transition metal component, an amino acid component, a non-transition metal component, a second amino acid component, and a second lipid component. According to some embodiments, the organometallic complex comprises a membrane lipid component associated with a transition metal component, an amino acid component, a non-transition metal component, a second amino acid component, and a second lipid component. According to some embodiments, the organometallic complex comprises a membrane lipid component associated with a ruthenium component, an amino acid component, a non-transition metal component, a second amino acid component and a second lipid component. According to some embodiments, the organometallic complex comprises a phospholipid component associated with a ruthenium component, an amino acid component, a non-transition metal component, a second amino acid component, and a second lipid component. According to some embodiments, the organometallic complex comprises a phospholipid component associated with a ruthenium component, an N-formyl methionine component, a non-transition metal component, a second amino acid component, and a second lipid component. According to some embodiments, the organometallic complex comprises a sphingomyelin component associated with ruthenium component, an N-formyl methionine component, a zinc component, a threonine component, and a linoleic acid component.

According to some embodiments, the organometallic complex comprises a sphingomyelin component associated with a ruthenium component, the ruthenium component associated with an N-formyl methionine component, the N-Formyl methionine associated with a zinc component, and the zinc component associated with a threonine component and a linoleic acid component, wherein the components are associated via a covalent, coordinate covalent, non-covalent, hydrogen or other bond, or non-bond type association.

7. (First Lipid)-(Transition Metal)-(First Amino Acid)-(Non-Transition Metal)-(Second Amino Acid)-(Second Lipid)-(Third Amino Acid) Sub Complex According to some embodiments, the organometallic complex comprises a first lipid component associated with a transition metal component, a first amino acid component, a non-transition metal component, a second amino acid component, a second lipid component, and a third amino acid component.

For example, the first lipid component comprises one or more of a membrane lipid, a fatty acid, or a phospholipid. According to some embodiments, the lipid component comprises a membrane lipid. According to some embodiments, the lipid component comprises a sphingomyelin membrane lipid.

For example, the transition metal component comprises a ruthenium component. According to some embodiments, the ruthenium component comprises one or more of elemental ruthenium or a ruthenium salt. According to some embodiments, the transition metal component comprises elemental ruthenium.

For example, the first amino acid component comprises one or more naturally occurring or non-naturally occurring amino acids or amino acid derivatives. According to some embodiments, the first amino acid component comprises a formyl functional group bonded to the amino group of an amino acid or amino acid derivative. According to some embodiments, the first amino acid component comprises N-formyl methionine.

For example, the non-transition metal component comprises a zinc component. According to some embodiments, the zinc component comprises one or more of elemental zinc or a zinc salt. According to some embodiments, the zinc component comprises elemental zinc.

For example, the second amino acid component comprises one or more naturally occurring or non-naturally occurring amino acids or amino acid derivatives. According to some embodiments, the second amino acid component comprises a naturally occurring amino acid. According to some embodiments, the second amino acid component comprises threonine.

For example, the second lipid component comprises one or more of a membrane lipid, a fatty acid, or a phospholipid. According to some embodiments, the second lipid component comprises a fatty acid. According to some embodiments, the second lipid component comprises a fatty acid of 20 carbons in length. According to some embodiments, the second lipid component comprises a linoleic acid.

For example, the third amino acid component comprises one or more naturally occurring or non-naturally occurring amino acids or amino acid derivatives. According to some embodiments, the third amino acid component comprises a naturally occurring amino acid. According to some embodiments, the third amino acid component comprises arginine.

According to some embodiments the lipid component is associated with the ruthenium component, the ruthenium component is associated with a first amino acid component, the first amino acid component is associated with a non-transition metal component, the non-transition metal component is associated with a second amino acid and a second lipid, and the second lipid is associated with a third amino acid to form a first lipid-transition metal-first amino acid-non-transition metal-second amino acid-second lipid-third amino acid sub-complex. For example, the first lipid component is associated with the ruthenium component via a covalent, coordinate covalent, non-covalent, hydrogen or other bond, or non-bond type association. According to some embodiments, the first amino acid component is associated with the ruthenium component via a covalent, coordinate covalent, non-covalent, hydrogen or other bond, or non-bond type association. According to some embodiments, the first lipid component comprises sphingomyelin, the ruthenium component comprises elemental ruthenium, the amino acid component comprises N-formyl methionine, and the ruthenium is associated (1) with the sphingomyelin via one or more of the oxygen atoms comprising the sphingomyelin and (2) with the R group of N-formyl methionine, one or more of the oxygens comprising the N-formyl methionine or a combination thereof, via a covalent, coordinate covalent, non-covalent, hydrogen or other bond, or non-bond type association. According to some embodiments, the first amino acid complex is associated with the non-transition metal component via a covalent, coordinate covalent, non-covalent, hydrogen or other bond, or non-bond type association. According to some embodiments, the first amino acid is N-formyl methionine and the non-transition metal comprises elemental zinc, wherein the zinc is associated with the N-formyl methionine by an oxygen atom of the N-formyl methionine via a covalent, coordinate covalent, non-covalent, hydrogen or other bond, or non-bond type association. According to some embodiments, the second amino acid is associated with the non-transition metal component via a covalent, coordinate cova-lent, non-covalent, hydrogen or other bond, or non-bond type association. According to some embodiments, the non-transition metal component is elemental zinc and the second amino acid is threonine, wherein the zinc is associated with an oxygen atom and nitrogen atom of the threonine, via a covalent, coordinate covalent, non-covalent, hydrogen or other bond, or non-bond type association. According to some embodiments, the non-transition metal component is associated with the second lipid component, via a covalent, coordinate covalent, non-covalent, hydrogen or other bond, or non-bond type association. According to some embodiments, the non-transition metal component is elemental zinc and the second lipid component is linoleic acid, wherein the zinc is associated with the linoleic acid via its w carbon atom, via a covalent, coordinate covalent, non-covalent, hydrogen or other bond, or non-bond type association. According to some embodiments, the second lipid component is associated with a third amino acid component via a covalent, coordinate covalent, non-covalent, hydrogen or other bond, or non-bond type association. According to some embodiments, the second lipid component is a linoleic acid and the third amino acid component is an arginine, wherein the R group of the lysine is associated with the hydrocarbon region of the linoleic acid and the amino terminus of the arginine non-covalently is associated with the carboxylic acid of the linoleic acid, via a covalent, coordinate covalent, non-covalent, hydrogen or other bond, or non-bond type association.

According to some embodiments, the organometallic complex comprises a sphingomyelin component associated with a ruthenium component, the ruthenium component associated with an N-formyl methionine component, the N-Formyl methionine associated with a zinc component, the zinc component associated with a threonine component and a linoleic acid component, the linoleic acid component associated with an arginine component, wherein the components are associated via a covalent, coordinate covalent, non-covalent, hydrogen or other bond, or non-bond type association.

8. (First Lipid)-(Transition Metal)-(First Amino Acid)-(Non-Transition Metal)-(Second Amino Acid)-(Second Lipid)-(Third Amino Acid)-(Macromolecule) Complex According to some embodiments, the organometallic complex comprises a first lipid component associated with a transition metal component, a first amino acid component, a non-transition metal component, a second amino acid component, a second lipid component, and a third amino acid component, wherein one or more of the first lipid, transition metal, first amino acid, non-transition metal, second amino acid, second lipid, and third amino acid also are associated with a macromolecule.

For example, the first lipid component comprises one or more of a membrane lipid, a fatty acid, or a phospholipid. According to some embodiments, the lipid component comprises a membrane lipid. According to some embodiments, the lipid component comprises a sphingomyelin membrane lipid.

For example, the transition metal component comprises a ruthenium component. According to some embodiments, the ruthenium component comprises one or more of elemental ruthenium or a ruthenium salt. According to some embodiments, the transition metal component comprises elemental ruthenium.

For example, the first amino acid component comprises one or more naturally occurring or non-naturally occurring amino acids or amino acid derivatives. According to some embodiments, the first amino acid component comprises a formyl functional group bonded to the amino group of an amino acid or amino acid derivative. According to some embodiments, the first amino acid component comprises N-formyl methionine.

For example, the non-transition metal component comprises a zinc component. According to some embodiments, the zinc component comprises one or more of elemental zinc or a zinc salt. According to some embodiments, the zinc component comprises elemental zinc.

For example, the second amino acid component comprises one or more naturally occurring or non-naturally occurring amino acids or amino acid derivatives. According to some embodiments, the second amino acid component comprises a naturally occurring amino acid. According to some embodiments, the second amino acid component comprises threonine.

For example, the second lipid component comprises one or more of a membrane lipid, a fatty acid, or a phospholipid. According to some embodiments, the second lipid component comprises a fatty acid. According to some embodiments, the second lipid component comprises a fatty acid of 20 carbons in length. According to some embodiments, the second lipid component comprises a linoleic acid.

For example, the third amino acid component comprises one or more naturally occurring or non-naturally occurring amino acids or amino acid derivatives. According to some embodiments, the third amino acid component comprises a naturally occurring amino acid. According to some embodiments, the third amino acid component comprises arginine.

For example, the macromolecule component comprises one or more polypeptides having a molecular weight of at least 40 kDa. According to some embodiments, the polypeptide is an immunoglobulin molecule. According to some embodiments, the immunoglobulin comprises an isolated immunoglobulin heavy chain, a light chain, or a combination thereof. According to some embodiments, the immunoglobulin comprises an isolated heavy chain of the immunoglobulin. According to some embodiments, the isolated heavy chain comprises an $\alpha$, $\delta$, $\varepsilon$, $\mu$, or $\lambda$, heavy chain.

According to some embodiments the lipid component is associated with the ruthenium component, the ruthenium component is associated with a first amino acid component, the first amino acid component is associated with a non-transition metal component, the non-transition metal component is associated with a second amino acid and a second lipid, the second lipid is associated with a third amino acid, and one or more of the first lipid, transition metal, first amino acid, non-transition metal, second amino acid, second lipid, and third amino acid are associated with a macromolecule to form a first lipid-transition metal-first amino acid-non-transition metal-second amino acid-second lipid-third amino acid-macromolecule complex.

For example, the first lipid component is associated with the ruthenium component via a covalent, coordinate covalent, non-covalent, hydrogen or other bond, or non-bond type association. According to some embodiments, the first amino acid component is associated with the ruthenium component via a covalent, coordinate covalent, non-covalent, hydrogen or other bond, or non-bond type association. According to some embodiments, the first lipid component comprises sphingomyelin, the ruthenium component comprises elemental ruthenium, and the amino acid component comprises N-formyl methionine. According to some embodiments, the ruthenium is associated with the sphingomyelin via one or more of the oxygen atoms comprising the sphingomyelin, and the ruthenium is associated with the R group of N-formyl methionine, one or more of the oxygens comprising the N-formyl methionine or a combination thereof, via a covalent, coordinate covalent, non-covalent, hydrogen or other bond, or non-bond type association. According to some embodiments, the first amino acid complex is associated with the non-transition metal component via a covalent, coordinate covalent, non-covalent, hydrogen or other bond, or non-bond type association. According to some embodiments, the first amino acid complex is N-formyl methionine and the non-transition metal comprises elemental zinc, wherein the zinc is associated with the N-formyl methionine by an oxygen atom of the N-formyl methionine, via a covalent, coordinate covalent, non-covalent, hydrogen or other bond, or non-bond type association. According to some embodiments, the second amino acid is associated with the non-transition metal component via a covalent, coordinate covalent, non-covalent, hydrogen or other bond, or non-bond type association. According to some embodiments, the non-transition metal component is elemental zinc and the second amino acid is threonine, wherein the zinc is associated with an oxygen atom of the threonine, a nitrogen atom of the threonine, or a combination thereof, via a covalent, coordinate covalent, non-covalent, hydrogen or other bond, or non-bond type association. According to some embodiments, the non-transition metal component is associated with the second lipid component via a covalent, coordinate covalent, non-covalent, hydrogen or other bond, or non-bond type association. According to some embodiments, the non-transition metal component is elemental zinc and the second lipid component is linoleic acid, wherein the zinc is associated with the linoleic acid via its w carbon atom, via a covalent, coordinate covalent, non-covalent, hydrogen or other bond, or non-bond type association. According to some embodiments, the second lipid component is associated with a third amino acid component via a covalent, coordinate covalent, non-covalent, hydrogen or other bond, or non-bond type association. According to some embodiments, the second lipid component is a linoleic acid and the third amino acid component is an arginine, wherein the R group of the lysine is associated with the hydrocarbon region of the linoleic acid and the amino terminus of the arginine non-covalently is associated with the carboxylic acid of the linoleic acid, via a covalent, coordinate covalent, non-covalent, hydrogen or other bond, or non-bond type association. According to some embodiments, the one or more of the first lipid, transition metal, first amino acid, non-transition metal, second amino acid, second lipid, and third amino acid are associated with a macromolecule via a covalent, coordinate covalent, non-covalent, hydrogen or other bond, or non-bond type association.

According to some embodiments, the organometallic complex comprises a sphingomyelin component associated with a ruthenium component, the ruthenium component associated with a N-formyl methionine component, the N-Formyl methionine associated with a zinc component, the zinc component associated with a threonine component and a linoleic acid component, the linoleic acid component associated with an arginine component, and a heavy chain Ig associated with one or more of the sphingomyelin component, ruthenium component, N-Formyl methionine component, zinc component, threonine component, linoleic acid component, and arginine component, wherein the components are associated via a covalent, coordinate covalent, non-covalent, hydrogen or other bond, or non-bond type association.

According to some embodiments, the macromolecule component comprises one or more polypeptides that have a three-dimensional structure adapted to interact with the head group of a sphingomyelin component. According to some embodiments, the macromolecule component comprises one or more polypeptides that have a three-dimensional structure adapted to interact with an amino acid component. According to some embodiments, the macromolecule component comprises one or more polypeptides that have a three-dimensional structure adapted to interact with a fatty acid component.

According to some embodiments, the arginine linked to the linoleic acid component facilitates water solubility of the linoleic acid. According to some embodiments, the arginine functions as a charge donor.

According to some embodiments, the complex comprises a transition metal component, a non-transition metal component, and at least one organyl component. According to some embodiments, the transition metal component comprises a ruthenium component. According to some embodiments, the transition metal component comprises a ruthenium component, and the non-transition metal component comprises a zinc component. According to another embodiment, the zinc component is associated with a ruthenium component and at least one organyl component. According to some embodiments, at least one organyl component comprises a fatty acid component or a derivative thereof. According to some embodiments, the fatty acid comprises one or more hydrocarbon chains of from 2 to twenty carbon atoms, wherein at one end of the one or more hydrocarbon chains is a negatively charged functional group. According to some embodiments, the complex comprises one or more hydrocarbon chains of from 2 to 20 carbon atoms, wherein at one end of the one or more hydrocarbon chains is a phosphocholine group. According to some embodiments, the at least one organyl component comprises linoleic acid or a derivative thereof. According to some embodiments, the at least one organyl component comprises at least one amino acid. According to some embodiments, the at least one organyl component comprises threonine. According to some embodiments, the at least one organyl component comprises arginine. According to some embodiments, the at least one organyl component is linoleic acid to which arginine is associated with. According to some embodiments, the arginine facilitates the water solubility of the linoleic acid. According to some embodiments, an organyl component is a structural connection between the ruthenium component and the zinc component. According to some embodiments, an amino acid component is a structural connection between the ruthenium component and the zinc component. According to some embodiments, N-formyl methionine is a structural connection between the ruthenium component and the zinc component. According to some embodiments, the organometallic complex comprises a macromolecular structure. According to some embodiments, the organometallic complex comprises a protein.

According to some embodiments, the described invention comprises an organometallic complex of Formula I:

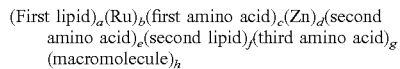

wherein the first lipid component comprises a sphingomyelin or a derivative thereof; the Ru signifies a ruthenium component; the first, second, and third amino acid components comprise an amino acid or a derivative thereof; the Zn signifies a zinc component; the second lipid component comprises a hydrocarbon chain of from 2 to twenty carbon atoms wherein at one end of the hydrocarbon chain (ω carbon) is a methyl group and at the other end (α carbon) is a carboxyl group; the macromolecule component comprises a polypeptide chain; wherein a, b, c, and h are at least 1; and d, e, f, and g are 0 or 1; wherein e, f, and g are 0 when d is 0, and g is 0 when f is 0; wherein the Ru component is associated with the sphingomyelin component with the first amino acid component; the Zn component is associated with the first amino acid component with one or more of the second amino acid component or fatty acid component; the third amino acid component is associated with the fatty acid component; and the macromolecule component is associated with one or more of the first lipid component, the Ru component, the first amino acid component, the Zn component, the second amino acid component, the third amino acid component, or the second lipid component.

According to some embodiments, the organometallic complex comprises an organified ruthenium component comprising a ruthenium component and at least one organyl component, wherein the ruthenium component is associated with the organyl component. According to some embodiments, the organyl component comprises a cell membrane lipid and a first amino acid. According to one such embodiment, the first amino acid component comprises n-formyl methionine. According to some embodiments the cell membrane lipid comprises a sphingomyelin lipid. According to some embodiments, the ruthenium component is associated with the organyl component via one or more carbonyl groups. According to some embodiments where the organyl component comprises n-formyl methionine and sphingomyelin, the ruthenium component is associated with the organyl component via bonds between one or more of: the ruthenium and the carbonyl groups of n-formyl methionine; the ruthenium and the methyl group of n-formyl methionine; the ruthenium and the carbonyl of sphingomyelin; the ruthenium and the alcohol group of sphingomyelin.

According to some embodiments, the complex comprises an organified zinc component comprising a zinc component and at least one organyl component. According to some embodiments, the zinc component is bonded to the organyl component. According to some embodiments, the organyl component comprises a second amino acid or a fatty acid component. According to some embodiments the fatty acid component comprises a hydrocarbon chain of from 2 to twenty carbon atoms, wherein at one end of the hydrocarbon chain (the ω carbon) is a methyl group and at the α carbon on the other end is a carboxyl group. According to some embodiments, the second amino acid component comprises threonine. According to some embodiments, the fatty acid component comprises linoleic acid. According to some embodiments, the at least one organyl component comprises a third amino acid component. According to some embodiments, the third amino acid component is arginine. According to some embodiments, the fatty acid component is a linoleic acid to which the arginine is linked. According to some embodiments, the arginine facilitates water solubility of the linoleic acid. According to some embodiments, the zinc component is associated with the organyl component via bonds between the zinc atom with one or more of carbonyl group, amine group, and methyl group of the organyl component.

According to some embodiments, the organified ruthenium component is bonded to the organified zinc component. According to some embodiments, the organified ruthenium component is associated with the organified zinc component via a bond between the zinc component and the first amino acid. According to some embodiments, the bond connecting the organified ruthenium component and organified zinc component is via the zinc atom and a carbonyl group on the amino acid.

According to some embodiments, one or more of the organified ruthenium component and organified zinc component is(are) associated with a macromolecule. According to some embodiments, the association is via one or more bonds. According to some embodiments, the macromolecule comprises one or more chains of polypeptides. According to some embodiments, the macromolecule comprises one or more polypeptide chains of gamma globulin, an intact gamma globulin, or a fragment of a gamma globulin.

According to some embodiments, the described complexes and sub complexes of the invention can be identified using UV-visible spectroscopy and by Fourier transform-infrared spectroscopy (FTIR).

The complex of the invention may exist in a form including in a solid form, in a liquid form, as a dispersion, suspension, or as a solution.

As is common in metal to ligand syntheses, multiple complexes may be produced.

Pharmaceutical Compositions Comprising an Organometallic Complex

According to another aspect, the described invention provides a pharmaceutical composition comprising:

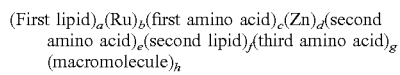

wherein the first lipid component comprises a sphingomyelin or a derivative thereof; the Ru signifies a ruthenium component; the first, second, and third amino acid components comprise an amino acid or a derivative thereof; the Zn signifies a zinc component; the second lipid component comprises a hydrocarbon chain of from 2 to twenty carbon atoms wherein at one end of the hydrocarbon chain ($\omega$ carbon) is a methyl group and at the other end ($\alpha$ carbon) is a carboxyl group; the macromolecule component comprises a polypeptide chain; wherein a, b, c, and h are at least 1; and d, e, f, and g are 0 or 1; wherein e, f, and g are 0 when d is 0, and g is 0 when f is 0; wherein the Ru component connects the sphingomyelin component with the first amino acid component; the Zn component connects the first amino acid component with one or more of the second amino acid component or fatty acid component; the third amino acid component is associated with the fatty acid component; the macromolecule component interacts with one or more of the first lipid component, the Ru component, the first amino acid component, the Zn component, the second amino acid component, the third amino acid component, or the second lipid component.

The organometallic complex, the ruthenium component the sphingomyelin component, the first, second, and third amino acid components, the fatty acid component and the macromolecule component are as has been described above.

The structural and functional properties of the organometallic complex are as have been described above.

Pharmaceutically Acceptable Carrier

According to some embodiments, the pharmaceutical composition can be formulated with an excipient, carrier or vehicle including, but not limited to, a solvent. The terms "excipient", "carrier", or "vehicle" as used herein refers to carrier materials suitable for formulation and administration of the chemotactic hematopoietic stem cell product described herein. Carriers and vehicles useful herein include any such materials know in the art which are nontoxic and do not interact with other components. As used herein the phrase "pharmaceutically acceptable carrier" refers to any substantially non-toxic carrier useable for formulation and administration of the composition of the described invention in which the organometallic complex of the described invention will remain stable and bioavailable.

The pharmaceutically acceptable carrier must be of sufficiently high purity and of sufficiently low toxicity to render it suitable for administration to the mammal being treated. It further should maintain the stability and bioavailability of the organometallic complex. The pharmaceutically acceptable carrier can be liquid or solid and is selected, with the planned manner of administration in mind, to provide for the desired bulk, consistency, etc., when combined with an active agent and other components of a given composition. For example, the pharmaceutically acceptable carrier may be, without limitation, a binding agent (e.g., pregelatinized maize starch, polyvinylpyrrolidone or hydroxypropyl methylcellulose, etc.), a filler (e.g., lactose and other sugars, microcrystalline cellulose, pectin, gelatin, calcium sulfate, ethyl cellulose, polyacrylates, calcium hydrogen phosphate, etc.), a lubricant (e.g., magnesium stearate, talc, silica, colloidal silicon dioxide, stearic acid, metallic stearates, hydrogenated vegetable oils, corn starch, polyethylene glycols, sodium benzoate, sodium acetate, etc.), a disintegrant (e.g., starch, sodium starch glycolate, etc.), or a wetting agent (e.g., sodium lauryl sulfate, etc.). Other suitable pharmaceutically acceptable carriers for the compositions of the described invention include, but are not limited to, water, buffers, salt solutions, alcohols, polyethylene glycols, gelatins, amyloses, magnesium stearates, talcs, silicic acids, viscous paraffins, hydroxymethylcelluloses, polyvinylpyrrolidones and the like. Such carrier solutions also can contain buffers, diluents and other suitable additives. The term "buffer" as used herein refers to a solution or liquid whose chemical makeup neutralizes acids or bases without a significant change in pH. Examples of buffers envisioned by the described invention include, but are not limited to, Dulbecco's phosphate buffered saline (PBS), Ringer's solution, 5% dextrose in water (D5W), and normal/physiologic saline (0.9% NaCl). According to some embodiments, the infusion solution is isotonic to subject tissues. According to some embodiments, the infusion solution is hypertonic to subject tissues.

Administration

In general, the pharmaceutical compositions of the present invention may be formulated by any means known in the art, including not limited to formulation as tablets, capsules, caplets, suspensions, powders, lyophilized preparations, suppositories, ocular drops, skin patches, oral soluble formulations, sprays, aerosols and the like, and may be mixed and formulated with buffers, binders, excipients, stabilizers, anti-oxidants and other agents known in the art. Any route of administration by which provided compositions of the invention are introduced across an epidermal layer of cells may be employed. The pharmaceutical compositions of the present invention may be administered by any enteral or parenteral route. Administration routes may thus include administration through mucous membranes, enteral administration, parenteral administration, topical administration, inhalation administration, pulmonary administration, nasal administration, and the like.

Enteral administration includes any suitable form for oral consumption including, for example, tablets, pills, liquid gels, capsules, elixir, and troches. For instance, for oral administration in the form of tablets or capsules, the active drug components may be combined with any oral non-toxic pharmaceutically acceptable inert carrier such as starch, cellulose, magnesium stearate, dicalcium phosphate, calcium sulfate, mannitol, and the like. Moreover, when desired or necessary, suitable binders, lubricants, disintegrating agents and coloring agents can also be incorporated in the mixture. Suitable binders, for example, include starch, gelatin, natural and synthetic gums such as acacia, sodium alginate, carboxymethylcellulose, polyethylene glycol and waxes. Among the lubricants, there may be mentioned for use in these dosage forms, boric acid, sodium benzoate, sodium acetate, sodium chloride, etc. Disintegrators include, without limitation, starch, methylcellulose, agar, bentonite, guar gum, etc. Flavoring agents and preservatives can also be included where appropriate. In the case of tablets, they can be further coated with the usual coating materials to make, for example, sugar-coated tablets, gelatin film-coated tablets, tablets coated with enteric coatings, tablets coated with films or double-layered and multi-layer tablets.

The pharmaceutical composition of the described invention may be a sterile solution or suspension in a nontoxic parenterally acceptable diluent or solvent. A solution generally is considered as a homogeneous mixture of two or more substances; it is frequently, though not necessarily, a liquid. In a solution, the molecules of the solute (or dissolved substance) are uniformly distributed among those of the solvent. A suspension is a dispersion (mixture) in which a finely-divided species is combined with another species, with the former being so finely divided and mixed that it does not rapidly settle out. In everyday life, the most common suspensions are those of solids in liquid water. Among the acceptable vehicles and solvents that may be employed are water, Ringer's solution, and isotonic sodium chloride (saline) solution. According to some embodiments, hypertonic solutions are employed. In addition, sterile, fixed oils conventionally are employed as a solvent or suspending medium. For parenteral application, suitable vehicles consist of solutions, e.g., oily or aqueous solutions, as well as suspensions, emulsions, or implants. Aqueous suspensions may contain substances, which increase the viscosity of the suspension and include, for example, sodium carboxymethyl cellulose, sorbitol and/or dextran. The aqueous sterile injectable solutions may further contain anti-oxidants, buffers, bacteriostats, isotonicity adjusters and like additions acceptable for parenteral formulations. Parental administration includes intravenous, intramuscular, subcutaneous, intradermal, topical, intra-thecal and intra-arterial methods. Compositions of the described invention that are for parenteral administration may include pharmaceutically acceptable carriers such as sterile aqueous solutions, non-aqueous solutions in common solvents such as alcohols, or solutions in a liquid oil base.

Formulations of the present invention suitable for topical application to the skin take the form of an ointment, cream, lotion, paste, gel, spray, aerosol, transdermal device or oil. Additives which may be used include vaseline, lanolin, polyethylene glycols, alcohols, transdermal enhancers, and combinations of two or more thereof. Transdermal pharmaceutical devices include patches, occlusive dressings, occlusive formulations, hypodermic sprays, iontophoretic systems, gels and infusion pumps, all of which are well known in the art. A transdermal patch which includes a pharmaceutical may generally include a backing layer impermeable to the pharmaceutical, a reservoir to house the pharmaceutical, and an adhesive cover to be removed upon use of the patch and for adhesion to the skin of a patient. Formulations suitable for transdermal administration may also be presented as medicated bandages or discrete patches adapted to remain in intimate contact with the epidermis of the recipient for a prolonged period of time. Representative examples of suitable transdermal patches include, for example, those developed by NeuroDerm Ltd (Israel) and/or that used to deliver estradiol, for example, those developed by Novogyne Pharmaceuticals. Formulations suitable for transdermal administration may also be delivered by iontophoresis (passage of a small electric current (about 15 mA) to "inject" electrically charged ions into the skin) through the skin. For this, the dosage form typically takes the form of an optionally buffered aqueous solution of the active compound. Formulations suitable for transdermal administration may also be delivered by using an infusion pump connected to a needle that is inserted through the skin, for example, those developed by Medtronic used to deliver insulin. Amounts used in a transdermal device as described herein may vary, depending on many factors including the size of the device and its release characteristics, the amount of the pharmaceutical active agent and the estimated duration of action of the device.

For administration by inhalation, compositions for use in the present invention can be delivered in the form of an aerosol spray in a pressurized package or as a nebulizer, with use of suitable propellants. In the case of a pressurized aerosol, the dosage unit can be determined by providing a valve to deliver a metered dose in accordance with the invention.

According to some embodiments, the carrier may include a release agent such as a sustained release or delayed release carrier. In such embodiments, the carrier may be any material capable of sustained or delayed release of the active to provide a more efficient administration, e.g., resulting in less frequent and/or decreased dosage of the composition, improve ease of handling, and extend or delay effects on diseases, disorders, conditions, syndromes, and the like, being treated, prevented or promoted. Non-limiting examples of such carriers include liposomes, microsponges, microspheres, or microcapsules of natural and synthetic polymers and the like. Liposomes may be formed from a variety of phospholipids such as cholesterol, stearylamines or phosphatidylcholines.

The pharmaceutical compositions of the described invention may be administered parenterally in the form of a sterile injectable aqueous or oleaginous suspension. The term "parenteral" or "parenterally" as used herein refers to introduction into the body by way of an injection (i.e., administration by injection), including, but not limited to, infusion techniques.

Various unit dose and multidose containers, e.g., sealed ampules and vials, may be used, as is well-known in the art. The essential ingredients of the sterile parenteral formulation, e.g., the water and the organometallic complex, may be presented in a variety of ways, as long as the solution ultimately administered to the patient contains the appropriate amounts of the essential ingredients. Thus, for example, the organometallic complex/water formulation may be presented in a unit dose or multidose container, ready for injection. As another example, a concentrated solution of the organometallic complex/water may be presented in a separate container from a diluting liquid (water or organometallic complex/water) designed so that the contents can be combined to give a formulation containing appropriate amounts for injection. As another alternative, the organometallic complex may be provided in a freeze-dried condition in one container, while a separate container contains diluting liquid (water or organometallic complex/water, depending on the amount of organometallic complex in the other container), again designed so that the contents can be combined to give a formulation containing the appropriate amounts of the water and selected organometallic complex. In any event, the contents of each container will be sterile. Suitable carriers for parenteral administration include, for example, water, ethyl alcohol, propylene glycol, ethoxylated isostearyl alcohol, polyoxylated isostearyl alcohol, polyoxyethylene sorbitol and sorbitate esters. In these instances, adequate amounts of sodium chloride, glucose or glycerin can be added to make the preparations isotonic.

Additionally, pharmaceutical compositions of the described invention may be prepared using technology, which is known in the art, such as described in Remington's Pharmaceutical Sciences, 18th or 19th editions, published by the Mack Publishing Company of Easton, Pa., which is incorporated herein by reference.

A skilled artisan may determine the therapeutic amount of the inventive compositions by determining the dose in a dosage unit (meaning unit of use) that elicits a given intensity of effect, hereinafter referred to as the "unit dose." The term "dose-intensity relationship" refers to the manner in which the intensity of effect in an individual recipient relates to dose. The intensity of effect generally designated is 50% of maximum intensity. The corresponding dose is called the 50% effective dose or individual ED50. The use of the term "individual" distinguishes the ED50 based on the intensity of effect as used herein from the median effective dose, also abbreviated ED50, determined from frequency of response data in a population. "Efficacy" as used herein refers to the property of the compositions of the described invention to achieve the desired response, and "maximum efficacy" refers to the maximum achievable effect. The therapeutic amount of the pharmaceutical compositions of the described invention that will be effective in the treatment of a particular disorder or condition will depend on the nature of the disorder or condition, and may be determined by standard clinical techniques. (See, for example, Goodman and Gilman's THE PHARMACOLOGICAL BASIS OF THERAPEUTICS, Joel G. Harman, Lee E. Limbird, Eds.; McGraw Hill, New York, 2001; THE PHYSICIAN'S DESK REFERENCE, Medical Economics Company, Inc., Oradell, N.J., 1995; and DRUG FACTS AND COMPARISONS, FACTS AND COMPARISONS, INC., St. Louis, Mo., 1993), each of which is incorporated by reference herein. The precise dose to be employed in the formulations of the described invention also will depend on the route of administration and the seriousness of the disease or disorder, and should be decided according to the judgment of the practitioner and each subject's circumstances.

The terms "therapeutic amount", "therapeutic effective amount" or an "amount effective" of one or more of the therapeutic agents is an amount that is sufficient to provide the intended benefit of treatment. According to some embodiments, the therapeutic amount has an anti-tumor or anti-cancer effect. According to some embodiments, the anti-tumor or anti-cancer effect comprises cytotoxicity of cancer cells, inhibited growth of cancer cells, inhibited migration of cells or any combination of these effects. According to some embodiments, the anti-cancer effect comprises condensation of cancer cell chromatin. The anti-cancer effect may be curing, minimizing, preventing or ameliorating a cancer disease or disorder, or may have any other adverse consequence reversing, or pharmaceutical beneficial effect. The concentration of the substance is selected so as to exert its therapeutic effect, but low enough to avoid significant side effects within the scope and sound judgment of the physician. The effective amount of the composition may vary with the age and physical condition of the biological subject being treated, the severity of the condition, the duration of the treatment, the nature of concurrent therapy, the timing of the infusion, the specific compound, composition or other active ingredient employed, the particular carrier utilized, and like factors.

For example, when the pharmaceutical composition of the present invention is parenterally administered to a patient, a dosage of between about 0.1 mL to 5 mL daily of a 25 mg/mL solution of the pharmaceutical composition for at least about 5-7 days is employed. An exemplary dosage pattern in adult humans is about 0.5 mL of 25 mg/mL of the composition administered daily for the first three days of treatment, followed by 0.3 mL daily for an additional 7 days of treatment. However, the precise route of administration, dosage and frequency of administration is individualized for each patient and can vary over a wide range depending on the particular disease state being treated, the condition of the patient and the like.

According to some embodiments, the complex in solution is present in an amount sufficient to produce a therapeutic effect after administration.

Methods of Treatment

According to another aspect, the described inventions provide a method of treating aberrant cellular growth and migration in a mammal, comprising:

a) Providing a pharmaceutical composition comprising:
  (i) an organometallic complex of Formula I:

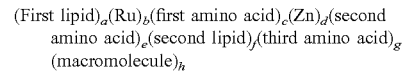

wherein the first lipid component comprises a sphingomyelin or a derivative thereof; the Ru signifies a ruthenium component; the first, second, and third amino acid components comprise an amino acid or a derivative thereof; the Zn signifies a zinc component; the second lipid component comprises a hydrocarbon chain of from 2 to twenty carbon atoms wherein at one end of the hydrocarbon chain (ω carbon) is a methyl group and at the other end (α carbon) is a carboxyl group; the macromolecule component comprises a polypeptide chain; wherein a, b, c, and h are at least 1; and d, e, f, and g are 0 or 1; wherein e, f, and g are 0 when d is 0, and g is 0 when f is 0; wherein the Ru component connects the sphingomyelin component with the first amino acid component; the Zn component connects the first amino acid component with one or more of the second amino acid component or fatty acid component; the third amino acid component is associated with the fatty acid component; the macromolecule component interacts with one or more of the first lipid component, the Ru component, the first amino acid component, the Zn component, the second amino acid component, the third amino acid component, or the second lipid component.

b) administering a therapeutic amount of the pharmaceutical composition to a mammal diseased with a tumor comprising tumor cells, wherein the therapeutic amount is effective to inhibit growth, proliferation, or both of the tumor comprising tumor cells.

In general, the pharmaceutical compositions of the present invention may be administered as described above. According to some embodiments, the complex in solution is present in an amount sufficient to produce a therapeutic effect after administration.

The organometallic complex, the ruthenium component, sphingomyelin component, zinc component, first, second, and third amino acid components, fatty acid component, and macromolecule component are as have been described above.

Structural and functional properties of the organometallic complex are as have been described above.

Combination Therapy

According to some embodiments, one or more of the organometallic complexes of the present invention can be administered in combination with one or more active agents. According to some embodiments, the active agents are administered as part of a single composition. According to some embodiments, the active agents are administered as separate compositions.

For example, one or more of the organometallic complexes of the present invention can be administered in combination with one or more chemotherapy agents. "Chemotherapy", in its most general sense, refers to the treatment of disease by means of chemical substances or drugs. In popular usage, it refers to antineoplastic drugs used alone or in combination as a cytotoxic standardized regimen to treat cancer.

Chemotherapy is employed as part of a multimodality approach to the initial treatment of many other tumors, including breast cancer, colon cancer and locally advanced stages of head and neck, lung, cervical, and esophageal cancer, soft tissue sarcomas, and pediatric solid tumors. The basic approaches to cancer treatment are constantly changing.

For example, chemotherapeutic drugs can be divided into several categories including, but not limited to, (1) alkylating agents; (2) antimetabolites; (3) natural products; (4) hormones and related agents; (5) biologics; and (6) miscellaneous agents.

1. Alkylating Agents and their Side-Effects

Alkylating agents used in chemotherapy encompass a diverse group of chemicals that have in common the capacity to contribute, under physiological conditions, alkyl groups to biologically vital macromolecules, such as DNA. For several of the most valuable agents, such as cyclophosphamides and nitrosoureas, the active alkylating moieties are generated in vivo after complex metabolic reactions. There are five major types of alkylating agents used in chemotherapy of neoplastic diseases: (1) nitrogen mustards; (2) ethylenimimes; (3) alkyl sulfonates; (4) nitrosoureas; and (5) triazenes. Examples of alklyating agents include, but are not limited to, cyclophosamide (Cytotaxan®), a synthetic alkylating agent chemically related to the nitrogen mustards; temozolomide (Temodar®), a triazene analog of dacarbazine; busulfan (Myleran®), a synthetic derivative of dimethane sulfonate; ifosfamide (Ifex®), a synthetic analog of cyclophosaphamide; mesna (Mesnex®), a sulfhydryl compound; melphalan hydrochloride (Alkeran®), an orally available phenylalanine derivative of nitrogen mustard; and the nitrosoureas carmustine (BiCNU®) and lomustine (CEENU®).

2. Antimetabolites

Antimetabolites are a class of drugs that interfere with DNA and RNA growth by preventing purines (azathioprine, mercaptopurine) or pyrimidine from becoming incorporated into DNA during the S phase of the cell cycle, thus stopping normal development and division. Antimetabolites commonly are used to treat leukemias, tumors of the breast, ovary and the intestinal tract, as well as other cancers.

Antimetabolites include folic acid analogs, such as methotrexate and aminopterin; pyrimidine analogs, such as fluorouracil and fluorodeoxyuridine; cytarabine (cytosine arabinoside); and purine analogs, such as mercaptopurine, thioguanine, fludarabine phosphate, pentostatin (2'-deoxycoformycin), and cladribine.

2.1. Anti-Folates

Folic acid is an essential dietary factor from which is derived a series of tetrahydrofolate cofactors that provide single carbon groups for the synthesis of precursors of DNA (thymidylate and purines) and RNA (purines). The enzyme dihydrofolate reductase ("DHFR") is the primary site of action of most anti-folates. Inhibition of DHFR leads to toxic effects through partial depletion of tetrahydrofolate cofactors that are required for the synthesis of purines and thymidylate.

Examples of anti-folates include, but are not limited to, methotrexate and Pemetrexed disodium. The most commonly used anti-folate is methotrexate (methotrexate sodium, amethopterin, Folex®, Mexate®, Rheumatrex®), which is an antimetabolite and antifolate agent with antineoplastic and immunosuppressant activities. Pemetrexed disodium (Alimta®) is the disodium salt of a synthetic pyrimidine-based antifolate.

2.2. Pyrmidine Analogs

Pyrmidine analogs are a diverse group of drugs with the capacity to inhibit biosynthesis of pyrimidine nucleotides or to mimic these natural metabolites to such an extent that the analogs interfere with the synthesis or function of nucleic acids. Drugs in this group have been employed in the treatment of diverse afflictions, including neoplastic diseases, psoriasis and infections caused by fungi and DNA-containing viruses.

Examples of pyrimidine analogs include, but are not limited to, 5-Fluorouracil (fluorouracil, 5-FU, Adrucil®, Efudex®, Fluorplex®), an antimetabolite fluoropyrimidine analog of the nucleoside pyrimidine with antineoplastic activity; floxuridine, a fluorinated pyrimidine monophosphate analogue of 5-fluoro-2'-deoxyuridine-5'-phosphate (FUDR-MP) with antineoplastic activity; capecitabine (Xeloda®), an antineoplastic fluoropyrimidine carbamate; and gemcitabine hydrochloride (Gemzar®), the salt of an analog of the antimetabolite nucleoside deoxycytidine with antineoplastic activity.

2.3. Purine Analogs

Several analogs of natural purine bases, nucleosides and nucleotides useful in the treatment of malignant diseases (mercaptopurine, thioguanine) and for immunosuppressive (azatioprine) and antiviral (acyclovir, ganciclovir, vidarabine, zidovudine) therapies have been identified.

The purine analogs mercaptopurine and its derivative azatioprine are among the most clinically useful drugs of the antimetabolite class. Examples of purine analogs include, but are not limited to, mercaptopurine (Purinethol®), a thiopurine-derivative antimetabolite with antineoplastic and immunosuppressive activities; decitabine (Dacogen®), a cytidine antimetabolite analogue with potential antineoplastic activity; and dacarbazine (DTIC-DOME®), a triazene derivative with antineoplastic activity.

3. Natural Products

Many chemotherapeutic agents are found or derived from natural resources. Antimicrotubule molecules, such as paclitaxel or *vinca* alkaloids, can cause sinus bradycardia, atrioventricular block, ventricular tachycardia, hypotension, congestive heart failure and ischemia. See Yeh, E T, et al., Circulation 109 (25): 3122-31 (2004). Mitomycin, for example, has been associated with the development of caradiomyopathy, especially when given with or after an anthracycline. Buzdar, A. U., et al. Cancer Treat. Rep. 62: 1005-1008 (1978).

3.1. Antimitotic Drugs

3.1.1. Vinca Alkaloids and their Side-Effects

The *vinca* alkaloids, cell-cycle-specific agents that, in common with other drugs, such as colchicine, podophyllotoxin, and taxanes, block cells in mitosis, exerts their biological activities by specifically binding to tubulin, thereby blocking the ability of protein to polymerize into microtubules, and arresting cell division in metaphase through disruption of the microtubules of the mitotic apparatus. In the absence of an intact mitotic spindle, the chromosomes may disperse throughout the cytoplasm or may clump in unusual groupings. Both normal and malignant cells exposed to *vinca* alkaloids undergo changes characteristic of apoptosis.

Examples of *vinca* alkaloids include, but are not limited to, vincristine sulfate, a salt of a natural alkaloid isolated from the plant *Vinca rosea* Linn; vinblastine, a natural alkaloid isolated from the plant *Vinca rosea* Linn; and vinorelbine. Both vincristine and vinblastine, as well as the analog vinorelbine, have potent and selective antitumor effects, although their actions on normal tissue differ significantly.

3.1.2. Taxanes

The taxanes include, for example, but not limited to, paclitaxel, extracted from the Pacific yew tree *Taxus brevifolia*, and docetaxel (Taxotere®), a semi-synthetic, second-generation taxane derived from a compound found in the European yew tree *Taxus baccata*.

3.2. Epipodophyllotoxins and their Side-Effects

Podophyllotoxin is the active principle extracted from the mandrake plant *Podophyllum peltatum* from which two semisynthetic glycosides, etoposide and teniposide, have been developed.

3.3. Camptothecin Analogs and their Side-Effects

Camptothecins target the enzyme topoisomerase I. The parent compound, camptothecin, was first isolated from the Chinese tree *Camptotheca acuminata*. Although the parent camptothecin compound demonstrated antitumor activity, its severe and unpredictable toxicity, principally myelosuppression and hemorrhagic cystitis limited its use. The most widely used camptothecin analogs are irinotecan and toptecan, which are less toxic and more soluble.

3.4. Antibiotics and their Side-Effects

Antitumor antibiotics are compounds that have cytotoxic as well as antimicrobial properties. Most commonly used in neoplastic disease treatment are the actinomycins and anthracyclines.

Anthracyclines are known to generate congestive heart failure and left ventricular dysfunction in susceptible patients. The occurrence of congestive heart failure is dose- and schedule-dependent. Left ventricular dysfunction is observed more frequently in women, in patients with a personal history of cardiac disease, and after mediastinal X-ray therapy. Yeh, E T, et al, Circulation 109(25): 3122-31 (2004). Mitroxantrone, which is a derivative of anthraquinone (9,10 dioxoantrhacene, also known as 9,10-anthracenedione, anthradione, 9,10-anthrachinon, anthracene-9,10-quinone, 9,10-dihydro-9,10-dioxoanthracene, and trade names Hoelite, Morkit and Corbit), induces acute myocarditis and arrhythmia during infusion. Albini, et al., J. Natl Cancer Instit. 102(1): 14-25 (2010).

3.4.1. Actinomycin

An exemplary actinomycin includes Dactinomycin (Actinomycin D), produced by *Streptomyces parvullus*. This highly toxic agent inhibits rapidly proliferating cells of normal and neoplastic origin.

3.4.2. Anthracyclines

The anthracycline antibiotics and their derivatives are important antitumor agents. They are produced by the fungus *Streptomyces peucetius* var. *caesius*. Anthracyclines and anthracenediones can intercalate with DNA. Accordingly, many functions of DNA are affected, including DNA and RNA synthesis. Single-strand and double-strand breaks occur, as does sister chromatid exchange; thus these compounds are both mutagenic and carcinogenic. Scission of DNA is believed to be mediated by drug binding to DNA and topoisomerase II that prevents the resealing of DNA breaks created by the enzyme.

Examples of anthracyclines include, but are not limited to, idarubicin hydrochloride, a semisynthetic 4-demethoxy analog of daunorubicin (daunorubicin hydrochloride, daunomycin, rubidomycin; Cerubidine®); doxorubicin (doxorubicin hydrochloride, Adriamycin®, Rubex®); as well as several analogs of doxorubicin including valrubicin (Valstar®) (for intravescial therapy of BCG-refractory urinary bladder carcinoma) and epirubicin (4'-epidxorubicin, Ellence®) (as a component of adjuvant therapy following resection of early lymph-node-positive breast cancer).

Additional antibiotic antineoplastics include, but are not limited to, mitoxantrone (Novotrone®), an anthracenedione; and bleomycin antibiotics, fermentation products of *Streptomyces verticillus* that cleave DNA, and includes bleomycin sulfate (Blenoxane®); and mitomycin (mitomycin-C, Mutamycin®), an antibiotic isolated from *Streptomyces caespitosus*.

4. Biologics

Generally, the term "biologics" refers to compounds that are produced by biological processes, including those utilizing recombinant DNA technology. Biologic compounds include agents or approaches that beneficially affect a patient's biological response to a neoplasm. Included are agents that act indirectly to mediate their anti-tumor effects (e.g., by enhancing the immunological response to neoplastic cells) or directly on the tumor cells (e.g., differentiating agents). Examples of antineoplastic biologics include, but are not limited to, Filgrastim (Neupogen®), a recombinant granulocyte colony-stimulating factor (G-CSF); and Sargramostim (Leukine®), a recombinant granulocyte/macrophage colony-stimulating factor (GM-CSF).

Examples of antineoplastic monoclonal antibodies include, but are not limited to, Bevacizumab (Avastin®), a recombinant humanized monoclonal IgG1 antibody that binds to and inhibits the biologic activity of human vascular endothelial growth factor ("VEGF") in in vitro and in vivo assay systems, and Panitumumab (Vectibix®), a human monoclonal antibody produced in transgenic mice that attaches to the transmembrane epidermal growth factor (EGF) receptor. The risk of cardiotoxic adverse events increases when anthracycline chemotherapy is admiistered concurrently or sequentially before adjuvant therapy with trastuzumab, a monoclonal antibody specific for the HER2 protein. Popat, S., Sith I E, natl Clin. Pract. Oncol. 5(6): 324-35 (2008).

5. Hormones and Related Agents

Several chemotherapeutic agents exert their therapeutic effect through interactions with hormones and related agents. Antiestrogens are modulators of the estrogen receptor. Estrogens are the family of hormones that promote the development and maintenance of female sex characteristics.

Examples of antiestrogens include, but are not limited to, tamoxifen citrate (Nolvadex®), a competitive inhibitor of estradiol binding to the estrogen receptor ("ER").

Gonadotropin-releasing hormone ("GnRH") analogs are synthetic peptide drugs modeled after human GnRH. They are designed to interact with GnRH receptor. The analogs of GnRH peptide include leuprolide (Lupron®, Eligard®), goserelin (Zoladex®), triptorelin (Trelstar Depot®) and buserelin (Suprefact®).

Examples of gonadotropin-releasing hormone analogs include Leuprolide acetate, the salt of a synthetic nonapeptide analog of gonadotropin-releasing hormone.

Examples of antineoplastic androgens include, but are not limited to, fluoxymesterone (Halotestin®), a halogenated derivative of 17-alpha-methyltestosterone. Additional anti-androgen agents, include, but are not limited to, megestrol acetate, the salt of megestrol, a synthetic derivative of the naturally occurring female sex hormone progesterone, with progestogenic, antiestrogenic, and antineoplastic activities.

Examples of somatostatin analogs include, but are not limited to, octreolide acetate (Sandostatin LAR® Depot), the salt of a synthetic long-acting cyclic octapeptide with pharmacologic properties mimicking those of the natural hormone somatostatin.

6.1. Kinase Inhibitors

Antineoplastic kinase inhibitors include, but are not limited to, Sorafenib tosylate (Nexavar®), a synthetic compound that targets growth signaling and antiogenesis, and Erlotinib hydrochloride (Tarceva®), the salt of a quinazoline derivative with antineoplastic properties.

6.2. Platinum Coordination Complexes

Examples of antineoplastic agents that form platinum coordination complexes include, but are not limited to, Cisplatin (cis-diamminedichloroplatinum (II), Platinol-AQ®), a divalent inorganic water-soluble, platinum containing complex that appears to enter cells by diffusion and reacts with nucleic acids and proteins, is a component of several combination chemotherapy regimens. For example, it is used with bleomycin, etoposide and vinblastine for treating patients with advanced testicular cancer, and with paclitaxel, cyclophosphamide or doxorubicin for treating ovarian cancer.

Another antineoplastic agent that forms a platinum coordination complex is Carboplatin (CBDCA, JM-8), which has a mechanism and spectrum of clinical activity similar to cisplatin, but generally is less reactive than cisplatin.

An additional antineoplastic agent is Oxaliplatin (trans-1-diaminocyclohexane oxalatoplatinum), which, like cisplatin, has a wide range of antitumor activity and is active in ovarian cancer, germ-cell cancer and cervical cancer. Unlike cisplatin, oxaliplatin in combination with 5-fluorouracil is active in colorectal cancer.

6.3. EDTA Derivatives

Other antineoplastic agents include EDTA-derivatives. Such compounds include, but are not limited to, Dexrazoxane hydrochloride (Zincard®), the salt of a bisdioxopiperazine with iron-chelating, chemoprotective, cardioprotective, and antineoplastic activities.

6.4. Platelet-Reducing Agent

Anagrelide hydrochloride (Agrlyin®) is a platelet-reducing agent used to treat thrombocythemia, secondary to myeloproliferative disorders, to reduce the elevated platelet count and the risk of thrombosis and to ameliorate associated symptoms including thrombo-hemorrhagic events.

6.5. Retinoids

Retinoids are a group of substances related to vitamin A and function like vitamin A in the body. Retinoids include, but are not limited to, bexarotene (Targretin®), a synthetic retinoic acid agent with potential antineoplastic, chemopreventive, teratogenic and embryotoxic properties; and isotretinoin (Accutane®), a naturally-occurring retinoic acid with potential antineoplastic activity.

6.6. Histone Deacetylase Inhibitors

The histone deacetylase inhibitor vorinostat (Zolinza®) is a synthetic hydroxamic acid derivative with antineoplastic activity, and a second generation polar-planar compound that binds to the catalytic domain of the histone deacetylases (HDACs). This allows the hydroxamic moiety to chelate zinc ion located in the catalytic pockets of HDAC, thereby inhibiting deacetylation and leading to an accumulation of both hyperacetylated histones and transcription factors. Hyperacetylation of histone proteins results in the upregulation of the cyclin-dependent kinase p21, followed by G1 arrest. Hyperacetylation of non-histone proteins such as tumor suppressor p53, alpha tubulin, and heat-shock protein 90 produces additional anti-proliferative effects. Vorinostat also induces apoptosis and sensitizes tumor cells to cell death processes.

One or more of the organometallic complexes of the present invention can be administered in combination with agents that cause a change to chromatin structure. Exemplary chromatin remodeling agents include agents undergoing clinical trials such as Vorinostat, Romidepsin, Panobinostat, Valproic acid, Belinostat, Mocetinostat (MGCD0103), Abexinostat (PCI-24781), Entinostat (MS-275), SB939, Resminostat (4SC-201), Givinostat (ITF2357), Quisinostat (JNJ-26481585), Kevetrin, CUDC-101, AR-42cite_note-46, CHR-2845, CHR-3996cite_note-50, 4SC-202, CG200745, ACY-1215, ME-344, sulforaphanecite_note-Tan2010-34, and Givinostat (ITF2357).

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges which may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and described the methods and/or materials in connection with which the publications are cited.

It must be noted that as used herein and in the appended claims, the singular forms "a", "and", and "the" include plural references unless the context clearly dictates otherwise. All technical and scientific terms used herein have the same meaning.

The publications discussed herein are provided solely for their disclosure prior to the filing date of the present application and each is incorporated by reference in its entirety. The dates of publications provided may be different from the actual publication dates which may need to be independently confirmed.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to number used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

The method of synthesis described below uses two stages for the solubilization of sphingomyelin. This method ultimately achieves a spin complex of ruthenium sphingomyelin as shown by electron spin resonance spectroscopy (ESR)

Figure 12:
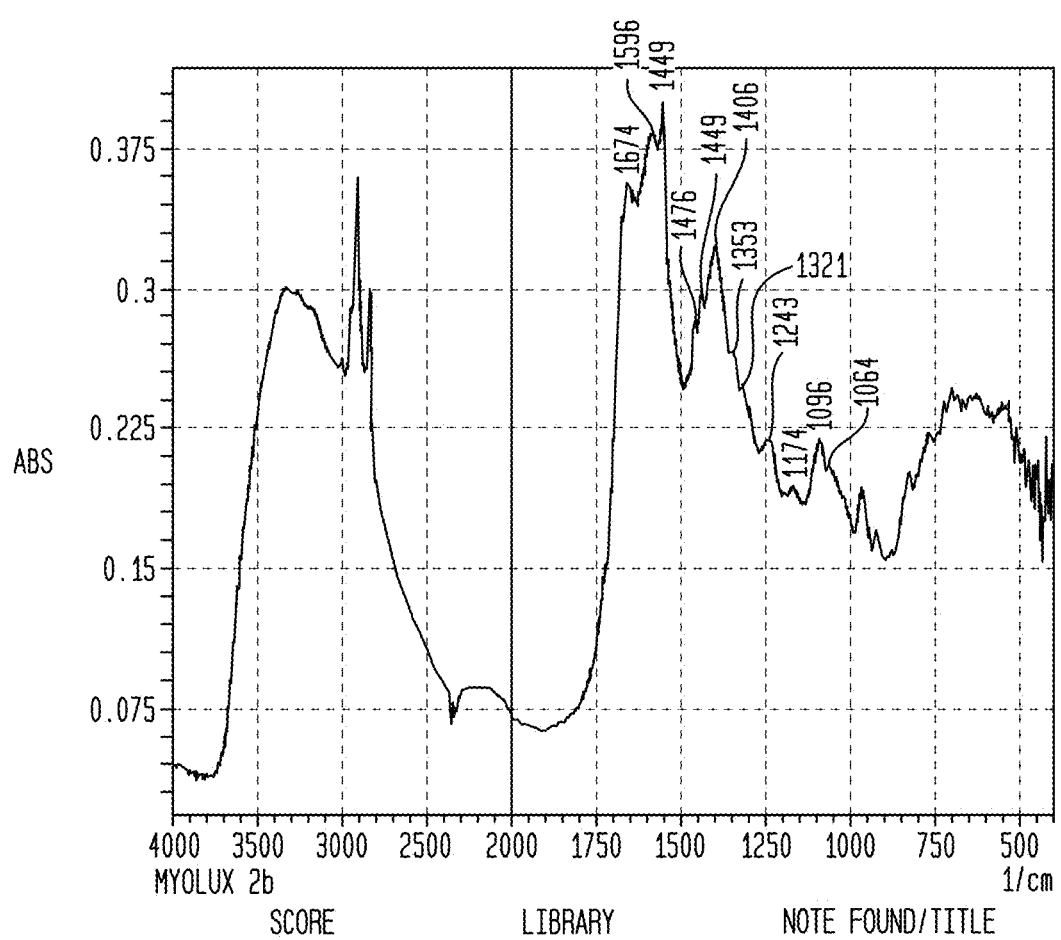
FIG. 12 depicts an FTIR Spectrum of GML0003 ("Myelux™") (comprising ruthenium formyl methionine and sphingomyelin). A peak at 1596 $cm^{-1}$ appears and represents formation of a bond between Ruthenium and the Sphingomyelin carbonyls. This peak will be obscured during subsequent steps of the synthesis of Toroglobulin™ as it is hidden in the spectral overlaps.

(FIG. 7), along with data for ruthenium to sphingomyelin bonding as shown by FTIR (FIG. 12—Myelux™ stage of synthesis). By means of that spin coupling, the signaling of sphingomyelin is shown to act in a robust electroactive form (FIG. 1). We call the final complex Toroglobulin™. Toroglobulin™ is shown to be a strong reducing agent of Histone IIS by cyclic voltammetry (FIG. 1). Without being limited by theory, this electronic reduction of Histone IIS is proposed to enable nucleosome formation.

Example 1. Making the Organometallic Complex

Method of Synthesis of Toroglobulin

All reactants were obtained from Sigma unless otherwise indicated and were reagent grade, except for the $ZnCl_2$ which was USP grade. The reactions were carried out in purified water. Three feedstock solutions were first prepared. Using sphingomyelin as the starting material, the three feedstock solutions were sequentially introduced and reacted. The product is then reacted with gamma globulin (Sigma, Cat. No. G-4386).

The three prepared feedstock solutions were: (1) solubilized linoleic acid (ALI); (2) Ruthenium-formyl methionine complex (RUF); and (3) zinc bis-threonine complex (ZBT).

1. Method for Making 1 Liter of 0.06M Arginine-Linoleic Acid (ALI)—First Feedstock Solution.

11.0 g or 0.063 moles L-arginine base (Sigma) (FW 174.2 g/mole) was dissolved in 800 mL purified $H_2O$ by stirring in a 2 liter beaker with a magnetic stir bar. 16.8 g of linoleic acid or 0.06 mole (Alfa Aesar) (FW 280.5 g/mole) was added with vigorous stirring for five minutes until a smooth white gel was obtained. 11.25 mL of 6 N or 0.0675 mole NaOH (Baker) was added and stirred until clear. Sufficient water to make the total volume 1000 mL was added and stirred until clear. The resulting solution was bottled and labeled as 0.06 M Arginine-Linoleic—First Feedstock Solution (ALI). Refrigerate.

Contents of First Feedstock Solution (ALI):

| Material | Concentration |
|---|---|
| Linoleic acid | 0.06M |
| Na+ | 0.0675M |

2. Method for Making 1800 mL Ruthenium-Formyl Methionine Complex (RUF)-Second Feedstock Solution.

1 liter of distilled water was placed in a 4 liter beaker. 42.012 g or 0.2371 mole N-formyl-L-methionine (FW 177. g/mole) was then added. The solution was stirred by a magnetic stirrer until dissolved. 6.372 g or 0.0244 mole $RuCl_3 \cdot XH_2O$ (X≤1) (FW 207.43+54.0 g/mole) was then added, followed by stirring to dissolve. The solution was then heated to boiling and boiled for about 5 minutes. The solution was then cooled overnight.

50 mL 6N NaOH was added to the solution to adjust the pH to about 7.8. Water was then added to adjust the final volume to 1800 mL, and stirred well. The solution was then labeled—Second Feedstock Solution (RUF).

Constituents:

| Material | Concentration | |
|---|---|---|
| $RuCl_3 \cdot 3H_2O$ = (6.372/261.43)/1.8 | = 0.01354M | = 0.014M |
| N-formyl-L-methionine = (42.012/177.2)/1.8 | = 0.13172M | = 0.13M |
| Na+ = (6 × 0.05)/1.8 | = 0.1667M | |
| Cl- = 3 × Ru = 3 × 0.01354 | = 0.0406M | |
| Ru: N-formyl-L-methionine | = 1:9.73 | |

3. Method for Making Zinc Bis-Threonine Complex—Third Feedstock Solution (ZBT).

50 g $ZnCl_2$ was weighed and transferred to a 2 Liter beaker over a magnetic stirrer. Purified water is added to achieve 1 liter. The stock solution was stirred vigorously until clear. (Since 50 mg/ml $ZnCl_2$=0.365 M $ZnCl_2$)

To make a 0.01 M solution of Zn bis threonine, the stock of 0.365 M $ZnCl_2$ was diluted by 36.5× in the final.

FW of L-threonine is 119.1; 0.01 M threonine will contain 1.191 mg/mL. A planned bis solution with two threonine equivalents will contain 2.382 mg/mL threonine. 365 mL of a 0.02 M bis solution will contain 869.43 mg threonine.

869.43 mg of L-threonine was weighed out and added to 300 ml of purified water in a liter beaker over a magnetic stirrer. The threonine was stirred until dissolved.

10 ml of stock 0.365 M $ZnCl_2$ was added to the threonine solution and stirred thoroughly. Water was added to a final volume of 365 ml. The pH of this solution was slightly acidic.

The resulting solution was labeled as 0.01 M Zn bis-threonine—Third Feedstock Solution (ZBT), and refrigerated.

Assembly from Sphingomyelin and Three Feedstock Solutions (Toroidin™ Stage):

During synthesis of the complex, sphingomyelin was uniformly dispersed by mixing with an arginine-linoleic acid liquid conjugate. By thoroughly mixing arginine-linoleic acid liquid complex, with sphingomyelin powder, an opaque white gel was achieved. 1.0 g Sphingomyelin (Sigma) was placed in a 1 liter beaker. 94.0 mL of 0.06 M arginine-linoleic acid solution (ALI) was added, and stirred and heated to disperse. Next, 47.0 mL of 0.014 M Ru-formyl methionine (as 1:9.8) (RUF) was added. 188.0 ml of water was then added. The solution was then stir-boiled for three minutes until the solution converted to a violet color. Water was then added for a final volume of 376 ml. This solution containing sphingomyelin-arginine-linoleic acid-Ruthenium-N-formyl Methionine was called GML0003 ("Myelux™").

Assembly of Toroidin™

376 mL of Myelux™ solution was placed in a 1 liter beaker in a water bath. 125.33 mL of 0.01 M Zn bis threonine (ZBT) was added. Next, 12.53 mL 6 N NaOH was added. This mixture was stirred with a magnetic stirrer. The mixture was then boiled for 5 minutes, turning the solution blue. Water was then added to bring the final volume to 514 ml, stirred, and allowed to cool.

The solution, which is a ZBT complex of ALI-RUF-sphingomyelin, is termed GML0002 ("Toroidin™") and contains sphingomyelin-arginine-linoleic acid-ruthenium-N-formyl methionine-zinc-threonine. The initial microscopic liquid crystal appearance of the material is that of toroids or donut shapes. Toroids are a vortex form.

The combined product sub-complex, Toroidin™, showed powerful anti-tumor properties in cell culture (See below). However this product, which forms microscopic toroids, was associated with seizures in mice. The seizures were eliminated by complexing Toroidin™ with gamma globulin. This electronic filtration by gamma globulin is in a new area of fundamental science which studies the waveguide properties of peptides. This safer final derivative is called GML0001 ("Toroglobulin™").

Assembly of Toroglobulin

Human gamma globulin (Sigma, Cat. No. G4386) was dissolved in purified water with stirring to make 514 ml of solution at a concentration of 5 mg/ml. A trace of NaOH was required for solubility. This 5 mg/ml gamma globulin solution was combined with an equal volume of the Toroidin™ solution, and mixed for two hours with a magnetic stirrer.

The resulting blue solution of Toroidin™ and gamma globulin was filtered and stored in bottles filled to the top to exclude air, and refrigerated.

The 1028 mL solution contained 7.7622 g of material exclusive of the NaCl. This 7.55 mg/mL solution was labeled "Unfinished Toroglobulin™ Solution for Processing". The material was then lyophilized, which finalizes the coordination chemistry. The lyophilized powder was stored in a sealed bag to exclude air, and labeled "Lyophilized Toroglobulin™". This power was refrigerated.

Resolubilization of the Lyophilized Powder

A solution of 20 mg/ml concentration was prepared for experimentation. 800 mg of lyophilized powder was combined with 30 ml of water and mixed with a magnetic stir bar until clear. The pH of this solution was about 12.4.

pH was adjusted with HCl. 3.2 ml of 1 N HCl was added and stirred, making the pH about 8.8. Water was then added to a final volume of 40 nil, and stirred. The color of this solution is blue-violet.

The solution was then run through a sterile filter with a 0.2 micron membrane. The filtered solution was inserted into sterile vaccine bottles leaving space for expansion when frozen, and labeled "Toroglobulin™ 20.0 mg/ml". Bottles were kept frozen on their sides until time of use.

Example 2—Characterization of Toroglobulin (Containing Sphingomyelin-Arginine-Linoleic Acid-Ruthenium-N-Formyl Methionine-Zinc-Threonine-Gamma Globulin)

Without intending to be limited by theory, it is believed that the described invention functions via vortices that arise from magnetic molecules. These involve magnetic field curvatures, for example, in solutions of ruthenates, which result in a 2-d spiral vortex appearance, and the hexagonal honeycomb vortex lattice predicted by magnetic vortex theory.

Figure 3:
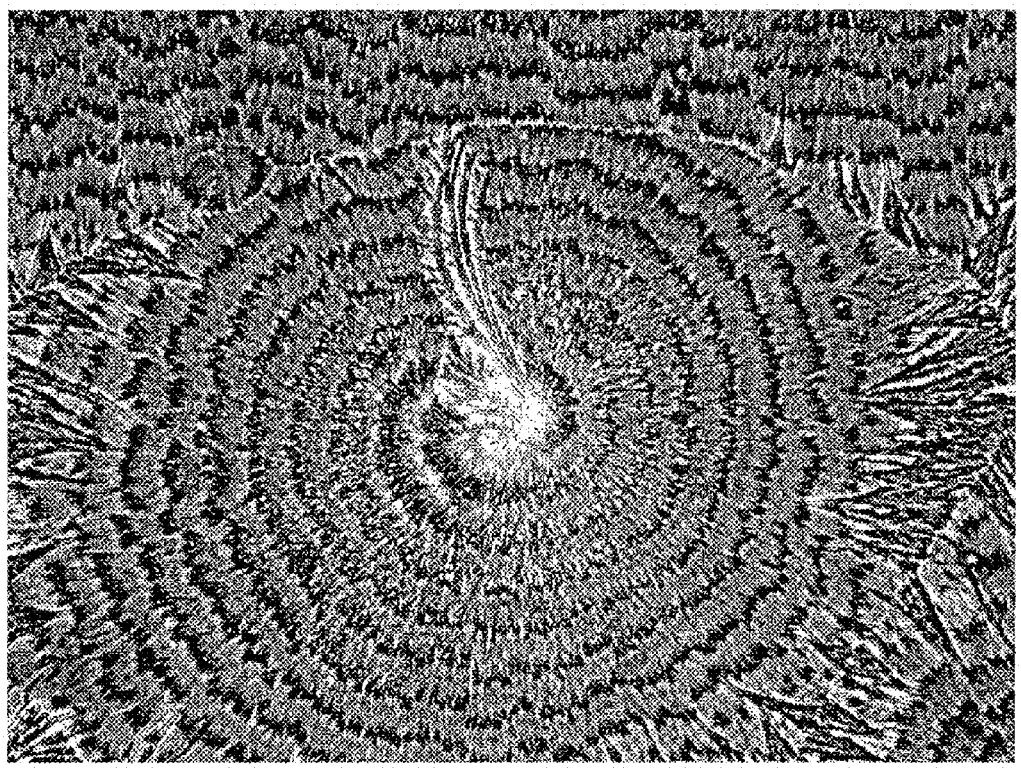
FIG. 3 depicts an example of "pinning" Myelux™ in glycine solution, viewed under 300× magnification. By pinning Myelux™ in glycine solution, a 2-d vortex is revealed. The image of FIG. 3 shows 1 µl of aqueous Melux solution (5 mg/mL) mixed into 10 µl of glycine solution (5.0 mg/mL) and then spread to dry on a glass slide.
Figure 4:
FIG. 4 shows a dense field of Toroglobulin™ pinned in glycine solution revealing an orderly series of ring structures arranged in cylindrical alignment consistent with periodically aligned vortex subunits.
Figure 6:
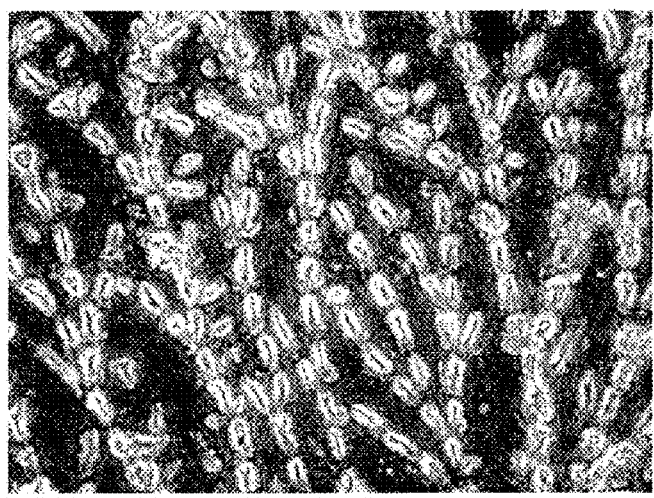
FIG. 6 shows the subunits of the vortex phase state of Myelux™ captured during formation by "pinning" in glycine, viewed at 800× magnification. At this magnification, the Myelux™ subunits appear arranged as parallel curved filaments, which elongate over time. Without being limited by theory, it is believed that the curvature of the filaments is determined by the intrinsic magnetic field.

Without intending to be limited by theory, this invention describes the use of a magnetic vortex phase in a biochemical reaction. The magnetic vortex has been extensively presented by Sandier and Serfaty. [Sandier, E., Serfaty, S., Vortices in the Magnetic Ginzburg-Landau Model, Birkhauser, Boston-Basel-Berlin, 2007]. A theoretical model for this particular molecular magnetic vortex would contain three stages implied by the microscopic images: The first is the assembly of filaments from spin active molecular subunits (FIG. 6). The second is filament curvature from the influence of intrinsic magnetic field lines. The curved filaments achieve the Ginzburg-Landau spiral 2-d form (FIG. 3). The third vector is an energy exchange with gamma globulin, forming a third axis and the unusual 3-d tunnel vortex configuration (FIG. 4). This third axis may be driven by a transverse Hall voltage or some other electronic modulation.

Phase Microscopy

Figure 2:
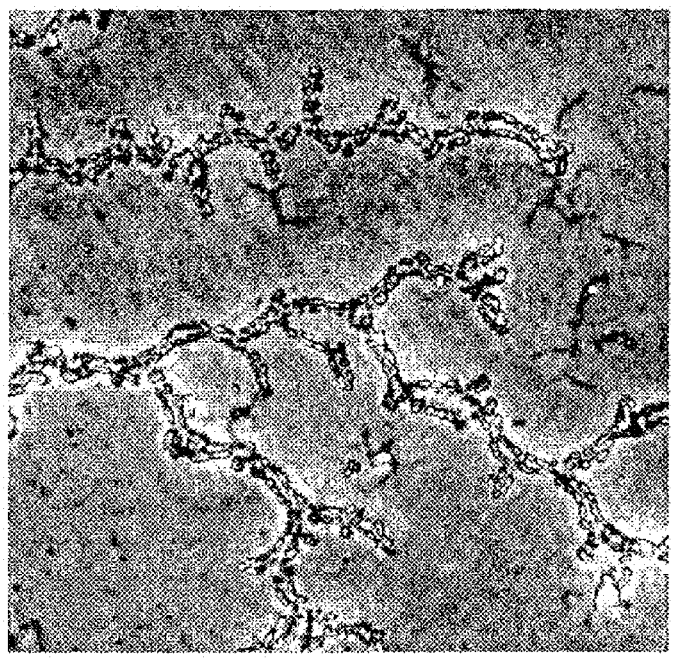
FIG. 2 depicts an exemplary liquid crystal form of 5 mg/mL GML0003 ("Myelux™") solution, examined under 300× phase microscopy, showing a pattern of fragmented hexagons in an incomplete lattice. 1 µl of solution was spread on a dry glass slide for visualization.

A solution of Myelux™ organometallic complex was prepared as described above. A 1 μl sample of Myelux™ was spread on a glass slide and viewed under low power (300×) phase microscopy. The liquid crystal form of Myelux™ shows fragmented hexagons in an incomplete lattice. See FIG. 2.

"Pinning" constitutes localization and energy transfer. Without being limited by theory, images of pinned compounds may reveal underlying field patterns. Vortex materials can be protected from dissipation of current by localizing and aligning in materials or matrices that have suitable cavities and symmetries called defects. Such materials are called pinning matrices. Pinning reactions vary with the nature of the materials. Pinning of vortices drops current density below a critical value.

A new method of vortex pinning was utilized in the current study to visualize the possible existence of magnetic vortices associated with Myelux™ and Toroglobulin™ compounds. Vortex pinning in the context of superconductors has been described previously. [Embon, L. et al., Probing dynamics and pinning of single vortices in superconductors at nanometer scales, Nature.com, Scientific Reports 5, Article no.: 7598 (2015) doi:10.1038/srep07598, January 2015]

Here, a glycine, water solution was used as a pinning agent for the compounds. The phase contrast microscopy images revealed that the glycine solution enables the formation of 2-d spiral vortices of the Myelux™ composition (FIG. 3), which is not visible in the unmixed reactants. Without being limited by theory, this pinning method functions to reveal macromolecular arrays in a thin film on a glass slide. The two-dimensional spiral vortex shown in FIG. 3 is that of the core compound Myelux™ stage of the described invention. To obtain this image, 1.0 uL of aqueous Myelux™ solution (5.0 mg/mL) was mixed into 10 uL glycine solution (5.0 mg/mL) and then spread to dry on a glass slide. The Myelux™ was then viewed by phase contrast microscopy (300× magnification) after "pinning" in the glycine solution. See FIG. 3. FIG. 3 shows a 2-d spiral form of the core Myelux™ compound, with some new fibers being expelled from the center of the spiral.

Toroglobulin™ was also viewed by phase contrast microscopy at 800× magnification after "pinning" it in a glycine solution. FIG. 4 shows a phase contrast image of the resulting pinned sample. A dense field of parallel loops is present, resembling a vortex structure. In a watery solution, the liquid crystal form of Toroglobulin™ reveals a vortex field pattern seen as a tunnel (FIG. 4).

Figure 5:
FIG. 5 depicts an example of dry lyophilized Toroglobulin™ showing a microscopic honeycomb lattice pattern viewed under 30× magnification.

Dry lyophilized Toroglobulin™ was also viewed by phase contrast microscopy at 30× magnification. As seen in FIG. 5, dry lyophilized Toroglobulin™ is seen as having a complex crystalized structure with multiple branching units. In many instances this crystalized structure takes on a cyclical, honey comb-like structure. The repeating cyclical structures appear to be present in both two-dimensional and three-dimensional space. Without being limited by theory, this honeycomb-like lattice may indicate that a high energy vortex phase can be expressed.

Figure 7:
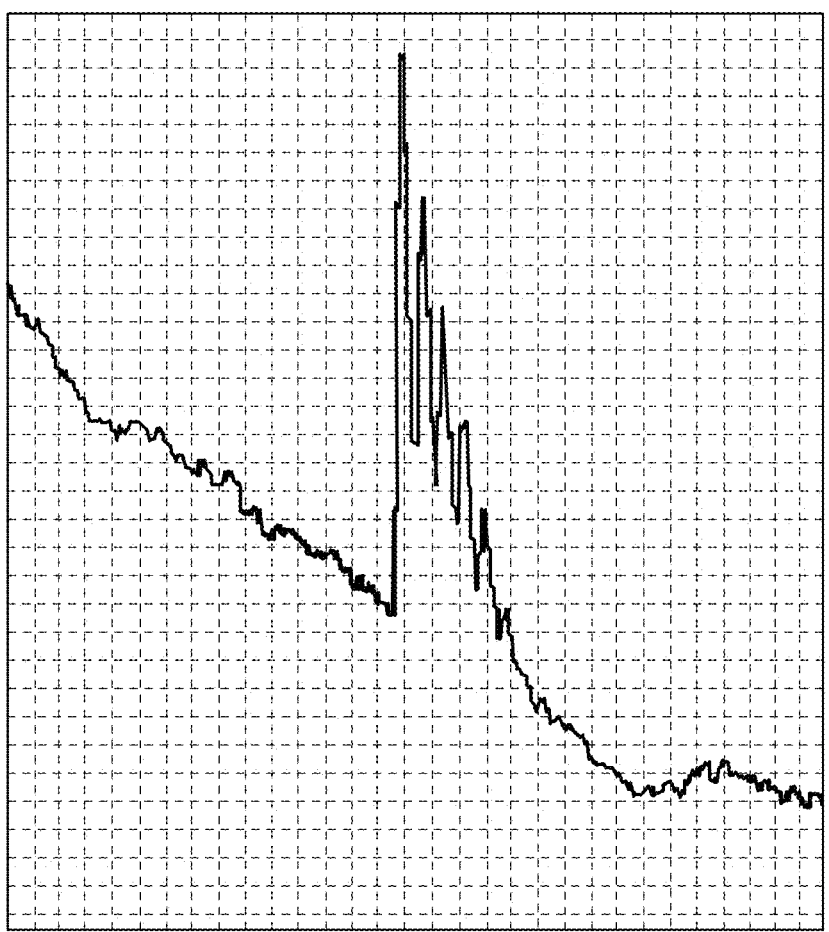
FIG. 7 shows the electron spin resonance (ESR) of Toroglobulin™ with Histone IIS, with DNA and NaCl, as measured on a Resonance Model 8400 EPR X Band Spectrometer. The splitting constant is 10.3 Gauss on the horizontal axis. The vertical axis is the signal strength of the X-band spectrometer in non-calibrated instrument units. The horizontal axis is the magnetic field strength in Gauss units. A sextet of lines is shown indicating superhyperfine splitting. Interaction of the ligand field electrons with multiple nuclei is indicated. The ESR sample is prepared in a 5.0 mL test tube by adding 300 µl of Toroglobulin™ (5 mg/mL), calf thymus DNA (5 mg/mL; Sigma Cat. No. D1501), Histone IIS (5 mg/mL, Sigma), and NaCl (0.9% aqueous solution). After thorough mixing 1 µl of the mixture was pipetted into an NMR tube and then frozen overnight. The frozen NMR tube was transferred directly from the freezer to the ESR spectrometer for assay.

FIG. 6 shows a view of pinned Toroglobulin™ by phase contrast microscopy at 800× magnification. The image reveals generally parallel, branching filaments comprised of repeating globular subunits. This is the first stage in the vortex formation, where the associated subunits are presumed to be spin magnetic. These subunits assemble into long curved filaments. The filament curvature is attributed to the formation of intrinsic magnetic fields. The spin force is believed to arise by resonant D-orbital precession in the ruthenium-to sphingomyelin coordination structure. The vortex induction is associated with an electron spin resonance (FIG. 7).

Voltammetry

Voltammetry of Toroglobulin™ was also performed using an EG&G Parstat potentiostat using a gold working electrode, a platinum counter electrode, and an Ag/KCl reference electrode. Nitrogen purging was performed for ten minutes.

Toroglobulin™ was shown to be a strong reducing agent of Histone IIS. FIG. 1 depicts a cyclic voltammetry experiment wherein energy transfer of Toroglobulin™ alone or Toroglobulin™ with histone IIS was tested. The energy transfer plot of Toroglobulin™ alone is represented by line (a) showing a +68 mv energy peak. The energy transfer of Toroglobulin™ with histone IIS is represented by line (b) showing an energy peak of +484 my. The remaining lines of the figure are return scans that were not contributory. Furthermore, the current density of Toroglobulin™ and histone IIS is diminished at its peak. These data suggest that Toroglobulin™ is acting as a histone reductase and the histone is acting as an electron acceptor.

Electron Spin Resonance

The interaction of Toroglobulin™ with histone IIS was further characterized by electron spin resonance experiments. The electron spin resonance of Toroglobulin™ with histone IIS was measured using a Resonance Model 8400 EPR X Band Spectrometer. The spin resonance analysis of Toroglobulin™ with histone IIS shows a sextet of lines indicating superhyperfine splitting, and indicating interaction of the ligand field electrons with multiple nuclei. See FIG. 7. The horizontal ESR x-axis is the magnetic field strength. The vertical ESR y-axis is signal strength in relative instrument units, which are not calibrated in this convention. The splitting constant was 10.3 Gauss on the horizontal axis.

Electrophoresis

Figure 8:
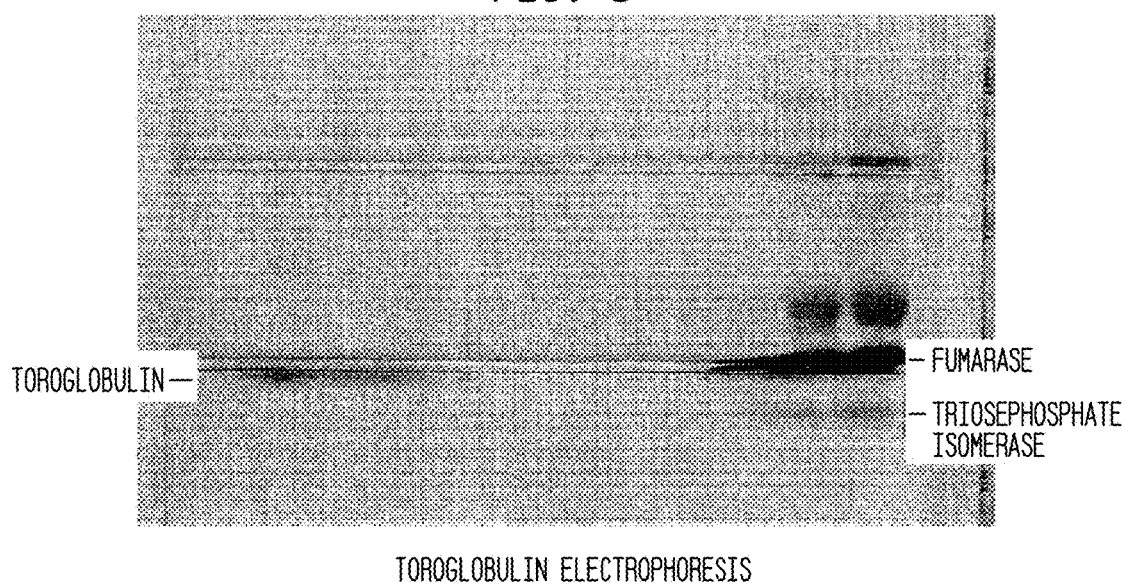
FIG. 8 depicts SDS gel electrophoresis of Toroglobulin™. Molecular weight markers were obtained from Sigma. A Novex electrophoresis system was used with Nupage gel plates. A tris-glycine sodium dodecyl sulfate running buffer was used. Molecular weight markers were run in tandem with Toroglobulin™. The molecular weight of Toroglobulin™ is close to, but less than, the closest marker, which is Fumarase having a molecular weight of 48,500. Toroglobulin™ weighs less than 48,500, and more than the second nearest marker, triosephosphate isomerase, which weighs 26,600. The molecular weight of Toroglobulin™ was interpolated from the electrophoresis grid background with the two markers. The weight of Toroglobulin™ is estimated to be near 43,000. Only a single form of Toroglobulin™ is detected.

The Toroglobulin™ complex was also characterized by electrophoresis. FIG. 8 depicts the electrophoretic mobility of Toroglobulin™ and pre-stained protein size standards (Sigma) using a Novex system with Nupage gel plates. A tris-glycine sodium dodecyl sulfate running buffer was used. A single band having a molecular weight of approximately 43 kDa was seen. This single band is labeled Toroglobulin™ in FIG. 8. Protein size standards comprised fumarase (~48.5 kDa) and triosephosphate isomerase (~26.6 kDa), which are also indicated in FIG. 8. The results of the electrophoresis indicate that only a single form of Toroglobulin™ is present.

UV-Visible Spectroscopy

Figure 9A:
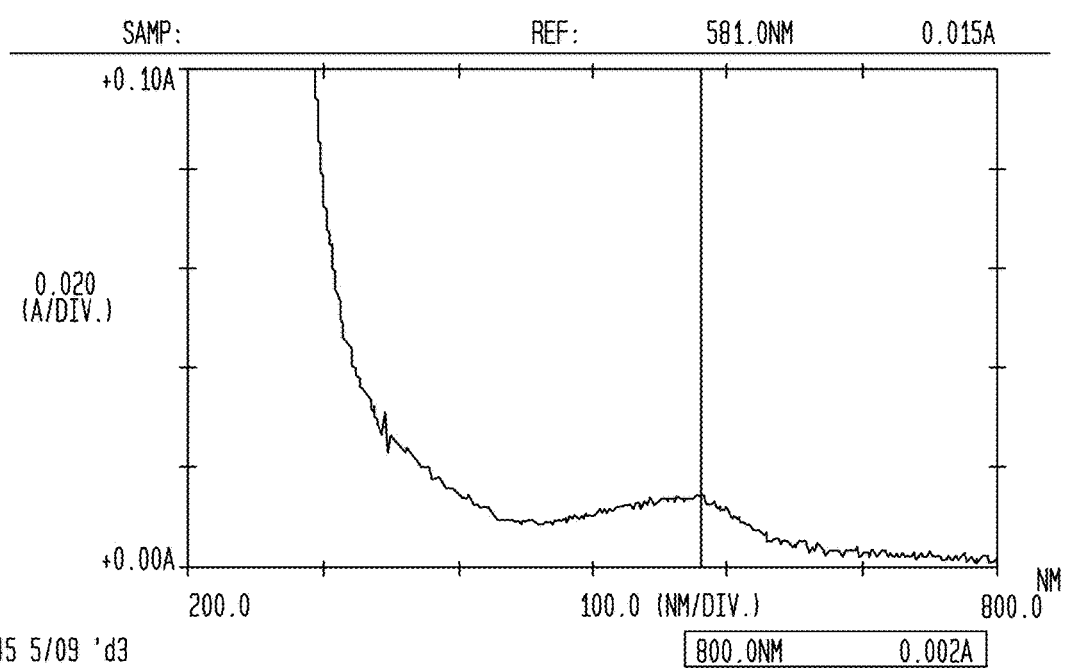
FIG. 9 shows UV-Visible spectra of Toroglobulin™ in water, examined with a Shimadzu 160UV recording Spectrophotometer. Graphs (a) and (b) show absorption on the vertical axis and wavelength of absorption on the horizontal axis. Graphs (a) and (b) represent the same absorption spectra: (a) shows absorption for the range of 0 to 0.10, while (b) shows absorption for the range 0 to 0.3. A peak is present at 581 nm (See graph (a)) with a molar absorbance of $3.26 \times 10^{-1}$. There is also an inflection at 276 nm (See graph (b)).
Figure 9B:
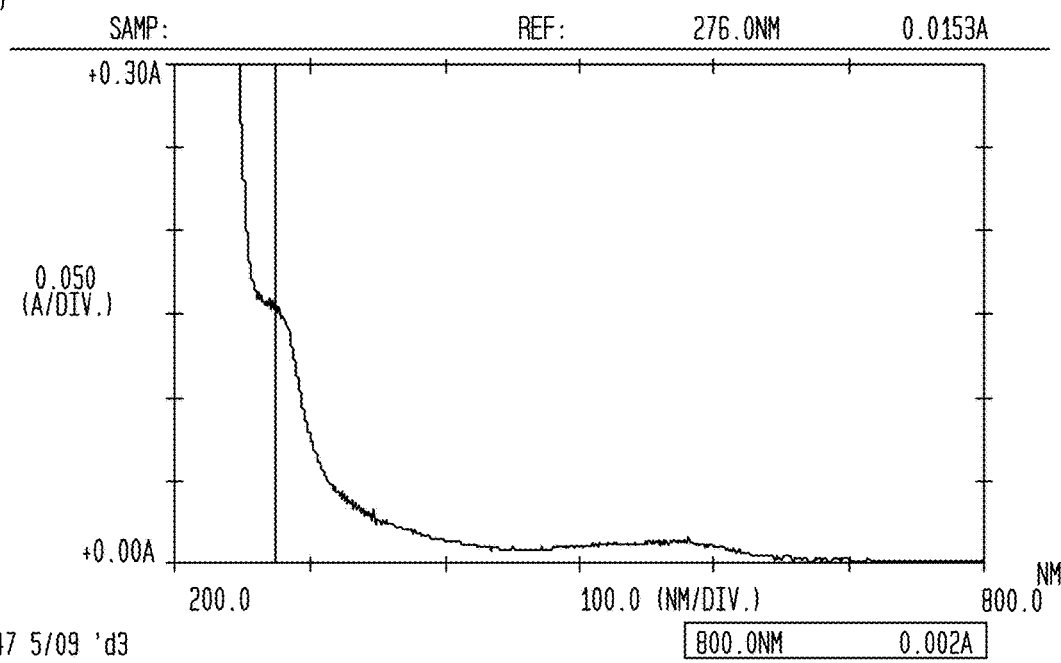

Toroglobulin™ was further characterized by UV-Visible spectroscopy using a Shimadzu 160UV recording spectrophotometer. As seen in FIG. 9, an absorption peak of 0.015 is present at approximately 581 nm and an absorption inflection of 0.153 is present at approximately 276 nm. The top and bottom graphs in FIG. 9 depict the same absorption spectrum; the top graph absorption scale is set to 0.1 while the bottom graph absorption scale is set to 0.3.

FTIR Spectroscopy

FTIR spectroscopy was used to further characterize Toroglobulin™, and to characterize several of the precursors used in the synthesis of Toroglobulin™. FTIR studies were performed using a Shimadzu FTIR Model 8400S Spectrophotometer. The FTIR spectra of Toroglobulin™ and its major components are seen in FIGS. 11 through 18. The absorption at specific wavenumbers (1/cm) represents the signature of components and the unique identity of the ruthenium to sphingomyelin bond, which appears at the Myelux™ stage of synthesis. All FTIR samples were prepared as dry pellets in KBr.

Figure 13:
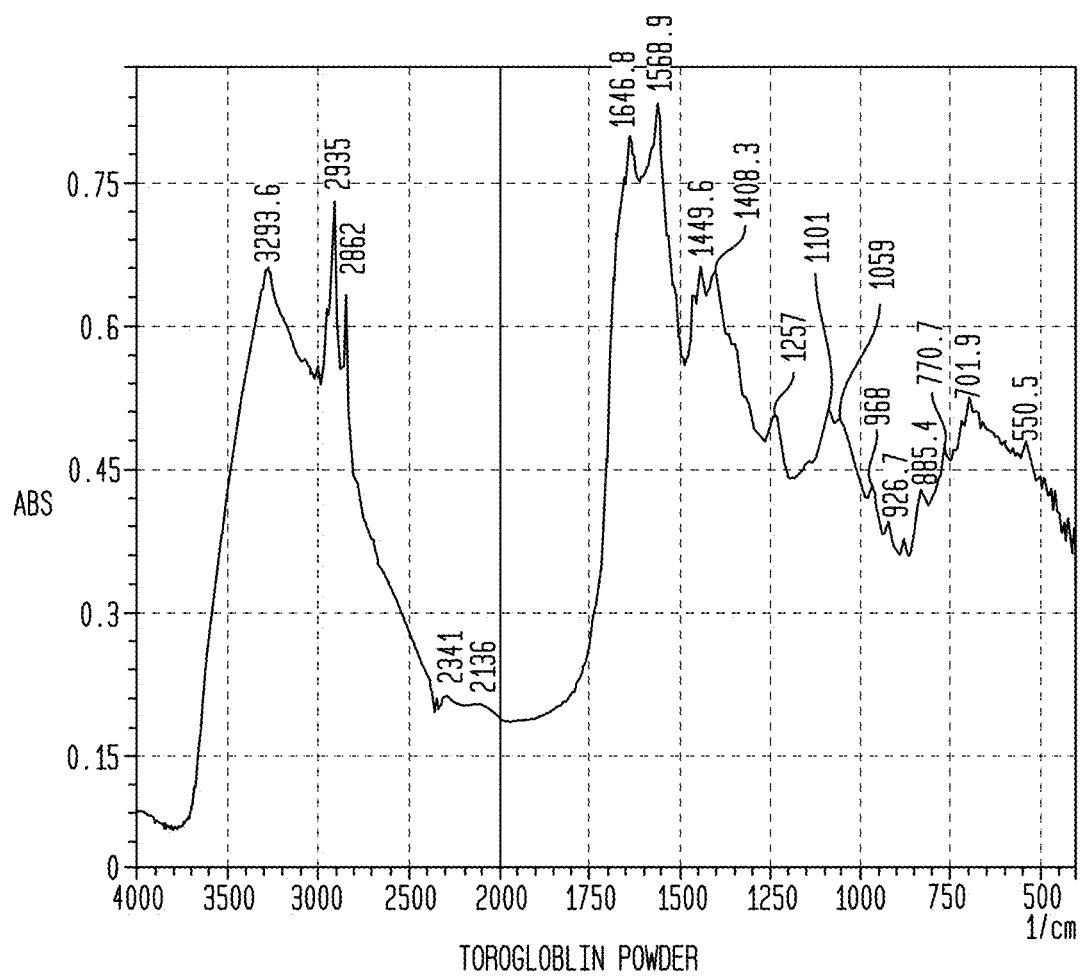
FIG. 13 depicts an FTIR Spectrum of Lyophilized Toroglobulin™ complex. Identifying peaks (cm$^{-1}$) are as follows: 550.5, 701.9, 770.7, 830.4, 885.4, 926.7, 968, 1059, 1101, 1257, 1408.3, 1449.6, 1568.9, 1646.8, 2341, 2862, 2935, 3293.6.
Figure 14:
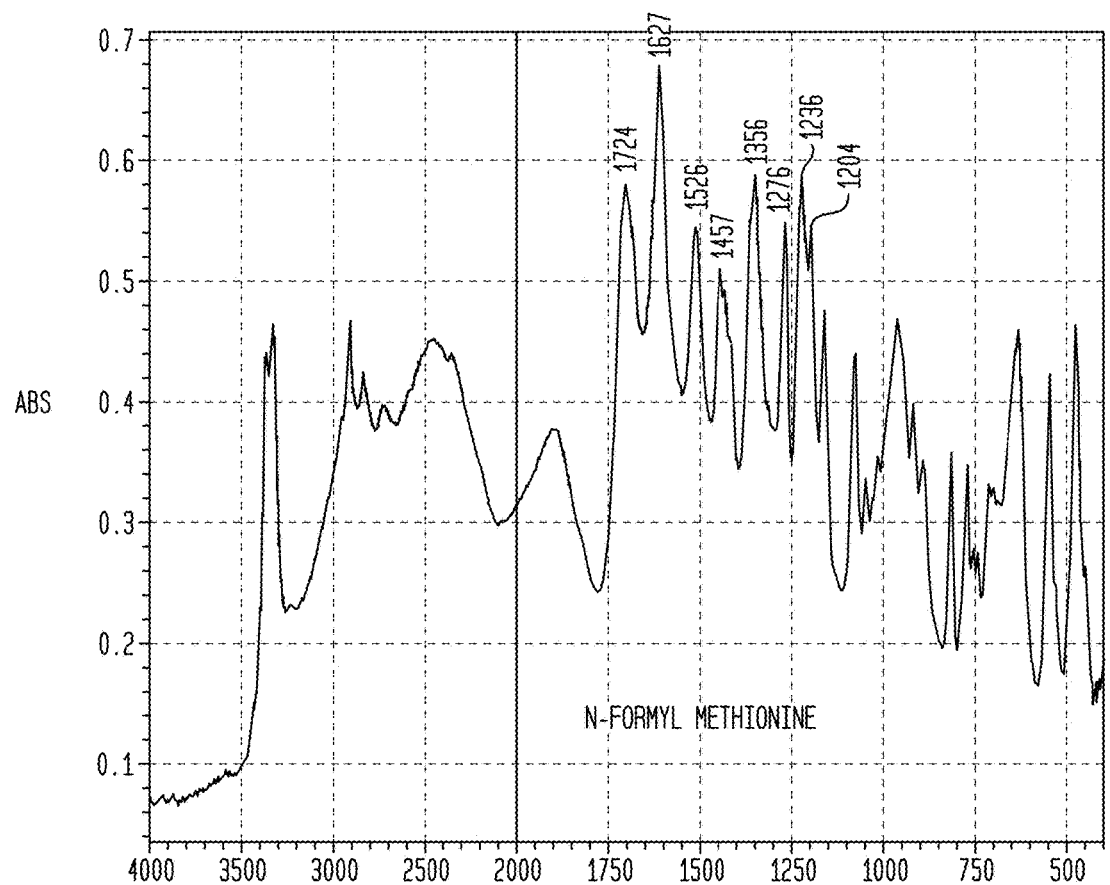
FIG. 14 depicts an FTIR Spectrum of N-Formyl Methionine itself. Numerous identifying peaks (cm$^{-1}$) are labeled.

As seen in FIG. 13, the identifying FTIR peaks of lyophilized Toroglobulin™ are as follows: 550.5, 701.9, 770.7, 830.4, 885.4, 926.7, 968, 1059, 1101, 1257, 1408.3, 1449.6, 1568.9, 1646.8, 2341, 2862, 2935, and 3293.6.

Another absorption peak, seen in FIG. 12, is representative of the bond between ruthenium and the sphingomyelin carbonyls. That ruthenium/sphingomyelin bond creates an absorption peak at 1596 1/cm, which can be seen at the Myelux™ stage (FIG. 12), but is obscured during subsequent steps of the synthesis of Toroglobulin™ as it is hidden by overlaps in spectral absorbance. This absorption peak is consistent with previous studies of organo-ruthenium bonds, and indicates that the ruthenium is bonded to a carbonyl as a CO or COOH carboxyl form. The absorption peak is not present in FTIR spectra of the reactants used in the synthesis—sphingomyelin, ruthenium N-formyl methionine, and arginine linoleic acid.

Figure 15:
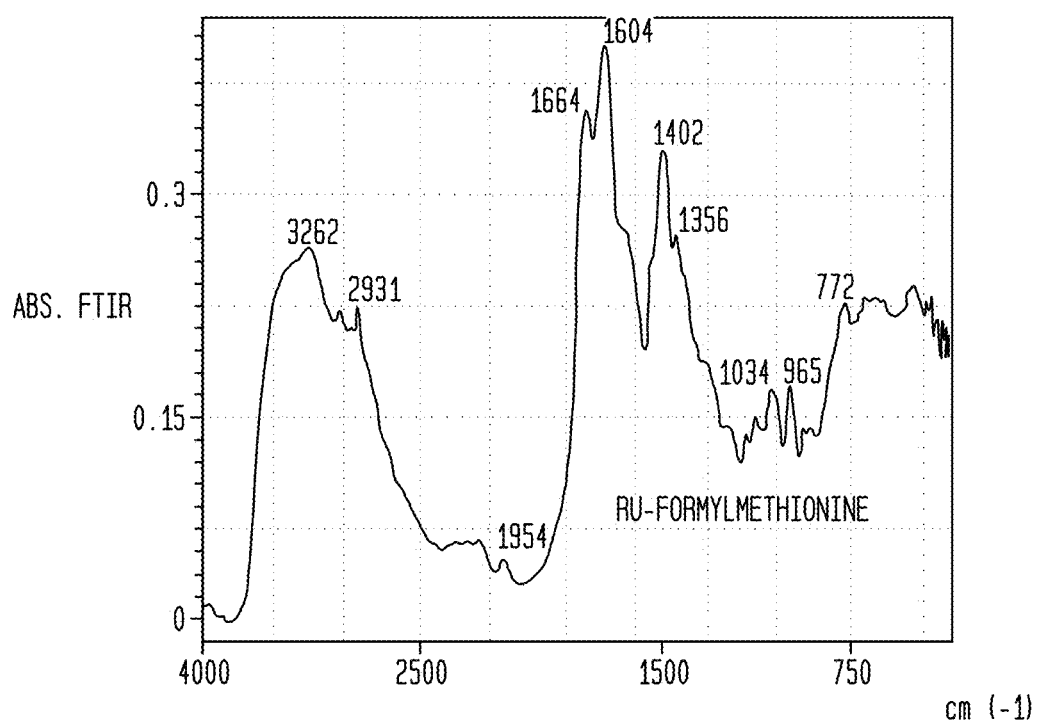
FIG. 15 depicts an FTIR Spectrum of a Ruthenium Formyl Methionine complex. New peaks (cm$^{-1}$), formed as a result of reacting with Ruthenium, are seen at: 1664 cm$^{-1}$, 1604 cm$^{-1}$, 1402 cm$^{-1}$.
Figure 16:
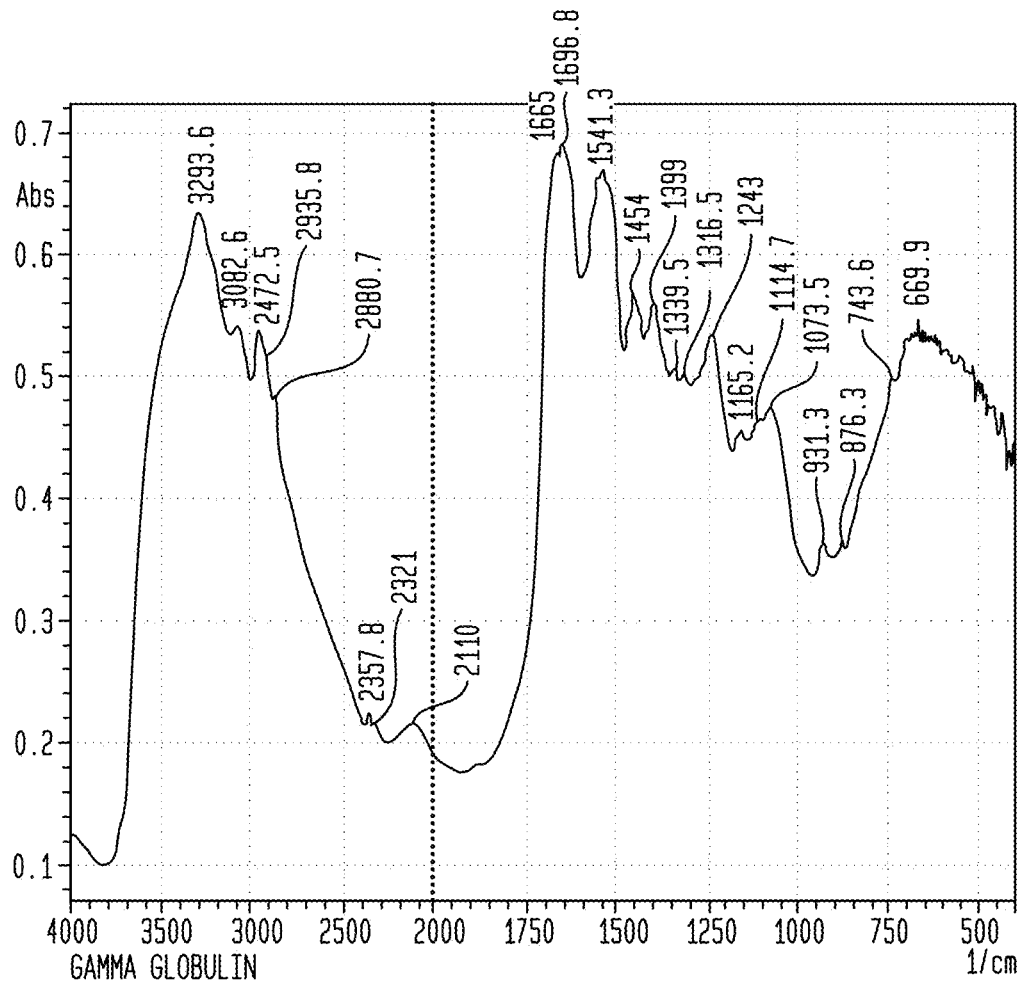
FIG. 16 depicts an FTIR Spectrum of Gamma Globulin (Sigma, Cat. No. G4386, Human, from Cohn Fraction II, III) (cm$^{-1}$).
Figure 17:
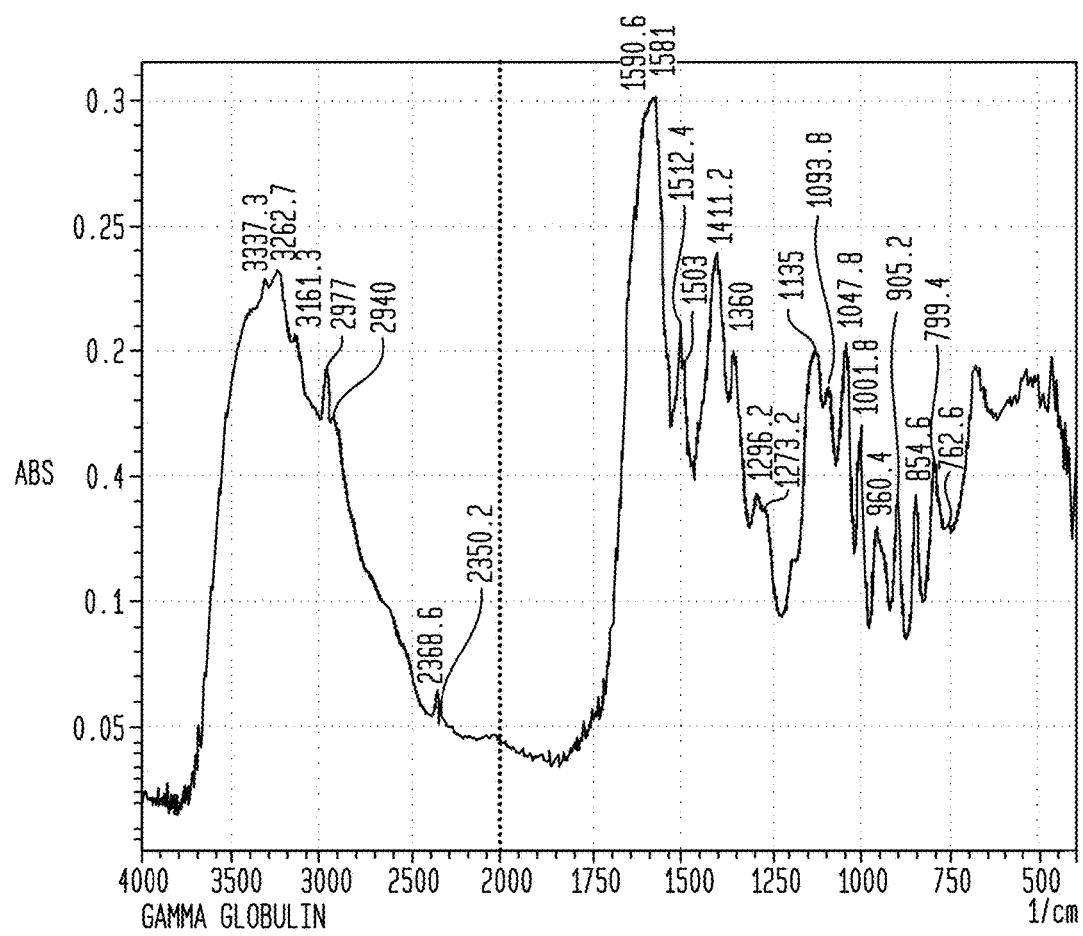
FIG. 17 depicts an FTIR Spectrum of the bis (threonine) Zn complex (cm$^{-1}$) ("bis (threonine) Zn" refers to two threonines bound to a zinc).
Figure 18:
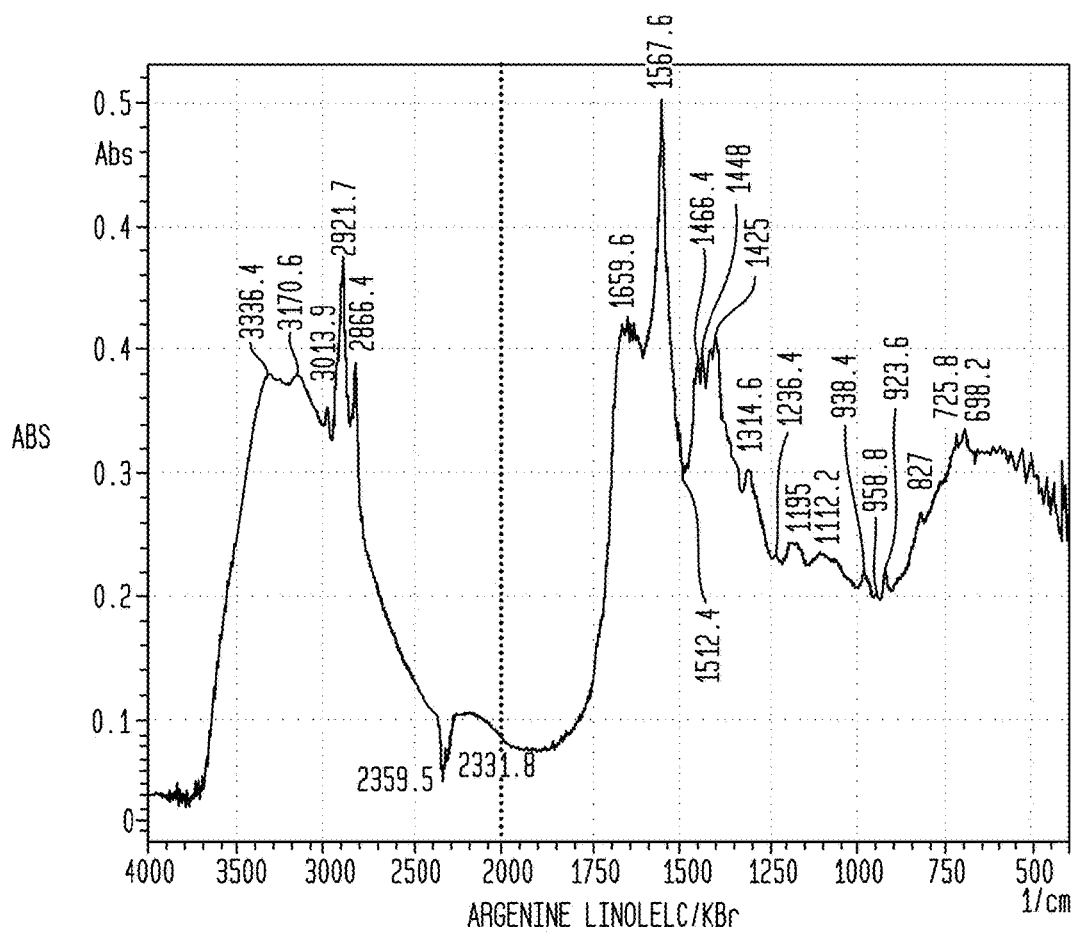
FIG. 18 depicts an FTIR Spectrum of an arginine linoleic acid mixture (cm$^{-1}$).

An absorption spectrum of ruthenium formyl methionine is also shown in FIG. 15; absorption peaks due to the reaction with ruthenium are present at 1664, 1604, and 1402 1/cm. The FTIR spectra for each of the constituents—sphingomyelin (FIG. 11), formyl methionine (FIG. 14), gamma globulin (FIG. 16), bis-threonine Zn (FIG. 17), and arginine linoleic acid (FIG. 18)—are also shown.

We noted that carbonyls (CO) groups, are a set of variants that include RCHO, RCOR', CH$_2$O, RCOOH, RCOOR', RCONR'R', RC(O)C(R')CR"R'". RCOX, and (RCO)$_2$O. Sphingomyelin has two carbonyls in the vicinity of phosphate:

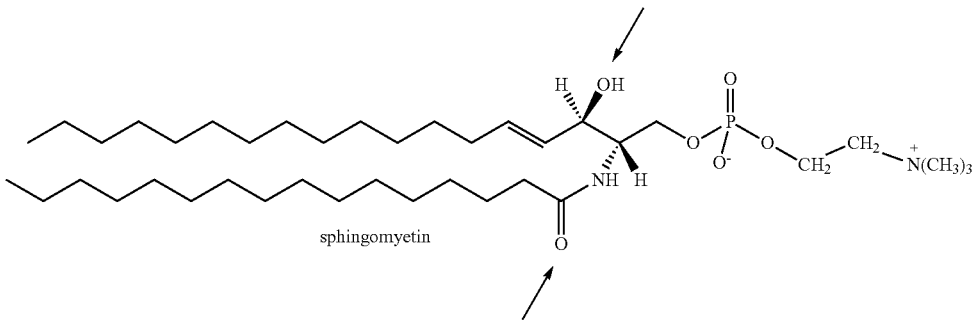

sphingomyetin

Organo-metallic structures, such as [Fac-Ru(O$_2$CMe)$_3$(CO$_3$]—has IR bands due to unidentate acetate ligands, with $v_{as}$ CO$_2$ at 1612 and 1596 cm-1, vs CO$_2$ 1363 and 1314 cm-1. RuH(CO)OCOR)(PPh$_3$)$_2$ and Ru(CO)(OCOR)PPh$_3$)$_2$ (CH$_3$CHCN), where R=Me, Et, nPr or Ph, all give characteristic bands of chelating carboxylates. [Davidson, G., Spectroscopic Properties of Inorganic and Organometallic Compounds, Royal Soc. Chem., V. 24, P. 342, Billing & Sons Ltd. Worcester, Copyright 1991].

The metal interaction with the phosphate does not directly show an infrared frequency. However a study by Lindblad and Rebenstorf indicated that organo-metallic complex bonding to carbonyls and carboxylates for Mn, Fe, Co, and Ni, is facilitated by a surface composed of AlPO$_4$, through the action of the phosphate. [Lindblad, T, Rebenstorf, B, Amorphous AlPO$_4$ as Catalyst Support. 5. FTIR Study of CO Absorbed on Transition Metal Ions Supported on Amorphous AlPO4 and SiO2, Acta Chemica Scandinavia, v. 45, p. 342-348, 1991.] This suggests that sphingomyelin phosphate group may provide a preliminary activation of metals for carbonyl bonding reactions.

The sub-complex composed of ruthenium formyl methionine and sphingomyelin was shown by FTIR studies to have a new band at 1596 cm$^{-1}$, the same as reported by Davidson for an organo-ruthenium. [Davidson, G., Spectroscopic Properties of Inorganic and Organometallic Compounds, Royal Soc. Chem., V. 24, P. 342, Billing & Sons Ltd. Worcester, Copyright 1991.] This band is ruthenium bonded to a carbonyl as CO or COOH carboxyl form. The band is not present in the reactants used in the synthesis—sphingomyelin, ruthenium N-formyl methionine, and arginine linoleic acid.

Chromatography

Figure 10:
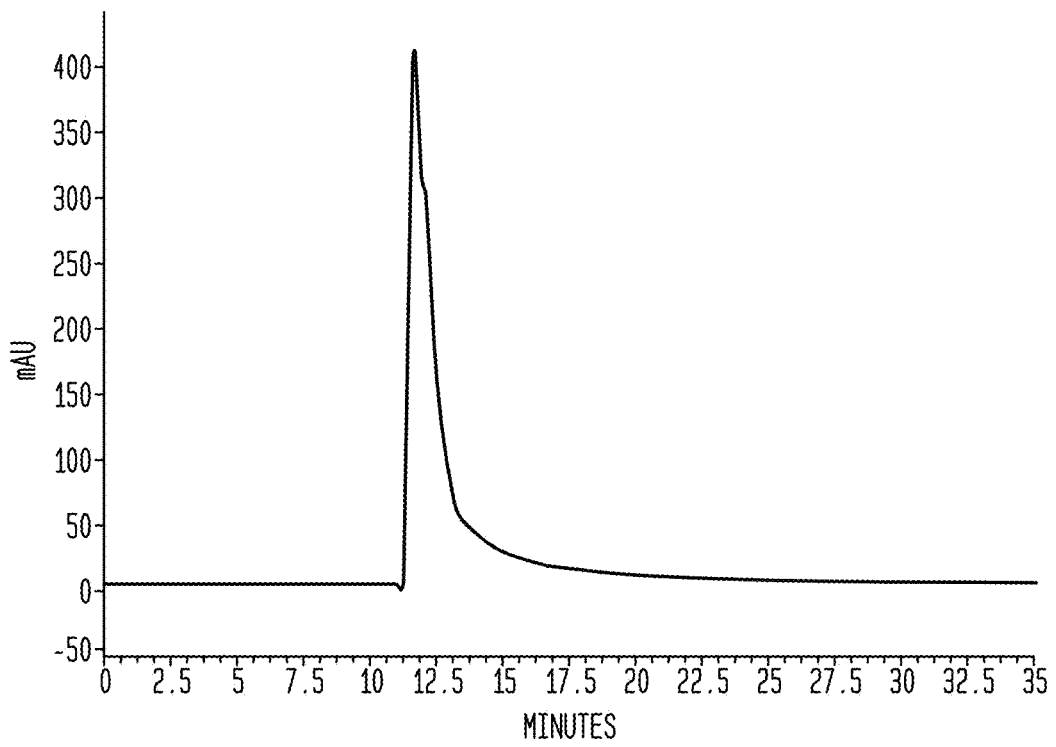
FIG. 10 depicts the results of HPLC-chromatography showing the monomolecular character of Toroglobulin™. HPLC—Chromatography was performed with a Beckman Gold system with an 18 C column stationary phase and isopropanol mobile phase. A scan is shown with absorption (mAU) on the vertical axis and time (Minutes) on the horizontal axis. The retention peak is consistent with a single conjugate molecular complex with a small amount of excess ligand.
Figure 11:
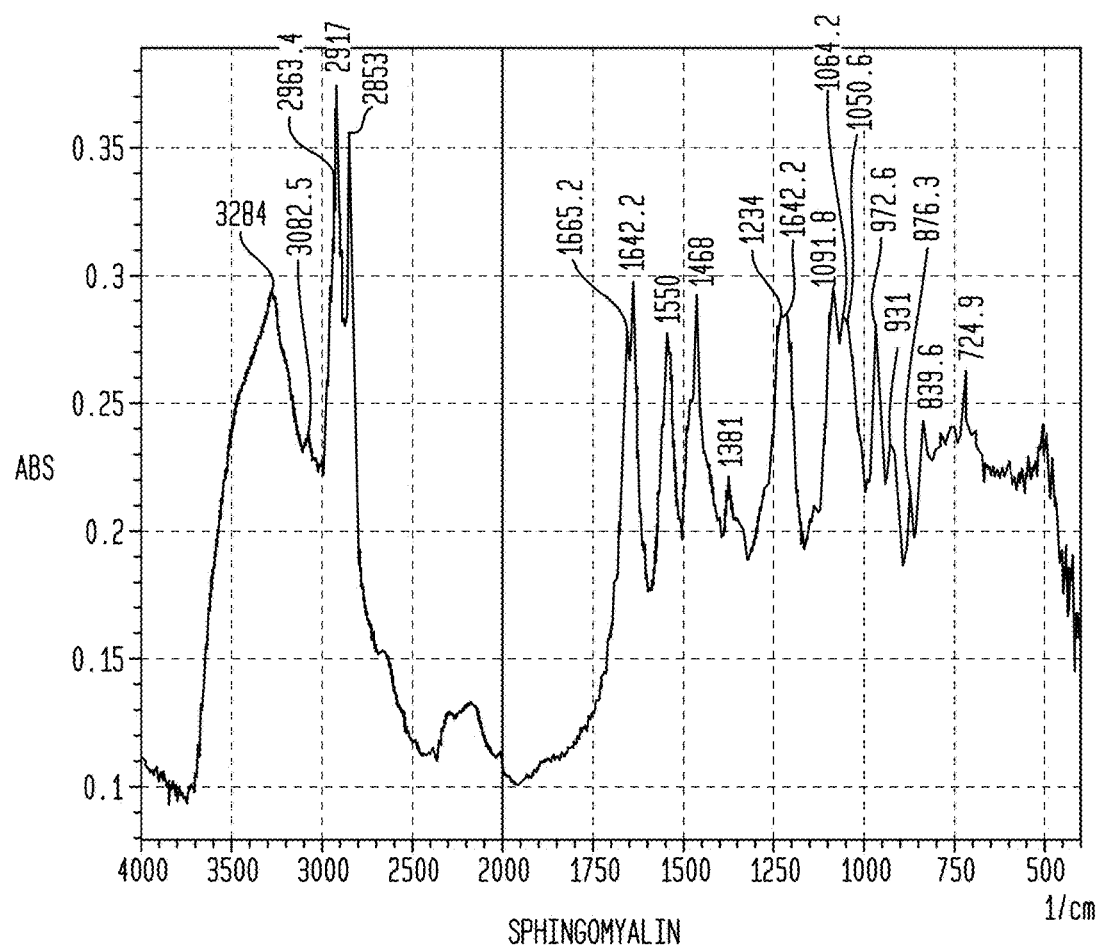
FIG. 11 depicts an FTIR Spectrum of sphingomyelin itself with numerous peaks labeled ($cm^{-1}$).

The Toroglobulin™ complex was also characterized by high performance liquid chromatography (HPLC) using a Beckman Gold system with an 18 C stationary phase column and using isopropanol as the mobile phase. FIG. 10 shows an absorption scan of the resulting effluent after having been run through the stationary phase. The absorption is indicated as mAU. Time until effluent reached the detector is indicated in minutes.

A single absorption peak was detected at approximately 12.5 minutes of retention time. The single retention peak is consistent with a single conjugate molecular complex having a small amount of excess ligand used to drive the synthesis. Thus, the combination of sphingomyelin with linoleic acid, arginine, formyl methionine, threonine, and gamma globulin can be constituted as a single, large molecular complex.

Example 3—In Vitro Analysis of Toroglobulin

Toroglobulin™ was also tested for cytotoxic effects on cancer cell lines. Two different cancer cell lines were used: MCF-7, human breast cancer cell line (ATCC Cat. No. HTB-22) and PANC-1, human pancreatic cancer cell line (ATCC Cat. No. CRL-1469). Each cell line has been studied extensively and is available through the ATCC.

Methodology of the In Vitro Cancer Screens

It is common to study the in vitro toxic effect of agents by quantifying viability of cells by measuring total biomass. One well established method to measure total biomass is by staining total cellular proteins using the compound Sulforhodamine B. Sulforhodamine B is a dye that gets incorporated into cells upon staining. Differences in the number of cells present in the stain (the biomass) effect the intensity of color imparted onto the cell culture, which can be measured by various type of spectrophotometers. Changes in the color intensity of treated vs control cells indicate the level of cytotoxicity of the agent. [See In Vitro Toxicology Assay Kit Sulforhodamine B based, Sigma-Aldrich, Catalog Number TOX6, available at https://www.sigmaaldrich.com/content/dam/sigma-aldrich/docs/Sigma/Bulletin/tox6bul.pdf]

For a typical experiment, cells were inoculated into 96 well microtiter plates in 100 μL at plating densities ranging from 5,000 to 40,000 cells/well depending on the doubling time of individual cell lines. After cell inoculation, the microtiter plates were incubated at 37° C., 5% CO2, 95% air and 100% relative humidity for 24 h prior to addition of test agent. Aliquots of 100 μl of the different test agent dilutions were added to the appropriate microtiter wells already containing 100 μl of medium, resulting in the required final test agent concentrations.

Following test agent addition, the plates were incubated for an additional 48 h at 37° C., 5% CO2, 95% air, and 100% relative humidity. For adherent cells, the assay was terminated by the addition of cold TCA. Cells were fixed in situ by the gentle addition of 50 μl of cold 50% (w/v) TCA (final concentration, 10% TCA) and incubated for 60 minutes at 4° C. The supernatant was discarded, and the plates were washed five times with tap water and air dried. Sulforhodamine B (SRB) solution (100 μl) at 0.4% (w/v) in 1% acetic acid was added to each well, and plates were incubated for 10 minutes at room temperature. After staining, unbound dye is removed by washing five times.

After staining, unbound dye was removed by washing five times with 1% acetic acid and the plates are air dried. Bound stain was subsequently solubilized with 10 mM trizma base, and the absorbance was read on an automated plate reader at a wavelength of 515 nm. For suspension cells, the methodology is the same except that the assay was terminated by fixing settled cells at the bottom of the wells by gently adding 50 μl of 80% TCA (final concentration, 16% TCA).

Using the seven absorbance measurements [time zero, (Tz), control growth, (C), and test growth in the presence of test agent at the five concentration levels (Ti)], the percentage growth is calculated at each of the test agent concentrations levels. Percentage growth inhibition is calculated as:

$[(Ti-Tz)/(C-Tz)] \times 100$ for concentrations for which $Ti >/= Tz$ $[(Ti-Tz)/Tz] \times 100$ for concentrations for which $Ti < Tz$.

Three dose response parameters were calculated for each experimental agent. Growth inhibition of 50% (GI50) was calculated from $[(Ti-Tz)/(C-Tz)] \times 100 = 50$, which is the test agent concentration resulting in a 50% reduction in the net protein increase (as measured by SRB staining) in control cells during the test agent incubation. The test agent concentration resulting in total growth inhibition (TGI) is calculated from Ti=Tz. The LC50 (concentration of test agent resulting in a 50% reduction in the measured protein at the end of the test agent treatment as compared to that at the beginning) indicating a net loss of cells following treatment was calculated from $[(Ti-Tz)/Tz] \times 100 = -50$. Values were calculated for each of these three parameters if the level of activity was reached; however, if the effect was not reached or was exceeded, the value for that parameter was expressed as greater or less than the maximum or minimum concentration tested.

Results of In Vitro Testing

The results of the in vitro tests of Toroglobulin™'s effect on the breast cancer cell line, MCF-7, and the pancreatic cancer cell line, PANC-1, showed strong cytotoxicity. See FIGS. 19 and 20. This effect was greater than that of the putative anti-cancer agent, poly-MVA.

Figure 19:
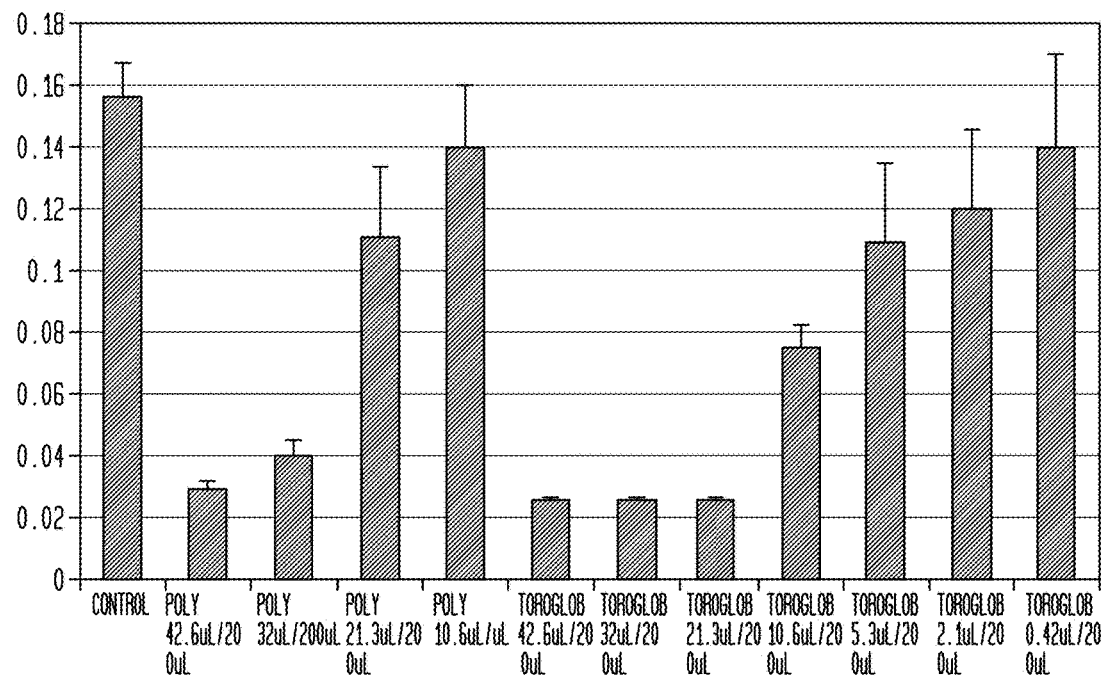
FIG. 19 depicts the results of an in vitro analysis of Toroglobulin™'s effect on breast cancer cell line MCF-7 (ATCC, Cat. No. HTB-22), showing effective cytotoxicity. Cytotoxicity was quantified by measuring light absorption (492 nm) of stained MCF-7 cells after culturing with the compounds as indicated. Experiments were repeated in triplicate. The cytotoxic effect of Toroglobulin™ was more potent than Lipoic Acid Mineral Complex (PolyMVA), a composition having anti-cancer properties comprising palladium bonded to alpha-lipoic acid, Vitamins B1, B2 and B12, formyl-methionine, N-acetyl cysteine, and trace amounts of molybdenum, rhodium, and ruthenium. The indicated volumes of Toroglobulin™ were from a 25 mg/mL stock solution, while indicated volumes of PolyMVA were from a 22 mg/mL stock solution.

As seen in FIG. 19, MCF-7 cells were cultured and treated with agents as described above. Different groups of cells were treated with progressively lower concentrations of either poly-MVA or Toroglobulin™. Four different groups of cells were treated in triplicate from a stock solution of 22.0 mg/mL poly-MVA in a total volume of 200 μl liquid media: 42.6 ul; 32 ul; 21.3 ul; and 10.6 ul. Similarly, seven different groups of MCF-7 cells were treated in triplicate with the following volumes of 25.0 mg/mL Toroglobulin™ in a total volume of 200 μl liquid media: 42.6 ul; 32 ul; 21.3 ul; 10.6 ul; 5.3 ul; 2.1 ul; and 0.42 ul. A triplicate control group of cells were left untreated. Cytotoxic effect was quantified as described above.

The results seen in FIG. 19 show that Toroglobulin™ has a cytotoxic effect on MCF-7 cells compared to untreated controls. Toroglobulin™ also has a significantly stronger cytotoxic effect than poly-MVA. The three highest concentration treatments with Toroglobulin™ resulted in an approximately 7.5 fold decrease in cell density of MCF-7 cells when compared to untreated control cells. Toroglobulin™ treatment also resulted in significantly less cell density when compared to similarly situated poly-MVA treated cells. For example, MCF-7 cells treated with 21.3 μl of Toroglobulin™ showed about a 5 fold decrease in cell density when compared to cells treated with 21.3 μl of poly-MVA. It was also possible to achieve the same level of cytotoxicity of poly-MVA using substantially less Toroglobulin™. By way of another example, treatment of MCF-7 cells with 5.3 μl of Toroglobulin™ show the same cell density as MCF-7 cells treated with 21.3 μl of poly-MVA. Thus, at these concentrations, poly-MVA is about 4 times more potent than poly-MVA.

Figure 20:
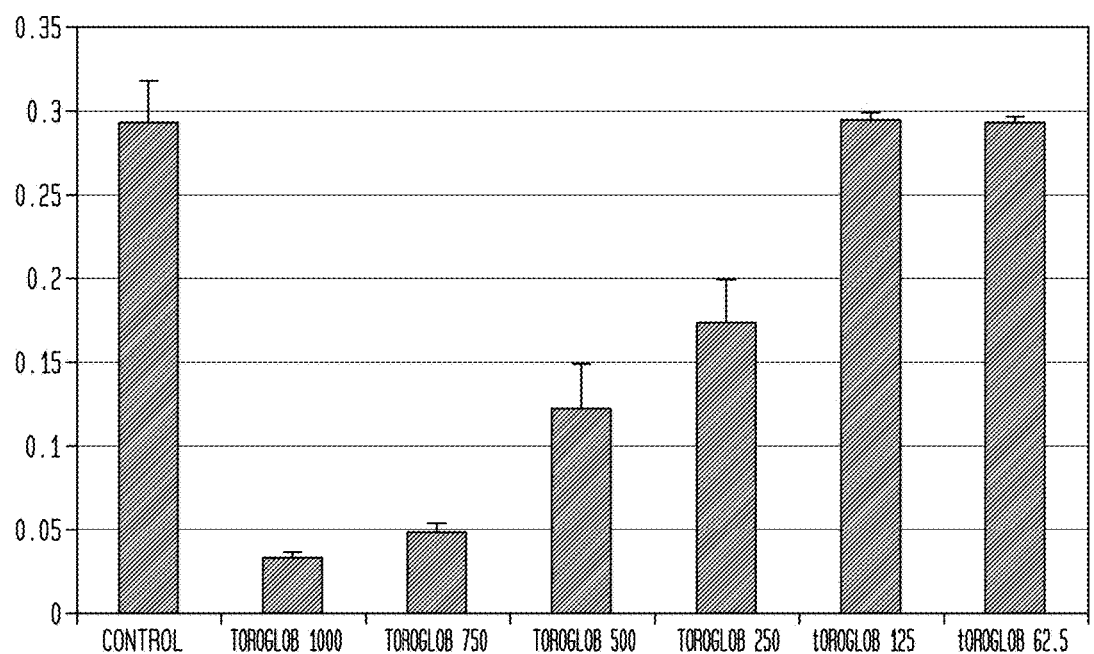
FIG. 20 depicts the results of an in vitro analysis of Toroglobulin™'s effect on pancreatic cancer cell line PAN-C (ATCC Cat. No. CRL-1469), showing effective cytotoxicity. Cytotoxicity was quantified by measuring light absorption (492 nm) of stained PAN-C cells after culturing with the compounds, as indicated. The indicated volumes of Toroglobulin™ were from a 25 mg/mL stock solution.

As seen in FIG. 20, PANC-1 cells were cultured and treated with Toroglobulin™, as described above. Six different groups of PANC-1 cells were treated in triplicate with the following volumes of 25.0 mg/mL Toroglobulin™ in 2000 µl liquid media: 1000 µl; 750 µl; 500 µl; 250 µl; 125 µl; and 62.5 µl. A triplicate control group of cells were left untreated. Cytotoxic effect was quantified as described above.

The results seen in FIG. 20 show that Toroglobulin™ has a cytotoxic effect on PANC-1 cells compared to untreated controls. While the two lowest concentration treatments (125 and 62.5 ul) did not have a statistically significant effect compared to controls, each of the higher concentration treatment (100, 750, 500, and 250 ul) each had a dramatic effect. For example, the 250 µl Toroglobulin™ treatment of PANC-1 cells resulted in a 50% decrease in cell density, compared to controls, after the 48 hour incubation period. Even more dramatically, the 1000 µl Toroglobulin™ treatment of PANC-1 cells resulted in about an 11-fold reduction in cell density over the 48 hour incubation period. These results indicate that Toroglobulin™ has a potent cytotoxic effect on the PANC-1 cancer cell line.

Example 4—In Vivo Analysis of Toroglobulin

Method—In Vivo Testing

Methods for mouse studies were approved by a committee on animal use.

A Swiss albino mouse model is commonly used with Erlich Ascites Carcinoma cell lines to test the effect a compound may have on tumor cell growth, tumor weight, and survival time after tumor cell transplant. [See, e.g., Khairul Islam, et al., In vivo Anticancer Activities of Benzophenone Semicarbazone against Ehrlich Ascites Carcinoma Cells in Swiss Albino Mice, Cancer Biol Med. 2012 December; 9(4): 242-247.] Erlich Ascites Carcinoma cells are of a mouse epithelium origin, and have been found to grow equally well in both male and female mice, without spontaneous regression, after injection of a minimum of 400,000 tumor cells. [F. Hartveit, The Survival Time of Mice with Ehrlich's Ascites Carcinoma related to the Sex and Weight of the Mouse, and the Blood Content of the Tumour, Br. J. Cancer. 1961 June; 15(2): 336-341.] Erlich Ascites Carcinoma cells can be subcultured as adherent monolayers of cells using standard tissue culture procedures. [Boone C et al., Characterization of an in vitro strain of Ehrlich-Lettre ascites carcinoma subjected to many periodic mouse passages, J. Natl. Cancer Inst. 34: 725, 1965.] The tissue cultured cells may be injected into mice, wherein ascites may form that are rich in free neoplastic cells. The ascetic fluid may be drawn by syringe and the neoplastic cells subsequently injected in further mice for experimentation. [Bailiff, The solid phase of the Ehrlich Ascites tumor in mice, Cancer Research, 1954].

The effect of Toroglobulin™ on Ehrlich ascites carcinoma obtained from the National Institutes of Health in this model was determined. Ehrlich ascites carcinoma was established in a female Swiss mouse model. The ascitic serum was allowed to grow out to an amount that was easily withdrawn by syringe. The cells were examined microscopically to confirm viability and concentration.

The serum was diluted 10× in Dulbecco's culture medium and $2 \times 10^5$ cells were injected into the peritoneum of each of 24 test mice. After 24 hours, a group of 12 of these mice was injected i.p. with 0.2 ml of 25.0 mg/mL Toroglobulin™, on a daily basis except for weekend lapses. The total Toroglobulin™ injected in each mouse was 66.7 mg/kg body mass. A 50 day study was performed. Injections were performed on 14 of the days for a total of 14 injections per mouse, allowing weekend lapses on the 5th and 6th and 12th and 13th days. The remaining 12 mice served as untreated controls.

Results—In Vivo Testing

Figure 21:
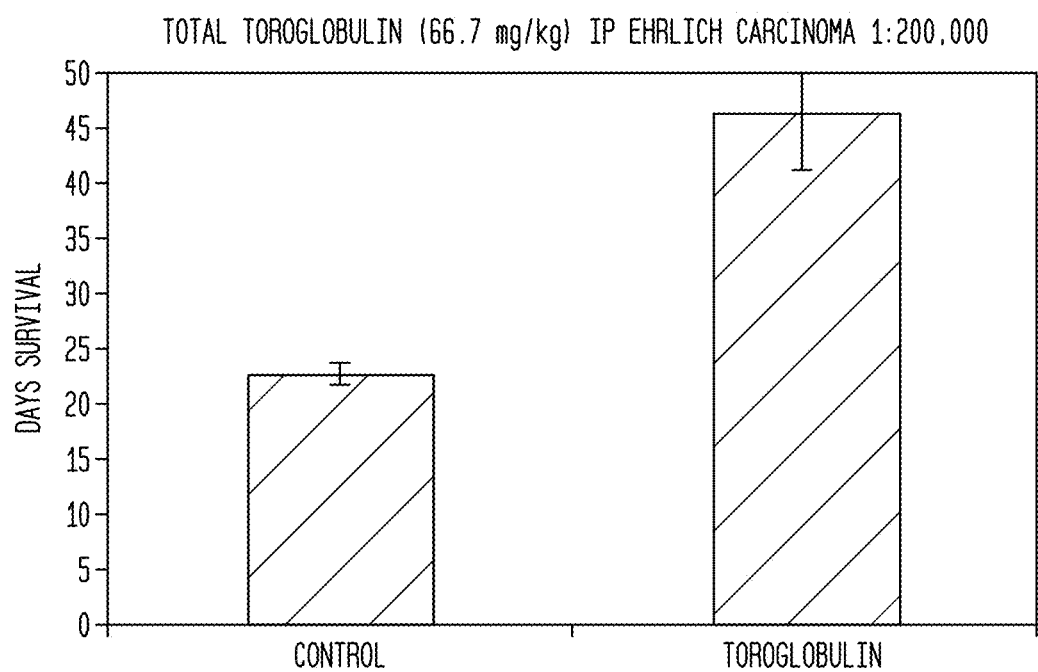
FIG. 21 depicts the results of an in vivo Swiss mouse model of Erlich Ascites carcinoma treated with either a negative control, phosphate buffered saline ("PBS"), or 66.7 mg/kg of Toroglobulin™. The Toroglobulin™ and control compound were administered via intra peritoneal injections, performed approximately every 3.5 days over the 50 day study, totaling 14 injections per mouse. The results show Toroglobulin™'s effect on inhibition of tumor growth, or tumor initiation, resulting in a marked increase in survival.
Figure 22:
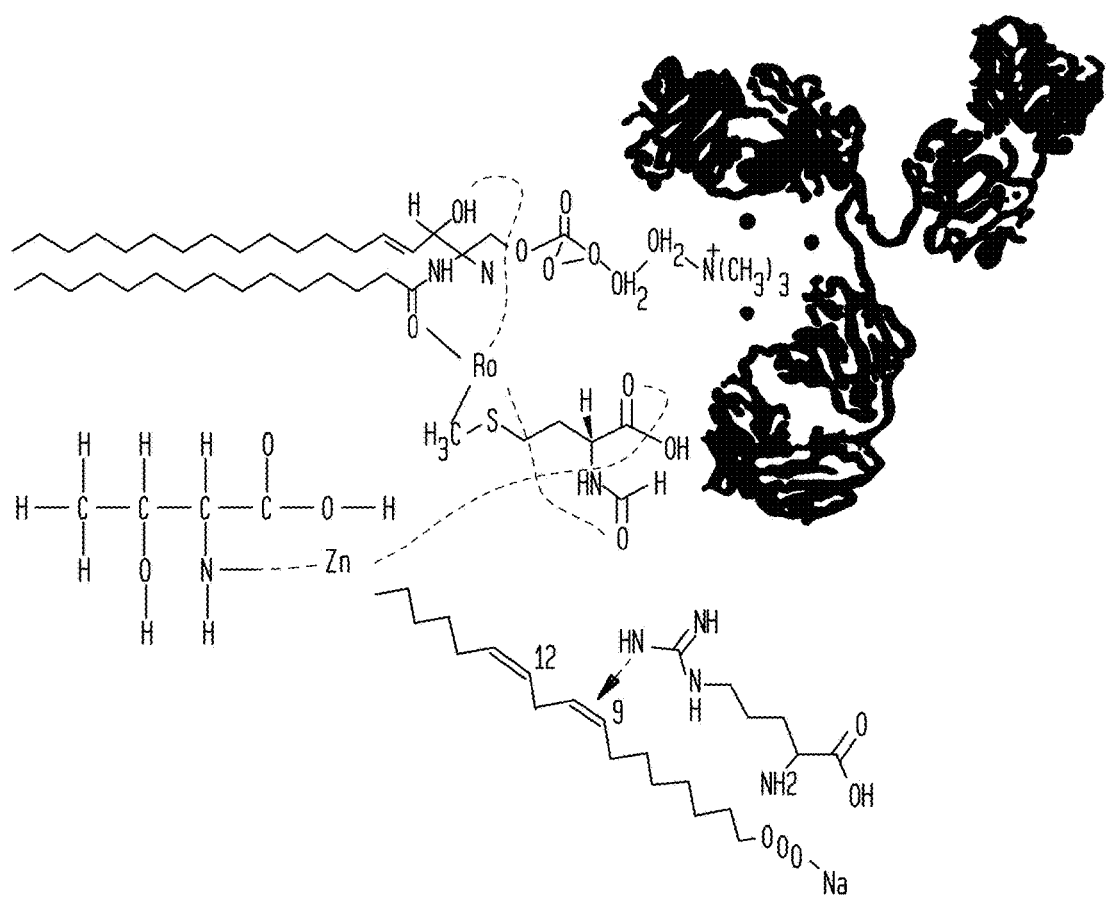
FIG. 22 depicts a proposed structure of Toroglobulin™.

The results of this experiment are seen in FIG. 21. The control mice survived an average of 22.5 days, with 0 mice surviving until the end of the 50 day observation period. The mice that were treated with Toroglobulin™, as described above, survived an average of 45.67 days, with 7 mice surviving until the end of the 50 day observation period. The standard error measure for control and Toroglobulin™ treated groups was 1.05 days and 5.13 days respectively. Mice treated with Toroglobulin™ had a 58.33% survival rate at the end of the 50 day observation period, which equates to a 102.96% increase compared with controls. In total, the data indicates that Toroglobulin™ significantly increases survival time in an ascites stage 4 cancer model.

Without being limited by theory, one possible mechanism for therapeutic effect relates to a cancer therapy by catalyzing electron energy transfer to histone and DNA. The intent is to use an energy pathway to condense the expanded chromatin of tumor cells to become compact, as in the heterochromatic state of normal cell nuclei.

While the present invention has been described with reference to the specific embodiments thereof it should be understood by those skilled in the art that various changes may be made and equivalents may be substituted without departing from the true spirit and scope of the invention. In addition, many modifications may be made to adopt a particular situation, material, composition of matter, process, process step or steps, to the objective spirit and scope of the present invention. All such modifications are intended to be within the scope of the claims appended hereto.

What is claimed is:

1. An organometallic complex comprising:
    a first lipid component comprising a carbonyl functional group, an alcohol functional group, or a combination thereof;
    a ruthenium component;
    a first amino acid component comprising a carbonyl functional group, a methyl functional group, or combination thereof;
        wherein the ruthenium component is associated with the first lipid component via the carbonyl functional group, alcohol functional group, or combination thereof, of the first lipid component;
        wherein the ruthenium component is associated with the first amino acid component via the carbonyl functional group, methyl functional group, or combination thereof, of the first amino acid;
        wherein the first lipid component, the ruthenium component and first amino acid component are in association to form a first sub complex;
    the organometallic complex further comprising a macromolecule component;
    the organometallic complex further comprising:
        a second lipid component comprising a methyl functional group, an alkene functional group, a carboxylic acid functional group, or a combination thereof;
        a metal component;
        a second amino acid component comprising a carboxylic acid functional group, an amine functional group, or a combination thereof; and
        a third amino acid component comprising an amine functional group;
            wherein the metal component is associated with the second lipid component via the methyl functional group, the alkene functional group, the carboxylic acid functional group, or combination thereof, of the second lipid component;
            wherein the metal component is associated with the second amino acid component via the amine functional group, carboxylic acid functional group, or combination thereof, of the second amino acid;

wherein the third amino acid component is associated with the second lipid component via an association of the alkene functional group, the methyl functional group, the carboxylic acid function group, or combination thereof, of the second lipid with the amine functional group of the third amino acid;

wherein, the second lipid component, metal component, second amino acid component, and third amino acid component are in association to form a second sub complex;

wherein the first sub complex associates with the second sub complex via the metal component and the carbonyl functional group or the methyl functional group of the first amino acid to form a single larger complex;

wherein the macromolecule component associates at least with the first sub complex;

wherein the complex does not comprise palladium.

2. The organometallic complex of claim 1, wherein the ruthenium component comprises elemental ruthenium, a ruthenium salt, or a combination thereof.

3. The organometallic complex of claim 1, wherein the first lipid component is a fatty acid component or a derivative thereof, a membrane lipid component or a derivative thereof, or a combination thereof.

4. The organometallic complex of claim 1, wherein the first lipid component is an amphipathic molecule having a hydrophilic region and a hydrophobic region, the hydrophobic region comprising one or more hydrocarbon tails between 2 and 24 carbons long and the hydrophilic region comprising a net charge of between 0 and 4 at a pH of 7.

5. The organometallic complex of claim 4, wherein the first lipid component is a sphingolipid.

6. The organometallic complex of claim 5, wherein the sphingolipid is a sphingomyelin.

7. The organometallic complex of claim 1, wherein the first amino acid component comprises an amino acid or a derivative thereof.

8. The organometallic complex of claim 1, wherein the first amino acid component comprises an N-formyl amino acid.

9. The organometallic complex of claim 1, wherein the first amino acid component comprises N-formyl methionine.

10. The organometallic complex of claim 1, wherein the macromolecule component comprises a polypeptide chain having a molecular weight of at least 20 kilodaltons (kDa).

11. The organometallic complex of claim 10, wherein the polypeptide comprises an immunoglobulin or derivative thereof.

12. The organometallic complex of claim 1, wherein the second lipid comprises a fatty acid component or a derivative thereof.

13. The organometallic complex of claim 12, wherein the fatty acid component comprises a hydrocarbon tail of between 2 and 24 carbons.

14. The organometallic complex of claim 13, wherein the fatty acid component comprises between 0 and 3 double bonds.

15. The organometallic complex of claim 14, wherein the fatty acid component comprises linoleic acid.

16. The organometallic complex of claim 1, wherein the metal component comprises a non-transition metal component.

17. The organometallic complex of claim 16, wherein the non-transition metal component comprises an elemental non-transition metal, a salt of a non-transition metal, or a combination thereof.

18. The organometallic complex of claim 17, wherein the non-transition metal comprises a zinc component.

19. The organometallic complex of claim 1, wherein the second amino acid component and third amino acid component comprise an amino acid or a derivative thereof.

20. The organometallic complex of claim 19, wherein the second amino acid comprises a polar non-charged amino acid.

21. The organometallic complex of claim 20, wherein the second amino acid component comprises threonine.

22. The organometallic complex of claim 19, wherein the third amino acid component comprises a positively charged amino acid.

23. The organometallic complex of claim 22, wherein the third amino acid component comprises arginine.

24. A pharmaceutical composition comprising a therapeutic amount of the complex according to claim 1, wherein the therapeutic amount is effective to have anti-tumor or anti-cancer effect, the anti-tumor or anti-cancer effect comprising cytotoxicity of tumor cells or cancer cells, inhibited growth of tumor cells or cancer cells, inhibited migration of tumor cells or cancer cells, or any combination of these effects.

25. A method of treating a breast cancer or a pancreatic cancer comprising tumor cells in a mammal comprising:
(a) providing a therapeutic amount of the pharmaceutical composition according to claim 24, wherein the complex contains sphingomyelin as the first lipid component, linoleic acid as the second lipid component, ruthenium, zinc as the metal component, N-formyl methionine as the first amino acid component, threonine as the second amino acid component, arginine as the third amino acid component, and gamma globulin as the macromolecule component; and
(b) administering the therapeutic amount of the pharmaceutical composition to the mammal, wherein the therapeutic amount has a cytotoxic effect on the tumor cells.

26. The method of claim 25, wherein the tumor cells comprise a population of cells comprising mutations in chromatin-regulating genes.

27. The method of claim 26, wherein the tumor cells comprise a population of cells comprising a mutation in a histone deacetylase gene, a methyltransferase gene, or any combination thereof.

28. The method of claim 27, wherein the tumor cells comprise a population of cells of epithelial origin.

29. The method of claim 27, wherein the tumor cells comprise a population of breast tumor cells.

30. The method of claim 27, wherein the tumor cells comprise a population of pancreatic tumor cells.

31. The method of claim 27, wherein the administering is parentally, enterally, topically, or transdermally.

32. An organometallic complex of Formula I:

(First lipid)$_a$(Ru)$_b$(first amino acid)$_c$(Zn)$_d$(second amino acid)$_e$(second lipid)$_f$(third amino acid)$_g$(macromolecule)$_h$ wherein the first lipid component comprises a membrane lipid or a derivative thereof; the Ru signifies a ruthenium component; the first, second, and third amino acid components comprise an amino acid or a derivative thereof; the Zn signifies a zinc component; the second lipid component comprises a hydrocarbon chain of from 2 to twenty carbon atoms wherein at one end of the hydrocarbon chain (ω carbon) is a methyl group and at the other end (α carbon) is a carboxyl group, or a derivative thereof; the macromolecule component comprises a polypeptide chain;

wherein a, b, c, and h are at least 1; and d, e, f, and g are 0 or 1;

wherein e, f, and g are 0 when d is 0, and g is 0 when f is 0;

wherein the Ru component structurally associates the first lipid component with the first amino acid component; the Zn component structurally associates the first amino acid component with one or more of the second amino acid component or second lipid component; the third amino acid component is associated with the second lipid component; the macromolecule component associates with one or more of the first lipid component, the Ru component, the first amino acid component, the Zn component, the second amino acid component, the third amino acid component, or the second lipid component.

33. The organometallic complex of claim 32, wherein the ruthenium component is elemental ruthenium, or a ruthenium salt, selected from the group consisting of ruthenium chloride, ruthenium bromide, ruthenium iodide, ruthenium nitrate, ruthenium oxide, ruthenium sulfide, or a combination thereof.

34. The organometallic complex of claim 32, wherein the first lipid component comprises a sphingolipid or a derivative thereof.

35. The organometallic complex of claim 34, wherein the sphingolipid is a sphingomyelin or a derivative thereof.

36. The organometallic complex of claim 32, wherein the first amino acid component comprises an N-formyl methionine or a derivative thereof.

37. The organometallic complex of claim 32, wherein the second lipid component comprises a fatty acid component or a derivative thereof.

38. The organometallic complex according to claim 37, wherein the fatty acid component is linoleic acid or a derivative thereof.

39. The organometallic complex of claim 32, wherein the macromolecule component comprises an immunoglobulin or a derivative thereof.

40. The organometallic complex of claim 39, wherein the immunoglobulin comprises IgG or a derivative thereof.

* * * * *